(12) United States Patent
Parker et al.

(10) Patent No.: US 10,725,021 B2
(45) Date of Patent: *Jul. 28, 2020

(54) MUSCLE CHIPS AND METHODS OF USE THEREOF

(71) Applicant: President and Fellows of Harvard College, Cambridge, MA (US)

(72) Inventors: Kevin Kit Parker, Cambridge, MA (US); Josue A. Goss, Cambridge, MA (US); Anna Grosberg, Irvine, CA (US); Patrick W. Alford, Minneapolis, MN (US); Adam W. Feinberg, Pittsburgh, PA (US); Ashutosh Agarwal, Miami, FL (US); Megan Laura McCain, Culver City, CA (US); Johan Ulrik Lind, Boston, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 157 days.

This patent is subject to a terminal disclaimer.

(21) Appl. No.: 15/693,565

(22) Filed: Sep. 1, 2017

(65) Prior Publication Data

US 2018/0209957 A1 Jul. 26, 2018

Related U.S. Application Data

(63) Continuation of application No. 14/362,287, filed as application No. PCT/US2012/068787 on Dec. 10, 2012, now Pat. No. 9,857,356.

(60) Provisional application No. 61/697,121, filed on Sep. 5, 2012, provisional application No. 61/569,028, filed on Dec. 9, 2011.

(51) Int. Cl.
*G01N 33/50* (2006.01)

(52) U.S. Cl.
CPC ..... *G01N 33/5008* (2013.01); *G01N 33/5088* (2013.01); *G01N 2500/04* (2013.01); *G01N 2500/10* (2013.01)

(58) Field of Classification Search
CPC .......... G01N 2500/04; G01N 2500/10; G01N 33/5008; G01N 33/5088
See application file for complete search history.

(56) References Cited

U.S. PATENT DOCUMENTS

| | | |
|---|---|---|
| 8,492,150 B2 | 7/2013 | Parker et al. |
| 8,748,181 B2 | 6/2014 | Kuo et al. |
| 8,999,378 B2 | 4/2015 | Parker et al. |
| 9,012,172 B2 | 4/2015 | Parker et al. |
| 9,068,168 B2 | 6/2015 | Feinberg et al. |
| 9,383,350 B2 | 7/2016 | Parker et al. |
| 9,857,356 B2 * | 1/2018 | Parker .............. G01N 33/5088 |
| 2004/0009566 A1 | 1/2004 | Okano et al. |
| 2004/0078090 A1 | 4/2004 | Binette et al. |
| 2004/0101819 A1 | 5/2004 | Montemagno et al. |
| 2005/0080402 A1 | 4/2005 | Santamore et al. |
| 2005/0085847 A1 | 4/2005 | Galdonik et al. |
| 2006/0003439 A1 | 1/2006 | Ismagilov et al. |
| 2007/0060815 A1 | 3/2007 | Martin et al. |
| 2010/0196432 A1 | 8/2010 | Feinberg et al. |
| 2011/0189719 A1 | 8/2011 | Kuo et al. |
| 2011/0250585 A1 | 10/2011 | Ingber et al. |
| 2012/0134570 A1 | 5/2012 | Trumbull et al. |
| 2013/0046134 A1 | 2/2013 | Parker et al. |
| 2013/0330378 A1 | 12/2013 | Parker et al. |
| 2014/0236267 A1 | 8/2014 | Parker |
| 2015/0182679 A1 | 7/2015 | Parker et al. |
| 2015/0253307 A1 | 9/2015 | Parker et al. |
| 2016/0003806 A1 | 1/2016 | Parker et al. |

FOREIGN PATENT DOCUMENTS

| | | |
|---|---|---|
| WO | WO-2010/127280 A1 | 11/2010 |
| WO | WO-2012/131360 A2 | 10/2012 |
| WO | WO-2016/007879 A1 | 1/2016 |
| WO | WO-2016/045813 A1 | 3/2016 |
| WO | WO-2016/069142 A2 | 5/2016 |
| WO | WO-2016/191179 A1 | 12/2016 |

OTHER PUBLICATIONS

Grosberg A, Nesmith AP, Goss JA, Brigham MD, McCain ML, Parker KK "Muscle on a Chip: in vitro Contractility Assays for Smooth and Striated Muscle" J Pharmacol Toxicol Methods. May-Jun. 2012;65(3):126-35. doi: 10.1016/j.vascn.2012.04.001. Epub Apr. 12, 2012. (Year: 2012).*

Alford et al., "Biohybrid thin films for measuring contractility in engineered cardiovascular muscle" *Biomaterials* 31, May 2010, 3613-3621.

Badrossamay, M.R. et al. "Nanofiber assembly by rotary jet-spinning." Nano Letters, May 2010;10(6):2257-2261.

Bray et al., "Sarcomere Alignment is Regulated by Myocyte Shape" *Cell Motility and the Cytoskeleton*, Aug. 2008, 65(8), pp. 641-651.

Bursac et al., "Cardiomyocyte cultures with controlled macroscopic anisotropy." *Circulation Rearch*, Dec. 2002, vol. 91, pp. e45-e54.

Grosberg et al., "Ensembles of engineered cardiac tissues for physiological and pharmacological study: Heart on a chip." Lab Chip, Nov. 2011, vol. 11, p. 4165.

Lehnert et al., "Cell behavior on micropatterned substrata: limits of extracellular matrix geometry for spreading and adhesion."*Journal of Cell Science*, Jan. 2004, vol. 117 (1), pp. 41-52.

Mao et al., "Capillary isoelectric focusing with whole column imaging detection for analysis of proteins and peptides," J. Biochem. Biophys. Methods, Feb. 1999, 39:93-110.

Park et al., "Real-Time Measurement of the Contractile Forces of Self-Organized Cardiomyocytes on Hybrid Biopolymer Microcantilevers," Anal. Chem. Oct. 2005, 77:6571-6580.

(Continued)

*Primary Examiner* — Aaron J Kosar
(74) *Attorney, Agent, or Firm* — McCarter & English, LLP; Maria Laccotripe Zacharakis; Deborah L. Nagle

(57) ABSTRACT

The present invention provides high throughput assays for identifying compounds that modulate a contractile function, as well as devices suitable for use in these assays.

8 Claims, 46 Drawing Sheets

(56) References Cited

OTHER PUBLICATIONS

Parker et al., "Extracellular matrix, mechanotransduction and structural hierarchies in heart tissue engineering." Phil Trans R. Soc B, Epub, Jun. 22, 2007, vol. 362, pp. 1267-1279.
Spring, Kenneth R. "Electronic Imaging in Neuroscience," Curr. Protoc. Neurosci. May 2002, 2.4.1-2.4.9.
Yang et al., "Fabrication of well-defined PLGA scaffolds using novel microembossing and carbon dioxide bonding," Biomaterials, Sep. 2005, vol. 26, pp. 2585-2594.
Vandenburgh et al., "Drug-Screening Platform Based on the Contractility of Tissue-Engineered Muscle", Muscle Nerve 37:438-447, 2008.
Kim et al., "Biohybrid Microsystems Actuated by Cardiomyocytes: Microcantilever, Microrobot, and Micropump", Proceedings—IEEE International Conference on Robotics and Automation. 880-885. (2008).
Shimizu et al."Microfluidic devices for construction of contractile skeletal muscle microtissues" Journal of Bioscience and Bioengineering, vol. 119, Issue 2, Feb. 2015, pp. 212-216.
Luo, Y and Zare, RN, "Perforated membrane method for fabricating three-dimensional polydimethylsiloxane microfluidic devices", Lab Chip, 2008, 8, 1688-1694. doi: 10.1039/b807751g.
Xi et al., "Development of a Self-Assembled Muscle-Powered Piezoelectric Microgenerator", NSTI-Nanotech, 2004, vol. 1, pp. 3-6.

\* cited by examiner

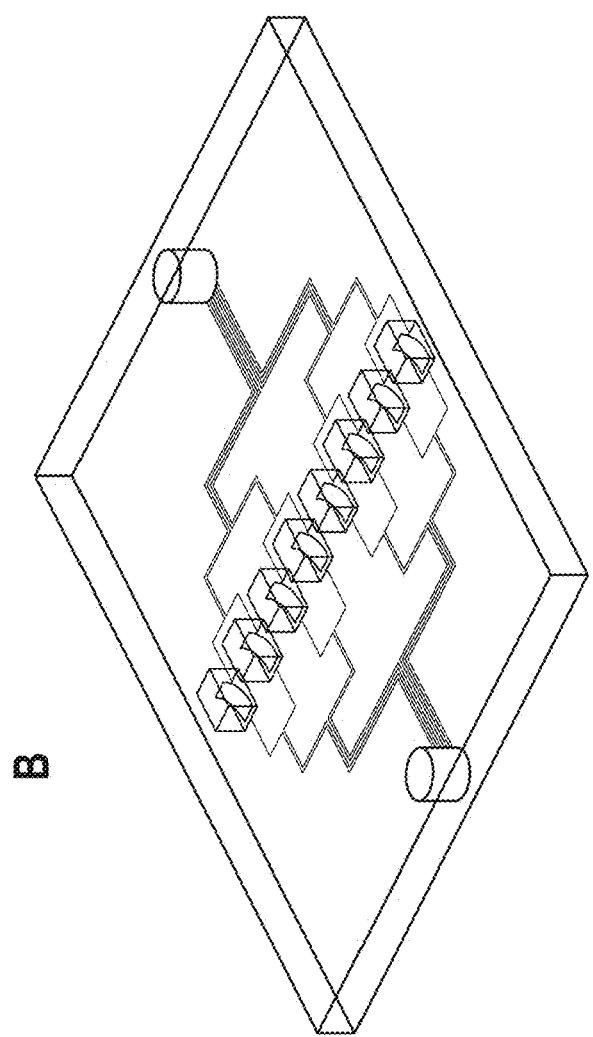
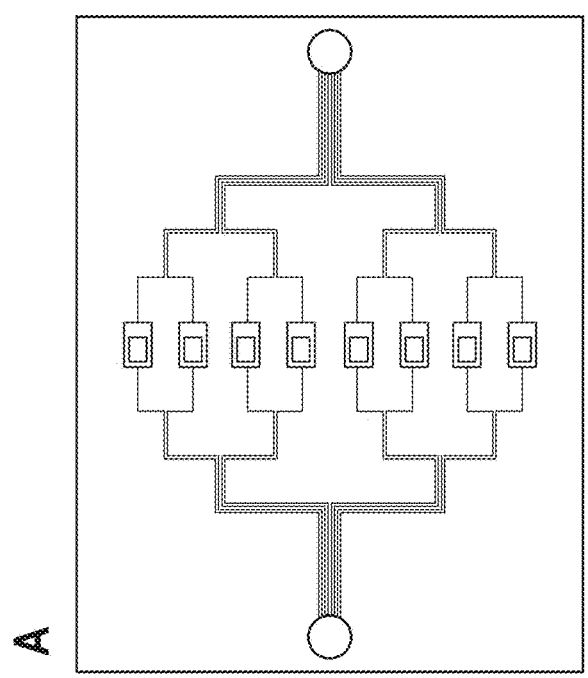
FIG. 13

FIG. 19
(A) MULTI-WELL PLATE "SHUTTER" DESIGN
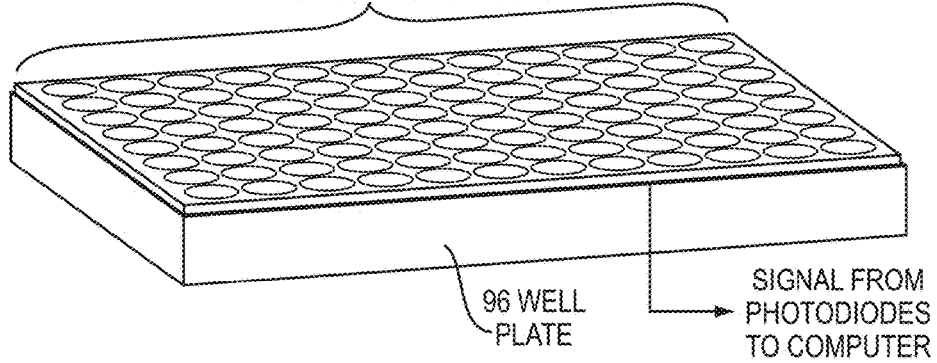
(B) CROSS-SECTION OF A "SHUTTER" WELL
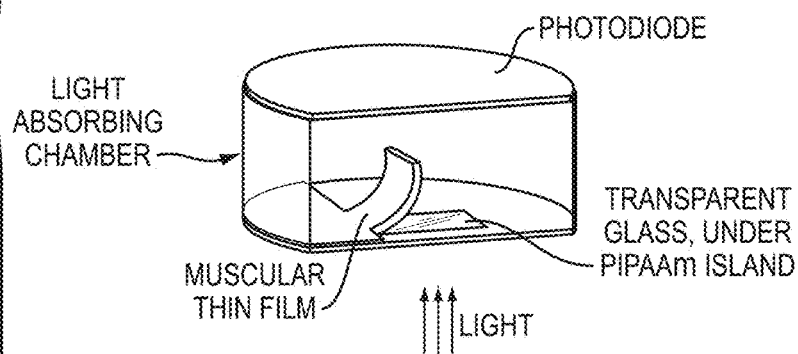
(C) TOP VIEW INTO A SINGLE "SHUTTER" WELL
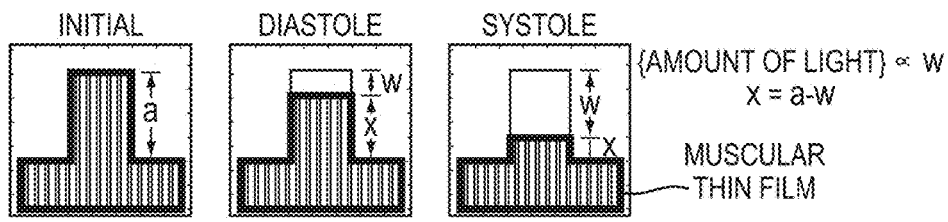

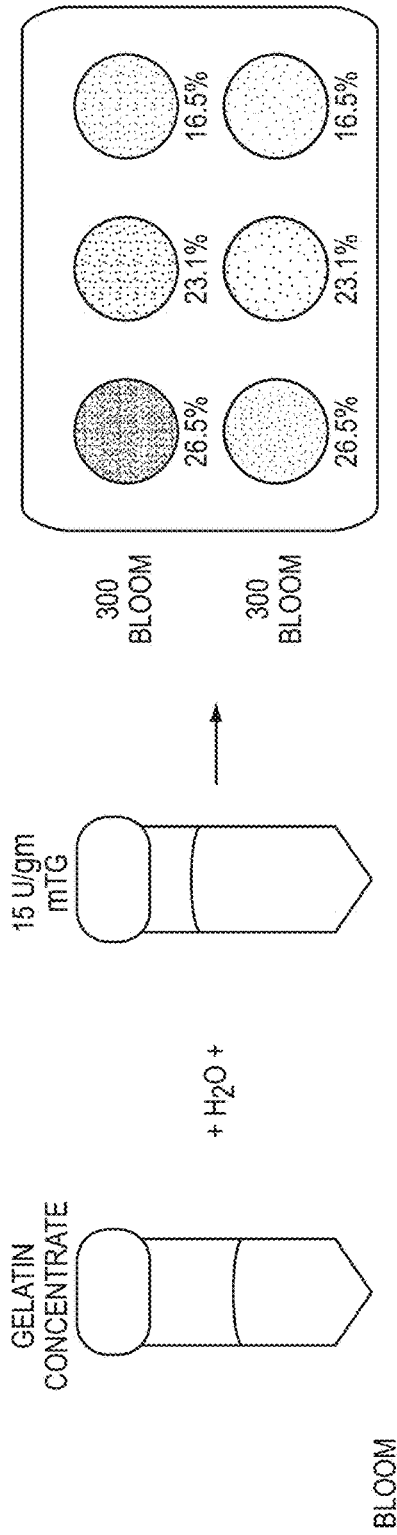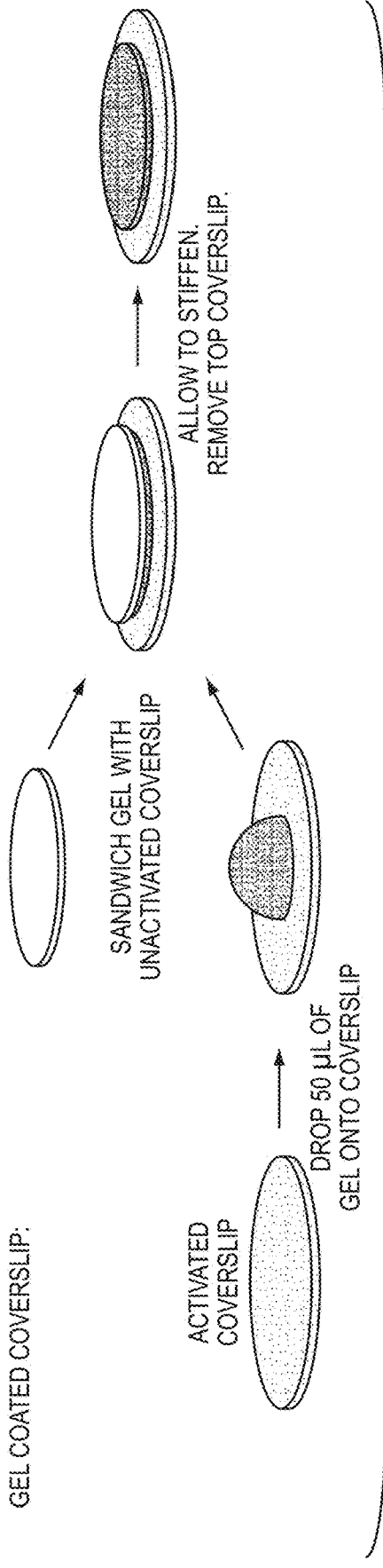
FIG. 32

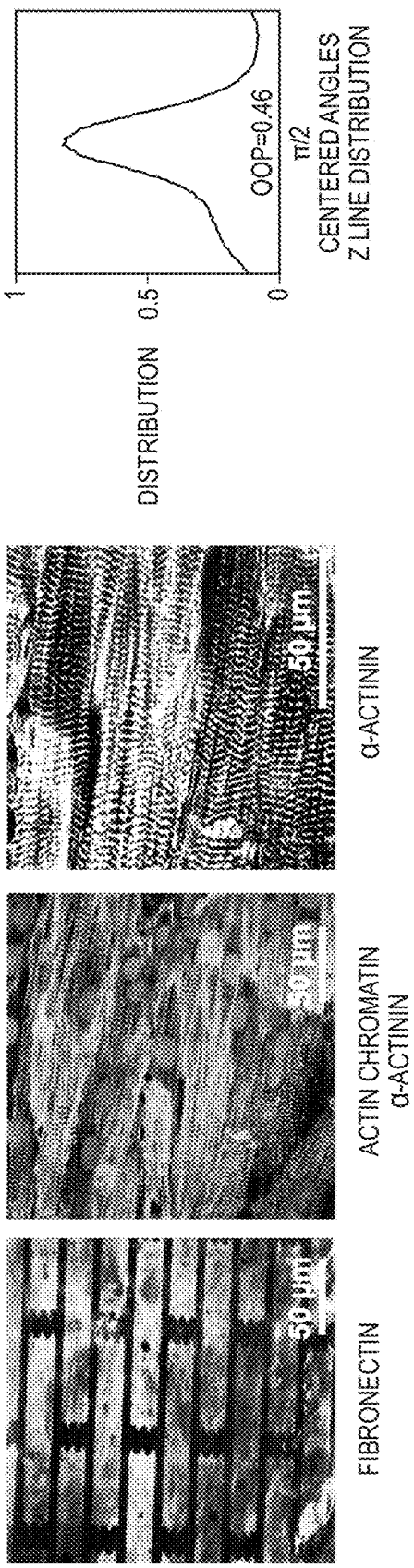
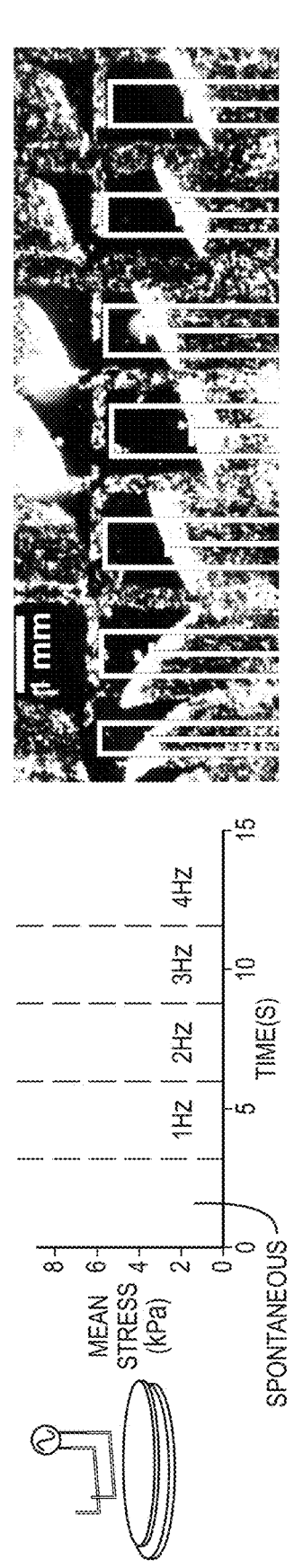
FIG. 35

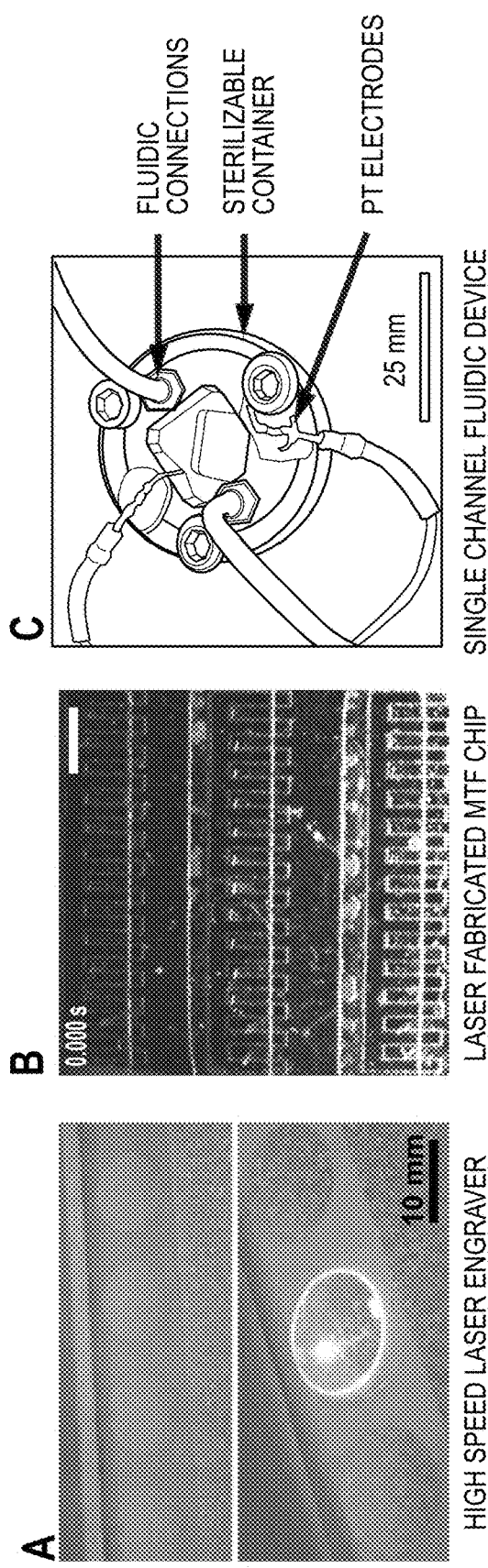
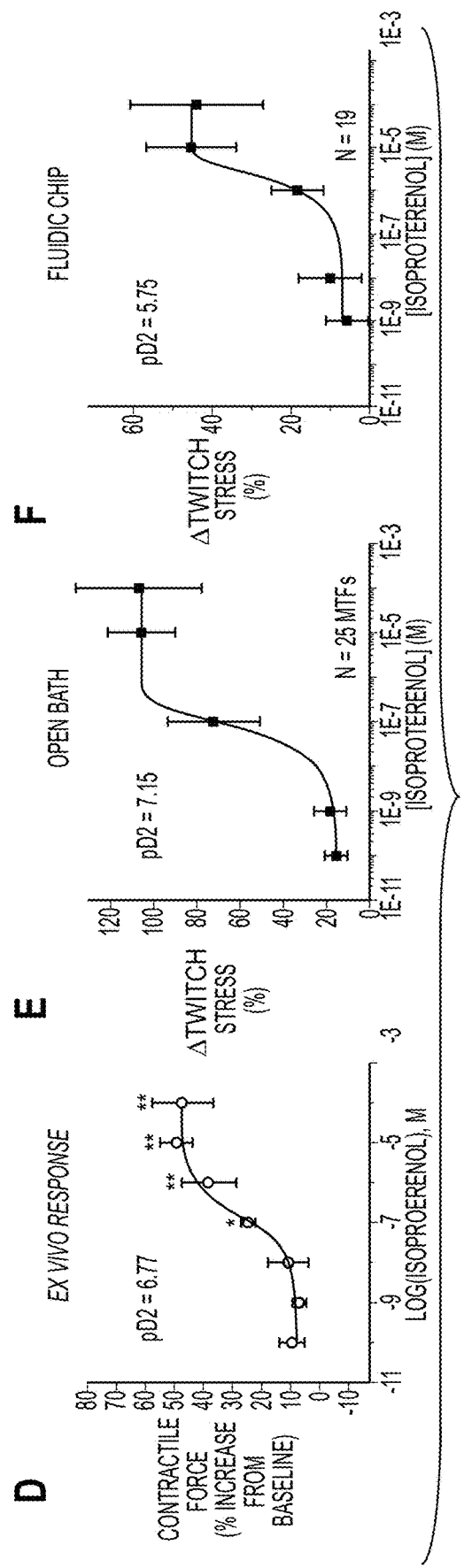
FIG. 36

MUSCLE CHIPS AND METHODS OF USE THEREOF

RELATED APPLICATIONS

This application is a continuation of U.S. patent application Ser. No. 14/362,287, filed on Jun. 2, 2014, which is a 35 U.S.C. § 371 national stage filing of International Application No. PCT/US2012/068787, filed on Dec. 10, 2012, which claims priority to U.S. Provisional Patent Application Ser. No. 61/569,028, filed on Dec. 9, 2011, and U.S. Provisional Patent Application Ser. No. 61/697,121, filed on Sep. 5, 2012, the entire contents of each of which are incorporated herein by reference.

GOVERNMENT SUPPORT

This invention was made with government support under grant number W911NF-12-2-0036, awarded by DARPA. The government has certain rights in the invention.

BACKGROUND OF THE INVENTION

Identification and evaluation of new therapeutic agents or identification of suspect disease associated targets typically employ animal models which are expensive, time consuming, require skilled animal-trained staff and utilize large numbers of animals. In vitro alternatives have relied on the use of conventional cell culture systems which are limited in that they do not allow the three-dimensional interactions that occur between cells and their surrounding tissue. This is a considerable disadvantage as such interactions are well documented as having a significant influence on the growth and activity of cells in vivo since in vivo cells divide and interconnect in the formation of complex biological systems creating structure-function hierarchies that range from the nanometer to meter scales.

Efforts to build biosynthetic materials or engineered tissues that recapitulate these structure-function relationships often fail because of the inability to replicate the in vivo conditions that coax this behavior from ensembles of cells. For example, engineering a functional muscle tissue requires that the sarcomere and myofibrillogenesis be controlled at the micron length scale, while cellular alignment and formation of the continuous tissue require organizational cues over the millimeter to centimeter length scale. Thus, to build a functional biosynthetic material, the biotic-abiotic interface must contain the chemical and mechanical properties that support multiscale coupling.

Accordingly, there is a need for improved methods and systems that may be used for determining the effect of a test compound on biologically relevant parameters in order to enhance and speed-up the drug discovery and development process.

SUMMARY OF THE INVENTION

Described herein are devices, otherwise referred to herein as muscle chips, and methods for multiplex and high throughput, high content measurements of physiologically relevant properties of in vitro tissue constructs. The devices of the present invention can be used in, for example, high throughput screening assays to determine the effects of a test compound on living tissue by examining the effect of the test compound on various biological responses, such as for example, cell viability, cell growth, migration, differentiation and maintenance of cell phenotype, electrophysiology, metabolic activity, muscle cell contraction, osmotic swelling, structural remodeling and tissue level pre-stress.

Accordingly, in one aspect the present invention provides engineered human muscle chips. Muscle chips are fluidic devices, e.g., millifluidic and/or microfluidic devices, that comprise living human cells cultured within the fluidic devices and recapitulate the three-dimensional (3D) tissue-tissue interfaces, mechanically active microenvironments, electrical stimulation, chemical conditions and complex organ-level functions. Examples of the muscle chips described herein, include but are not limited to, heart chips to mimic beating heart, lung airway smooth muscle chips to mimic reactive airway, and skeletal muscle chips to mimic contracting skeletal muscle.

Another aspect provided herein relates to kits comprising a plurality of muscle chips, for example, 2, 3, 4, 5, 6, 7, 8, 9, 10, or more muscle chips. In some embodiments, the muscle chips in the kit can be all the same, i.e., corresponding to the same muscle. In some embodiments, at least some of the muscle chips in the kit can represent a collection of different organs, e.g., heart, airway, skeletal muscle.

In some embodiments, each muscle chip can be individually packaged, e.g., for sterility. In some embodiments, the kits can further comprise an appropriate culture medium for each muscle chip. In some embodiments, the kits can further comprise an instruction manual, e.g., instructions on connecting various muscle chips together to form an integrated network.

In another aspect, the present invention provides methods for identifying a compound that modulates a contractile function. The methods include providing a device of the invention containing a plurality of muscle tissues, e.g., muscle thin films and/or hydrogel engineered muscle tissue, contacting a plurality of the muscle tissues with a test compound; and determining the effect of the test compound on a contractile function in the presence and absence of the test compound, wherein a modulation of the contractile function in the presence of the test compound as compared to the contractile function in the absence of the test compound indicates that the test compound modulates a contractile function, thereby identifying a compound that modulates a contractile function.

In another aspect, the present invention provides methods for identifying a compound useful for treating or preventing a muscle disease. The methods include providing a device of the invention containing a plurality of muscle tissues, e.g., muscle thin films and/or hydrogel engineered muscle tissue, contacting a plurality of the muscle tissues with a test compound; and determining the effect of the test compound on a contractile function in the presence and absence of the test compound, wherein a modulation of the contractile function in the presence of the test compound as compared to the contractile function in the absence of the test compound indicates that the test compound modulates a contractile function, thereby identifying a compound useful for treating or preventing a muscle disease.

In one embodiment, the contractile function is a biomechanical activity, e.g., a biomechanical activity selected from the group consisting of contractility, cell stress, cell swelling, and rigidity.

In another embodiment, the contractile function is an electrophysiological activity, e.g., a voltage parameter selected from the group consisting of action potential, action potential duration (APD), conduction velocity (CV), refractory period, wavelength, restitution, bradycardia, tachycardia, and reentrant arrhythmia; or a calcium flux parameter selected from the group consisting of intracellular calcium transient, transient amplitude, rise time (contraction), decay time (relaxation), total area under the transient (force), restitution, and focal and spontaneous calcium release.

In one embodiment, the methods of the invention further include applying a stimulus, such as an electrical stimulus, to the plurality of muscle tissues, e.g., muscle thin films and/or hydrogel engineered muscle tissue, within the devices of the invention.

In another embodiment, the plurality of muscle tissues, e.g., muscle thin films and/or hydrogel engineered muscle tissue, within the devices of the invention are adhered to a solid support structure, e.g., a Petri dish, a multi-well plate, or a glass cover-slip.

In yet another embodiment, the plurality of muscle tissues, e.g., muscle thin films and/or hydrogel engineered muscle tissue, within the devices of the invention are cultured in the presence of a fluorophore, such as a voltage-sensitive dye or an ion-sensitive dye. The voltage-sensitive dye may be an electrochromic dye (e.g., a styryl dye and a merocyanine dye). The ion-sensitive dye may be a calcium sensitive dye (e.g., X-Rhod, aequorin, Fluo3, Fluo5, or Rhod2). In other embodiments, the fluorophore may be a dye pair selected from the group consisting of di-2-ANEPEQ and calcium green; di-4-ANEPPS and Indo-1; di-4-ANEPPS and Fluo-4; RH237 and Rhod2; and, RH-237 and Fluo-3/4.

In some embodiments, the plurality of muscle tissues, e.g., muscle thin films and/or hydrogel engineered muscle tissues, within the devices of the invention comprise cardiomyocytes, vascular smooth muscle cells, smooth muscle cells, skeletal striated muscle cells, and airway smooth muscle cells.

In another aspect, the present invention provides a device for measuring a contractile function. The device includes a solid support structure (e.g., a Petri dish, a multi-well plate, or a glass cover-slip), a plurality of muscle tissues, e.g., muscle thin films and/or hydrogel engineered muscle tissue strips.

In some embodiments, the plurality of muscle tissues each comprise a flexible polymer layer (e.g., a flexible polymer layer comprising polydimethylsiloxane) and a population of isolated cells (e.g., myocytes such as cardiomyocytes) seeded on the flexible polymer layer in a predetermined pattern, and wherein the cells form a tissue structure which can perform a contractile function.

In other embodiments, the plurality of muscle tissues each comprise a hydrogel layer (e.g., alginate and/or gelatin) and a population of isolated cells (e.g., myocytes such as cardiomyocytes) seeded on the hydrogel layer in a predetermined pattern, and wherein the cells form a tissue structure which can perform a contractile function. The plurality of muscle tissues may be adhered to the solid support structure directly or indirectly, e.g., via a plurality of posts attached to the solid support structure.

In a further aspect, the present invention provides devices for measuring a contractile function which includes a solid support structure (e.g., a Petri dish, a multi-well plate, a microfluidics device, or a glass cover-slip). In one embodiment, the devices comprise a plurality of muscle tissues, e.g., muscle thin films and/or hydrogel engineered muscle tissues.

In one embodiment, the plurality of muscle tissues comprise a flexible polymer layer (e.g., a flexible polymer layer comprising polydimethylsiloxane) and a population of isolated cells (e.g., myocytes such as cardiomyocytes, airway smooth muscle cells, skeletal muscle cells) seeded on the flexible polymer layer in a predetermined pattern, wherein the cells form a tissue structure which can perform a contractile function.

In other embodiment, the plurality of muscle tissues comprise a hydrogel layer and a population of isolated cells (e.g., myocytes such as cardiomyocytes, airway smooth muscle cells, skeletal muscle cells) seeded on the hydrogel layer in a predetermined pattern, wherein the cells form a tissue structure which can perform a contractile function.

The myocytes may be aligned to produce an anisotropic tissue.

In certain embodiments, the microfluidic device comprises a first chamber and a second chamber operably connected. The first chamber may comprise a monolayer of muscle cells and an electrophysiological capturing device and the second chamber comprises a plurality of muscle tissues strips, e.g., horizontal muscle tissues, e.g., muscle thin films and/or hydrogel engineered muscle tissues, and a device to measure contractility.

In some embodiments, the plurality of muscle tissues comprise a flexible polymer layer and/or a hydrogel and a population of isolated muscle cells seeded on the flexible polymer layer and/or the hydrogel in a predetermined pattern, wherein the cells form a tissue structure which can perform a contractile function. The monolayer of muscle cells and the isolated muscle cells may be independently selected from the group consisting of cardiac muscle cells, ventricular cardiac muscle cells, atrial cardiac muscle cells, striated muscle cells, smooth muscle cells, vascular smooth muscle cells.

In other embodiments, the microfluidic device comprises a solid support structure comprising a first chamber and a second chamber operably connected. The first chamber may comprise a plurality of muscle tissues, e.g., horizontal muscle tissues, e.g., muscle thin films and/or hydrogel engineered muscle tissues, in some embodiments adhered at one end to the solid support structure and an optical signal capturing device.

In some embodiments the plurality of muscle tissues comprise a flexible polymer layer and a population of isolated diseased cells seeded on the flexible polymer layer in a predetermined pattern, wherein the cells form a tissue structure which can perform a contractile function.

In other embodiments, the plurality of muscle tissues comprise a hydrogel layer and a population of isolated diseased muscle cells seeded on the hydrogel layer in a predetermined pattern, wherein the cells form a tissue structure which can perform a contractile function.

The second chamber may comprise a plurality of muscle tissue strips and an optical signal capturing device.

In some embodiments the plurality of muscle tissues comprise a flexible polymer layer and a population of isolated healthy muscle cells seeded on the flexible polymer layer in a predetermined pattern, wherein said cells form a tissue structure which can perform a contractile function.

In some embodiments the plurality of muscle tissues comprise a hydrogel layer and a population of isolated healthy muscle cells seeded on the hydrogel layer in a predetermined pattern, wherein the cells form a tissue structure which can perform a contractile function.

In other embodiments, the microfluidic device comprises a plurality of muscle tissue strips.

In some embodiments the plurality of muscle tissues comprise a flexible polymer layer and a population of isolated airway smooth muscle cells seeded on the flexible polymer layer in a predetermined pattern, wherein said cells form a tissue structure which can perform a contractile function.

In some embodiments, the plurality of muscle tissues comprise a hydrogel layer and a population of isolated airway smooth muscle cells seeded on the hydrogel layer in a predetermined pattern, wherein the cells form a tissue structure which can perform a contractile function.

In one embodiment, the devices further comprise a porous membrane having epithelial cells adhered thereto and exposed to air flow situated above the muscle tissue strips.

In one embodiment, the solid support structure is a microfluidic device comprising a first chamber and a second chamber operably connected. The first chamber may comprise a plurality of muscle tissue strips comprising a population of isolated healthy airway smooth muscle cells and the second chamber may comprise a plurality of muscle tissue strips comprising a population of isolated diseased airway smooth muscle cells.

In one embodiment, the devices of the invention may comprise a second solid support structure seeded with a second population of cells.

In another embodiment, the flexible polymer layer and/or hydrogel layer is supplied with an engineered surface chemistry before the cells are seeded. The engineered surface chemistry may include an extracellular matrix protein. In other embodiments, the engineered surface chemistry is provided in a pattern that includes gaps.

In a further embodiment, the solid support structure includes a plurality of cell culture wells; an optical signal capture device; and an image processing software to calculate change in an optical signal. The optical signal capture device may further include fiber optic cables in contact with the culture wells.

In another aspect, the present invention provides methods of preparing a device suitable for measuring a contractile function. The methods include providing a solid support structure; coating a sacrificial polymer layer on the solid support structure; coating a flexible polymer layer that is more flexible than the support structure on the sacrificial polymer layer, wherein the flexible polymer layer does not cover the edges of the solid support structure; seeding cells on the flexible polymer layer; culturing the cells to form a tissue; and removing a portion of the formed tissue thereby generating strips of the formed tissue, thereby preparing a device suitable for measuring a contractile function.

The present invention is further illustrated by the following detailed description and drawings.

BRIEF DESCRIPTION OF THE DRAWINGS

FIG. 6(A) depicts imaging and mapping of all the wells of a multi-well plate assay at once and FIG. 6(B) depicts imaging and mapping of each well of a multi-well plate assay individually.

FIGS. 13(A) and 13(B) are top view (A) and side view (B) schematic representations of one embodiment of the devices of the invention depicting MTFs enclosed in individual chambers of a microfluidics device. Utilizing microfluidic principles of laminar flow and mixing, a small amount of nanoparticles or small molecules can be diluted into a wide variety of concentrations in simultaneous assays for tissue function.

FIG. 19 schematically depicts an embodiment of the fabrication of a "shutter" horizontal MTF device in a multi-well dish. (A) A 96-well plate with a photodiode array top. Each photodiode measures, as a function of time, the amount of light emitted from each well, which holds a single horizontal MTF. The readouts of the photodiodes are transferred to a computer, where they are directly converted to a measurement of the radius of curvature, and muscle layer stress. (B) A cross-section of a single well with a "shutter design". The bottom of the plate is made from glass that has been blacked out except for a small area under the muscular thin film, which remains transparent to light. The muscular thin films are made from non-transparent bio-compatible polymers, i.e. black PDMS. The walls of the plate are made from black plastic, or other light absorbing material, to eliminate the reflection of light. During contraction of the cells, the thin film bends up from the glass uncovering a larger area of the transparent glass, allowing for a greater amount of light to pass through the chamber. The photodiode is located at the top of the well, where it collets light throughout the contraction cycle. (C) The top view into a single well of the "shutter system". This illustrates that the island of transparent glass has the same area as an unbent film (length a). As the film dissociates from the glass it bends up slightly during diastole, exposing some of the transparent glass. During the contraction the film bends up more, exposing more of the transparent glass. The amount of light reaching the photodiode will be proportional to the area of the white rectangle. As the width of the rectangle remains constant the signal is proportional to w which is simply the length of the film minus the x-projection. Therefore the signal transmitted from the photodiodes is proportional to the x-projection. Example 2 and FIG. 7C describe how to calculate the radius of curvature from measurements of the x-projection. However, the use of a photodiode array dispenses with the need for image analysis as the x-projection is a direct readout. This allows for this device to be an automated, high-throughput, simultaneous contraction measuring device.

FIG. 32 depicts one embodiment for the fabrication of hydrogels crosslinked with microbial transglutaminase (mTG) and having various blooms.

FIG. 35 depicts the anisotropic growth of cardiac myocytes on micropatterned alginate hydrogels. Immunostaining of the tissue demonstrates that these micropatterned hydrogels are good substrates for formation of confluent anisotropic tissues. This Figure also depicts the construction of a contactility assay using micropatterned alginate substrates for quantification of contractile stresses generated by anisotropic muscular tissue on the hydrogel.

FIG. 36 depicts one embodiment of a heart-on-a-chip. (A) A commercially available $CO_2$ engraving laser was used to fabricate and cut out thin film cantilevers of muscle tissue on PDMS. This technique increases the throughput of the readout and makes the fabrication standardized and scalable (B) Figure depicting the higher throughput chip during a typical experiment. (C) Design for a one channel fluidic device using a 18 mm circular MTF chip. The device was built out of autoclaveable materials which incorporate various features required for an optical cardiac contractility assay: metallic base which fits on a heating element for temperature control, transparent top for recording cantilever deformation and embedded electrodes for electrical field stimulation of the tissue. (D,E,F) Validation of the platform as assessed by dose response of the tissue to a drug. Concentration dependent relationship of contraction to isoproterenol concentration collected from (D) ex vivo from rat ventricular myocardium strips (N=4), MEAN±SEM, *P<0.05, **P<0.01 vs baseline, (E) Collected in vitro from open well heart on a chip (N=25 MTFs from the same chip), MEAN±SEM, and (F) Collected in vitro from fluidic heart on a chip (N=19 MTFs from the same chip), MEAN±SEM.

DETAILED DESCRIPTION OF THE INVENTION

Figure 1:
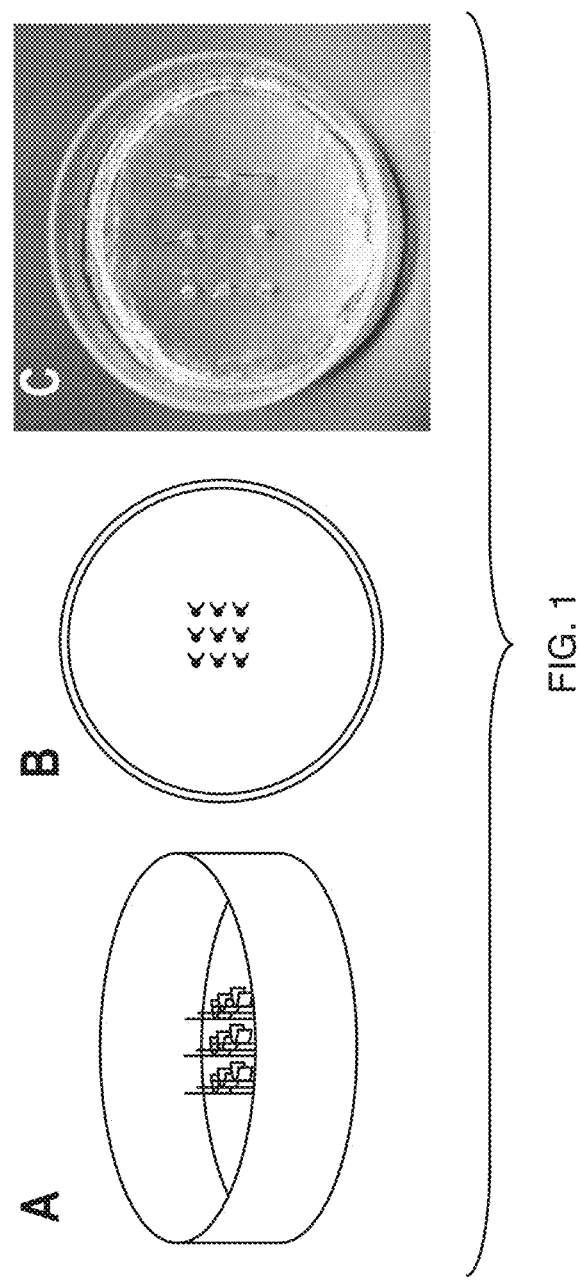
FIG. 1 depicts a device of the invention in which a homogeneous cell population is used. (A, B) Schematic representations of the device, with thin polymer films adhered to posts. (C) Photograph of the same device.

Described herein are devices and methods for multiplex and high throughput measurements of various properties of in vitro tissue constructs, e.g., for simultaneous or high-speed serial analysis of numerous samples. The devices and methods of the present invention can be used to measure muscle activities or functions, e.g., biomechanical forces that result from stimuli that include, but are not limited to, muscle cell contraction, osmotic swelling, structural remodeling and tissue level pre-stress. The devices and methods of the present invention may also be used for the evaluation of muscle activities or functions, e.g., electrophysiological responses, in a non-invasive manner, for example, in a manner that avoids cell damage. The devices and methods of the present invention are also useful for investigating muscle cell developmental biology and disease pathology, as well as in drug discovery and toxicity testing.

In certain aspects of the invention, the devices are muscle chips, and the methods include use of muscle chips for multiplex and high throughput measurements of various properties of in vitro tissue constructs, e.g., muscle activities or functions, muscle cell developmental biology and disease pathology, as well as in drug discovery and toxicity testing, e.g., for simultaneous or high-speed serial analysis of numerous samples.

I. Devices of the Invention and Methods of Production of the Same

In one aspect, the present invention provides devices, e.g., devices for measuring a contractile function, which comprise a solid support structure, a plurality of engineered muscle tissue strips, e.g., muscle thin films (MTFs) and/or hydrogel engineered muscle tissues.

In some embodiments, the plurality of muscle tissues each comprise a flexible polymer layer and a population of isolated cells seeded on the flexible polymer layer in a predetermined pattern, and wherein the cells form a tissue structure which can perform a contractile function.

In some embodiments, the plurality of muscle tissues each comprise a hydrogel layer and a population of isolated cells seeded on the hydrogel layer in a predetermined pattern, and wherein the cells form a tissue structure which can perform a contractile function.

In some embodiments, the engineered muscle tissues may be adhered to the solid support structure directly or indirectly, e.g., via the use of a post (e.g., the middle of an MTF is adhered to the post, as described in further detail below and depicted in FIGS. 1-4). In some embodiments one end of the muscle tissue strip is adhered to the solid support structure. In other embodiments, one end (as in FIG. 7A) or both ends of the engineered muscle tissue may be adhered to the solid support structure. In yet other embodiment, substantially all of the engineered muscle tissue is adhered to the solid support structure. In other embodiments, the muscle tissue strip is not adhered to the solid support structure.

In one embodiment, the engineered muscle tissue, e.g., MTFs, that are used in the devices and methods of the present invention may be prepared as described in U.S. Patent Publication Nos. 2009/0317852 and 2012/0142556, the entire contents of each which are incorporated herein by reference. Briefly, substrates or devices for use in the methods of the invention are fabricated using a rigid base material coated with a sacrificial polymer layer; a flexible polymer layer is temporarily bonded to the rigid base material via the sacrificial polymer layer, and an engineered surface chemistry is provided on the flexible polymer layer to enhance or inhibit cell and/or protein adhesion. Cells are seeded onto the flexible polymer layer, and cultured to form a tissue comprising, for example, patterned anisotropic myocardium. A desired shape of the flexible polymer layer can then be cut; and the flexible film, including the polymer layer and tissue, can be peeled off with a pair of tweezers as the sacrificial polymer layer dissolves to release the flexible polymer layer, to produce a free-standing film.

Figure 31:
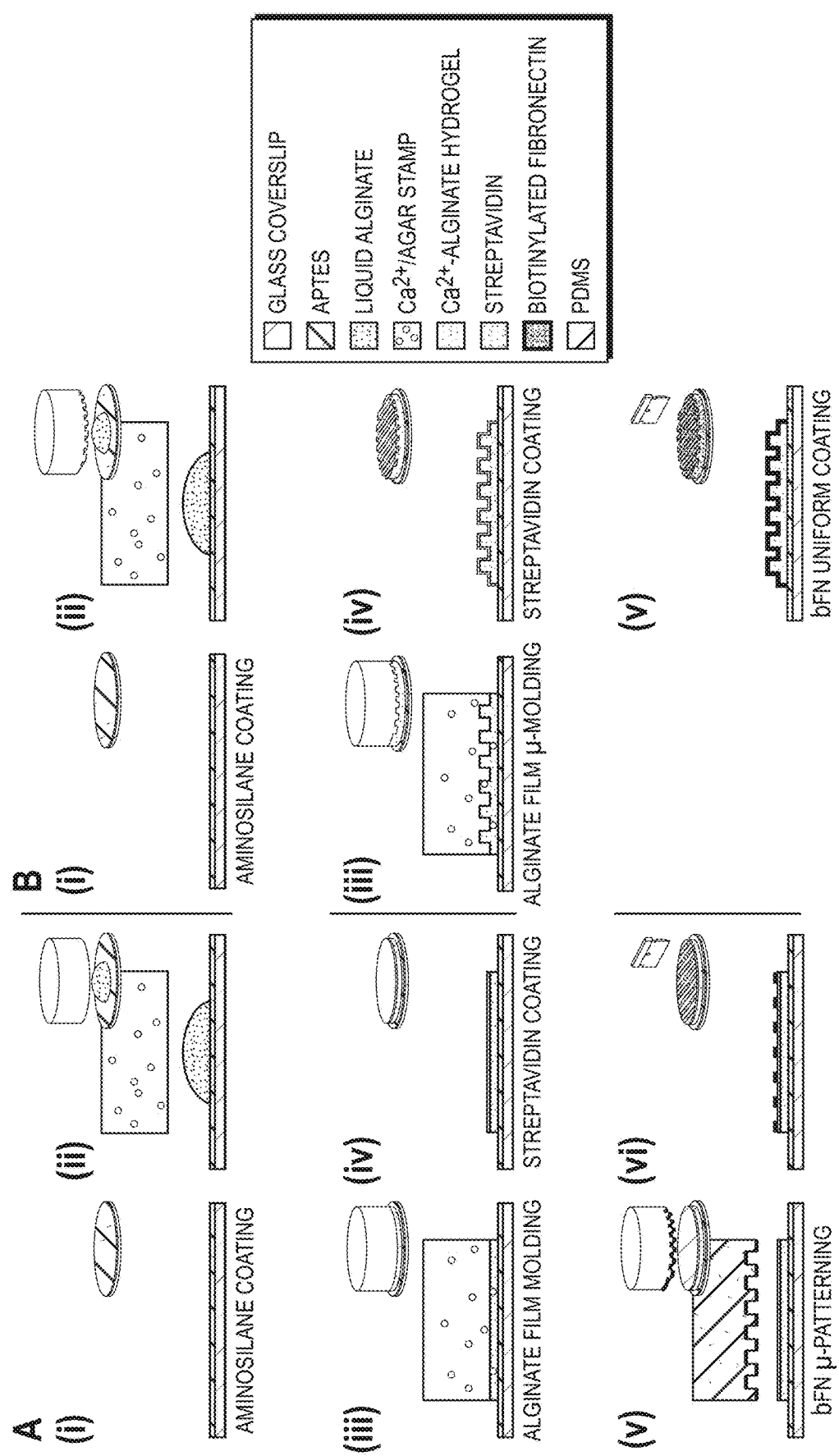
FIG. 31 depicts two exemplary methods for patterning hydrogel substrates, such as alginate, for fabrication of hydrogel engineered muscle tissue: Micro-contact printing (A) and Micro-Molding (B). (A) For microcontact printing, an alginate film is produced by first crosslinking the alginate using a flat, calcium loaded agar stamp. As engineered surface chemistries (e.g., proteins, e.g., extracellular matrix proteins) will not adhere to the alginate, the crosslinked alginate is functionalized by coupling an adhesive molecule to the alginate, such as streptavidin, using carbodiimide chemistry. Then, a microcontact printing technique is used to transfer a biotinylated engineered surface chemistries (e.g., protein, e.g., extracellular matrix proteins, e.g., biotinylated fibronectin, biotinylated collagen, biotinylated laminin, biotinylated RGD peptides) onto the top of the alginate thin film via a PDMS stamp. (B) For micromolding, a patterned calcium-loaded agar stamp is applied on a drop of alginate. Calcium diffuses into the alginate and crosslinks and stiffens it leaving behind the inverse of microtopographical patterns of the agar stamp. The thin film of hydrogel is then submerged in a solution of streptavidin mixed with the reagents EDC and Sulfo-NHS to functionalize the alginate and then biotinylated fibronectin is applied.
Figure 33:
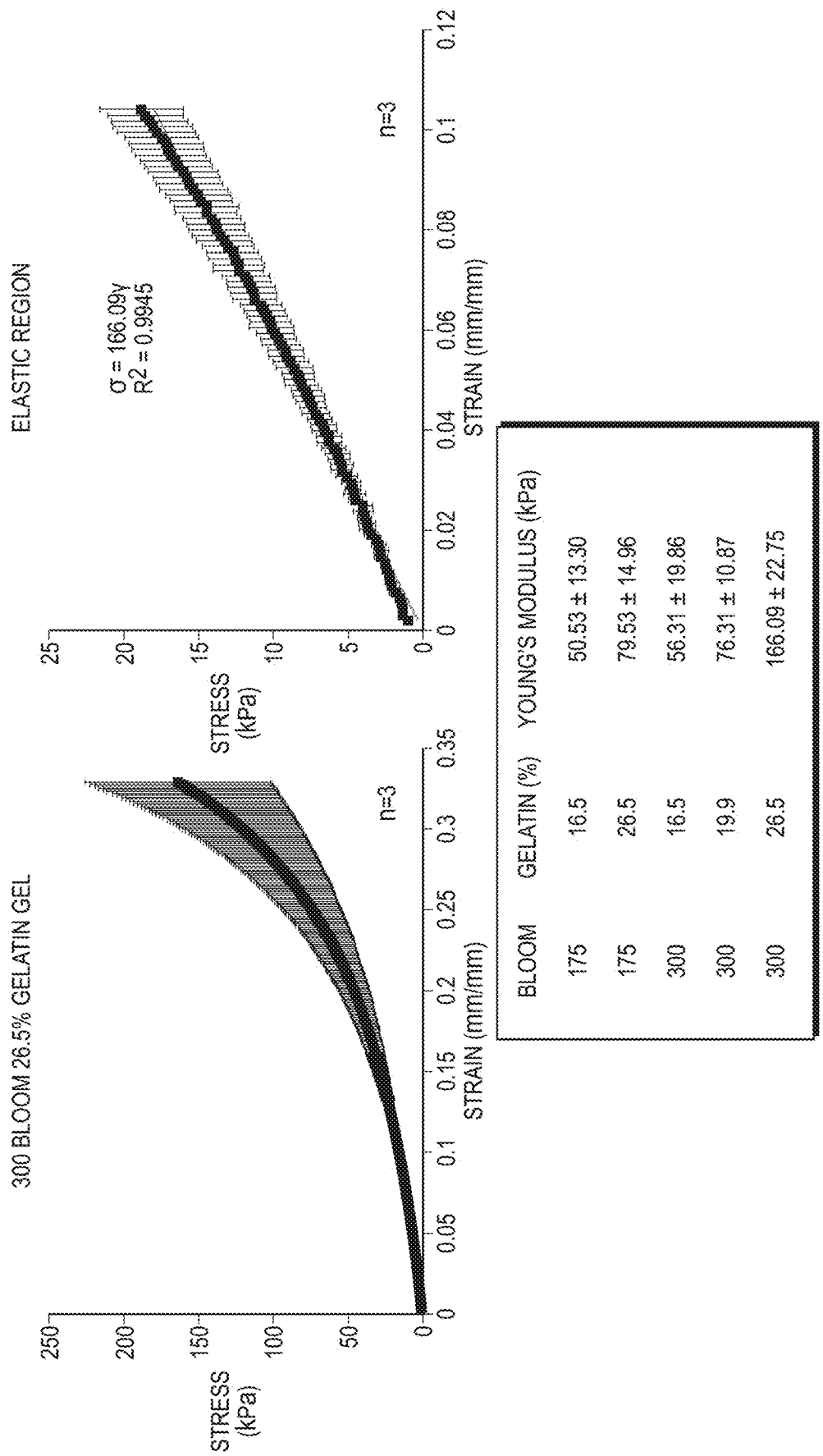
FIG. 33 depicts the mechanical properties of various gelatin hydrogels.
Figure 34:
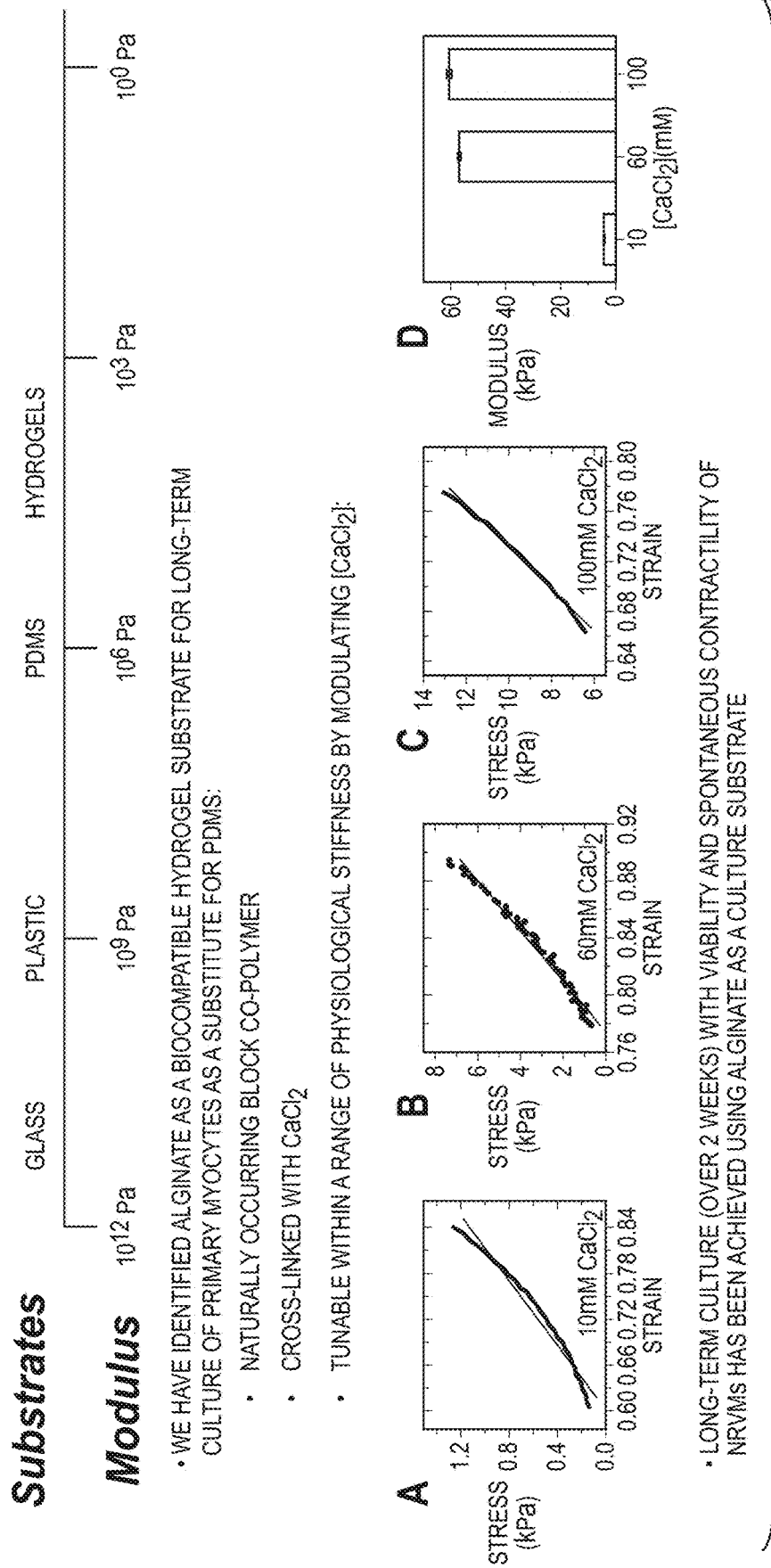
FIG. 34 depicts the mechanical properties of various alginate hydrogels. The Young's modulus of the alginate is tailored by using different $CaCl_2$ crosslinking concentrations. By matching the mechanical properties of the native myocardium, the viability of primary cardiac myocytes in culture is increased and the functionality of primary cardiac myocytes in culture is maintained.

In another embodiment, the muscle tissues that are used in the devices and methods of the invention are prepared as depicted in FIGS. 31 and/or 37.

The base layer for the muscle tissues may be formed of a rigid or semi-rigid material, such as a plastic, metal, ceramic, or a combination thereof. In one embodiment, the base layer is transparent so as to facilitate observation. In another embodiment, the base layer is opaque (e.g., light-absorbing). In one embodiment, a portion of the base layer is transparent (i.e., a portion underneath a portion of the muscle tissue) and the remaining portion is opaque. In yet another embodiment, the base layer is translucent. The base layer is ideally biologically inert, has low friction with the tissues and does not interact (e.g., chemically) with the tissues. Examples of materials that can be used to form the base layer include polystyrene, polycarbonate, polytetrafluoroethylene (PTFE), polyethylene terephthalate, quartz, silicon, and glass. In one embodiment, the base layer is a silicon wafer, a glass cover slip, a multi-well plate, a tissue culture plate, a Petri dish, or a fluidic (millifluidics or microfluidics) chamber.

In one embodiment, the base layer and the solid support structure are the same. For example, as described below, a muscle tissue may be fabricated on, for example, a glass cover-slip (the base layer) and subsequent to coating a flexible polymer layer onto the sacrificial polymer layer, the rigid base material is cut into sections. Such sections may be placed in, for example, a multi-well plate or a fluidics chamber.

In another embodiment, the solid support structure and the base layer are different. For example, as described below, a muscle tissue may be fabricated on, for example, a glass cover-slip (the base layer) which is subsequently cut into strips and applied to a solid support structure, such as a post adhered to a Petri-dish or placed in a fluidics chamber.

The sacrificial polymer layer is deposited on the base layer, i.e., is placed or applied onto the base layer. Depositing may include, but is not limited to, spraying, dip casting, and spin-coating. The sacrificial polymer layer may be deposited on substantially the entire surface or only a portion of the surface of the base layer.

In one embodiment, spin-coating is used to deposit the sacrificial polymer layer on the base material. "Spin-coating" is a process wherein the base layer is mounted to a chuck under vacuum and is rotated to spin the base layer about its axis of symmetry while a liquid or semi-liquid substance, e.g. a polymer, is dripped onto the base layer. Centrifugal force generated by the spin causes the liquid or semi-liquid substance to spread substantially evenly across the surface of the base layer.

In one embodiment, the sacrificial polymer is a thermally sensitive polymer that can be melted or dissolved to release the flexible polymer layer. For example, linear non-crosslinked poly(N-Isopropylacrylamide) (PIPAAM), which is a solid when dehydrated or at about 37° C., wherein the polymer is hydrated, but relatively hydrophobic. When the temperature of the polymer is dropped to about 35° C. or less, wherein the polymer is hydrated, but relatively hydrophilic, the polymer liquefies, thereby releasing the patterned flexible polymer layer (Feinberg et al., *Science* 317:1366-1370, 2007).

In another embodiment, the sacrificial polymer becomes hydrophilic when the temperature is lowered, thereby releasing hydrophobic coatings. For example, the sacrificial polymer can be hydrated, cross-linked PIPAAM, which is hydrophobic at about 37° C. and hydrophilic at about 35° C. or less (e.g., about 35° C. to about 32° C.). In yet another embodiment, the sacrificial polymer is an electrically actuated polymer that becomes hydrophilic upon application of an electric potential and releases a hydrophobic structure coated thereon. Examples of such a polymer include poly (pyrrole)s, which are relatively hydrophobic when oxidized and hydrophilic when reduced. Other examples of polymers that can be electrically actuated include poly(acetylene)s, poly(thiophene)s, poly(aniline)s, poly(fluorene)s, poly(3- hexylthiophene), polynaphthalenes, poly(p-phenylene sulfide), and poly(para-phenylene vinylene)s. In another embodiment, the sacrificial polymer is a degradable biopolymer that can be dissolved to release a structure coated thereon. For example, the polymer (e.g., polylactic acid, polyglycolic acid, poly(lactic-glycolic) acid copolymers, or nylons) undergoes time-dependent degradation by hydrolysis or by enzymatic action (e.g., fibrin degradation by plasmin, collagen degradation by collagenase, fibronectin degradation by matrix metalloproteinase).

In one embodiment, the sacrificial polymer is an ultra-hydrophobic polymer with a surface energy lower than the flexible polymer layer adhered to it. In this case, mild mechanical agitation will "pop" the patterned flexible polymer layer off of sacrificial polymer layer. Examples of such a polymer include but are not limited to alkylsilanes (octadecyltrichiorosilane and isobutyltrimethoxysilane), fluoroalkylsilanes (tridecafluorotetrahydrooctyltrichiorosilane, trifluoropropyltrichiorosilane and heptadecafluorotetrahydrodecyltrichlorosilane), silicones (methyihydrosiloxane-dimethylsiloxane copolymer, hydride terminated polydimethylsiloxane, trimethylsiloxy terminated polydimethylsiloxane and diacetoxymethyl terminated polydimethylsiloxane), fluorinated polymers (polytetrafluoroethylene, perfluoroalkoxy and fluorinated ethylene propylene). For example, the base material can be a glass cover slip coated with a sacrificial polymer layer of PIPAAM.

Examples of the elastomers that can be used to form the flexible polymer layer include polydimethylsiloxane (PDMS) and polyurethane. In one embodiment, the PDMS, once cured is opaque (e.g., light-absorbing). In other embodiments, thermoplastic or thermosetting polymers are used to form the flexible polymer layer. Alternative non-degradable polymers include polyurethanes, silicone-urethane copolymers, carbonate-urethane copolymers, polyisoprene, polybutadiene, copolymer of polystyrene and polybutadiene, chloroprene rubber, Polyacrylic rubber (ACM, ABR), Fluoro silicone Rubber (FVMQ), Fluoroelastomers, Perfluoroelastomers, Tetrafluoro ethylene/propylene rubbers (FEPM) and Ethylene vinyl acetate (EVA).

Figure 37:
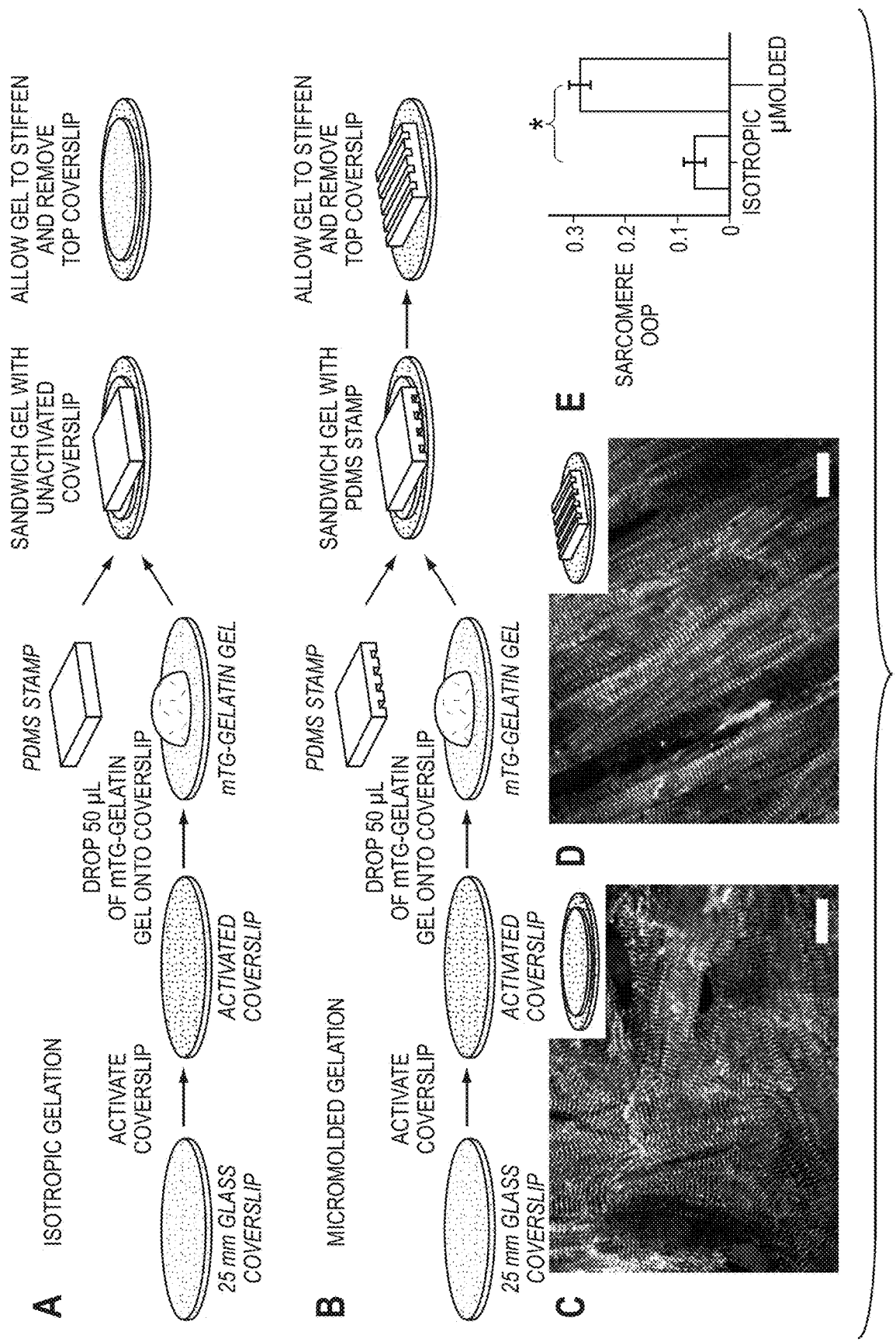
FIG. 37 schematically depicts one embodiment for the fabrication of (A) flattened and (B) micromolded hydrogel surfaces, such as gelatin. As cells generally stick to gelatin hydrogels, there is no need to engineer its surface chemistry prior to cell culture, as it is with hydrogels such as alginate (see, e.g., FIG. 31). Cardiac myocytes cultured on (C) flattened gelatin and (D) micromolded gelatin form isotropic and anisotropic monolayers, respectively. (E) Micromolding increases the sarcomere orientational order parameter (OOP) for engineered cardiac tissues.

In still other embodiments, biopolymers, such as collagens, elastins, polysaccharides, and other extracellular matrix proteins, are used to form a layer for producing muscle tissue (see, e.g., FIGS. 31 and 37). Suitable biodegradable elastomers include hydrogels, e.g., alginate and gelatin, elastin-like peptides, polyhydroxyalkanoates and poly(glycerol-sebecate). Suitable non-elastomer, biodegrable polymers include polylactic acid, polyglycolic acid, poly lactic glycolic acid copolymers.

In one embodiment, the flexible polymer layer comprises polydimethylsiloxane (PDMS). Thickness of the PDMS layer can be controlled by the viscosity of the prepolymer and by the spin-coating speed, ranging from 14 to 60 µm thick after cure. The viscosity of the prepolymer increases as the cross-link density increases. This change in viscosity between mixing and gelation can be utilized to spin-coat different thicknesses of flexible polymer layers. Alternatively the spin-coating speed can be increased to create thinner polymer layers. After spin-coating, the resulting polymer scaffolds are either fully cured at room temperature (generally, about 22° C.) or at 65° C.

Hydrogels suitable for use in the device of the invention include, for example, polyacrylamide gels, poly(N-isopropylacrylamide), pHEMA, collagen, fibrin, gelatin, alginate, and dextran. In one embodiment the hydrogel is alginate. In another embodiment, the hydrogel is gelatin. In one embodiment, the stiffness of the hydrogel is tuned to mimic the mechanical properties of healthy muscle tissue, e.g., cardiac tissue in vivo, e.g., to have a Young's modulus of about 10, 11, 12, 13, 14, 15, 16, 17, 18, 19, or about 20 kPa. In another embodiment, the stiffness of the hydrogel is tuned to mimic the mechanical properties of diseased muscle tissue, e.g., cardiac tissue in vivo, e.g., to have a Young's modulus of greater than about 45, 46, 47, 48, 49, 50, 51, 52, 53, 54, or about 55 kPa.

In one embodiment, polymeric fibers prepared as described in U.S. Patent Publication No. 2012/0135448, (the entire contents of which are incorporated herein by reference) may be used as for the sacrificial polymer layer and/or the flexible polymer layer.

In one embodiment, e.g., nanoparticles and/or fluorescent beads, e.g., fluorospheres, are mixed with the hydrogel prior to cross-linking and/or the flexible polymer layer prior to spin-coating the flexible polymer layer onto the sacrificial polymer layer.

The hydrogel layer and/or the flexible polymer layer may be uniformly or selectively patterned with engineered surface chemistry to elicit, e.g., an extracellular matrix protein, (or inhibit, e.g., a Pluronic) specific cell growth and function. The engineered surface chemistry can be provided via contact printing, exposure to ultraviolet radiation or ozone or via acid or base wash or plasma treatment to increase the hydrophilicity of the surface. In some embodiments, the hydrogel is micro-molded to have selective spatially patterned dimensions to elicit (or inhibit) specific cell growth and function (see, e.g., FIG. 31).

A specific biopolymer (or combination of biopolymers) may be selected to recruit different integrins, or an engineered surface chemistry may be fabricated on the flexible polymer layer and/or hydrogel layer to enhance or inhibit cell and/or protein adhesion. The specific type of biopolymer used and geometric spacing of the patterning will vary with the application. In one embodiment, the engineered surface chemistry comprises a biopolymer, such as an ECM protein, to pattern specific cell types. The ECM may comprise fibronectin, laminin, one or more collagens, fibrin, fibrinogen, or combinations thereof.

In some embodiments, prior to uniformly or selectively patterning a hydrogel with an engineered surface chemistry to elicit, e.g., an extracellular matrix protein, (or inhibit, e.g., a Pluronic) specific cell growth and function, the hydrogel is coated with a compound to permit covalent attachment of an engineered surface chemistry, such as an extracellular matrix protein. For example, as depicted in FIG. 31, an alginate film is coated with streptavidin prior to spatially patterning biotinylated fibronectin.

In one embodiment, the ECM is not uniformly distributed on the surface of the flexible polymer and/or hydrogel, but rather is patterned spatially using techniques including, but not limited to, soft lithography, self assembly, printed on the solid support structure with a polydimethylsiloxane stamp, vapor deposition, and photolithography. In one embodiment, the methods of the invention further comprise printing multiple biopolymer structures, e.g., the same or different, with successive, stacked printings. 2009/0317852-A1.

In one embodiment of the invention, a muscle tissue is engineered using alternating high density lines of ECM protein with either low density ECM protein or a chemical that prevents protein adhesion (e.g., Pluronics F127). The spacing of these lines is typically 20 µm width at 20 µm spacing, (Feinberg, *Science* 317:1366-1370, 2007), however, the width and spacing may be altered to change the alignment. Changes in alignment in turn affect anisotropy and anisotropy ratio of the action potential propagation. The width and spacing of the ECM lines may be varied over the range from about 0.1 μm to about 1000 μm, from about 1 μm to about 500 μm, from about 1 μm to 250 μm, from about 1 μm to 100 μm, from about 1 μm to 90 μm, from about 1 μm to 80 μm, from about 1 μm to 70 μm, from about 1 μm to 60 μm, from about 1 μm to 50 μm, from about 1 μm to 40 μm, from about 1 μm to 30 μm, from about 1 μm to 20 μm, from about 1 μm to 10 μm, from about 2 μm to 100 μm, from about 2 μm to 90 μm, from about 2 μm to 80 μm, from about 2 μm to 70 μm, from about 2 μm to 60 μm, from about 2 μm to 50 μm, from about 2 μm to 40 μm, from about 2 μm to 30 μm, from about 2 μm to 20 μm, from about 2 μm to 10 μm, from about 1 μm to 100 μm, from about 5 μm to about 100 μm, from about 5 μm to about 90 μm, from about 5 μm to about 80 μm, from about 5 μm to about 70 μm, from about 5 μm to about 60 μm, from about 5 μm to about 50 μm, from about 5 μm to about 40 μm, from about 5 μm to about 30 μm, from about 5 μm to about 20 μm, and from about 5 μm to about 20 μm.

The width and spacing of the ECM lines can be equivalent or disparate. For example, both the width and spacing can be about 0.1, about 0.2, about 0.25, about 5, about 0.75, about 1, about 2, about 3, about 4, about 5, about 6, about 7, about 8, about 9, about 10, about 11, about 12, about 13, about 14, about 5, about 16, about 17, about 18, about 19, or about 20 μm. In other embodiments, the width can be about 0.1, about 0.2, about 0.25, about 5, about 0.75, about 1, about 2, about 3, about 4, about 5, about 6, about 7, about 8, about 9, or about 10 μm and the spacing can be about 1, about 2, about 3, about 4, about 5, about 6, about 7, about 8, about 9, about 10, about 11, about 12, about 13, about 14, about 5, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, or about 40 μm. Conversely, the width can be about 1, about 2, about 3, about 4, about 5, about 6, about 7, about 8, about 9, about 10, about 11, about 12, about 13, about 14, about 5, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, or about 40 μm and the spacing can be about 0.1, about 0.2, about 0.25, about 5, about 0.75, about 1, about 2, about 3, about 4, about 5, about 6, about 7, about 8, about 9, or about 10 μm.

In one embodiment, e.g., in a fluidics device of the invention (described below), the width of the ECM lines is about 12, 13, 14, 15, 16, 17, 18, 19, 20, 21, 22, 23, 24, or about 25 μm and the spacing of the lines is about 0.5, 1, 1.5, 2, 2.5, or about 3 μm.

Typically the patterned ECM lines are parallel to one another, but they may also be at angles to one another at about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90°.

In one embodiment, the patterned ECM lines are parallel to one another at angles ranging from about 1° to about 90°. In another embodiment, the patterned ECM lines are parallel to one another at angles ranging from about 5° to about 45°. The angle between the patterned lines of ECM protein controls the directionality of action potential propagation. The width of the muscle tissue itself can be tapered to control the direction of action potential propagation. For example, a wide muscle tissue strip that tapers to a narrow strip will propagate an action potential from the wide to the narrow direction, but not in the opposite direction. Values and ranges intermediate to the above-recited values and ranges are also contemplated by the present invention.

In another embodiment, a muscle tissue, e.g., an MTF, is engineered using stretching of, e.g., the flexible polymer layer during tissue formation. In one embodiment, the stretching is cyclic stretching. In another embodiment, the stretching is sustained stretching. In one embodiment, the flexible polymer layer is stretched at an appropriate time after cell seeding that is based on the type(s) of cells seeded. In one embodiment, the flexible polymer layer is stretched at about minutes, hours, or days after cell seeding onto a patterned flexible polymer layer. In one embodiment, the flexible polymer layer is stretched at about 0, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or about 3.0 hours after cell seeding onto a patterned flexible polymer layer. In one embodiment, the flexible polymer layer is patterned isotropically. Stretching, therefore, results in the formation of anisotropic tissue, the anisotropy of which is in the direction of the stretch. In another embodiment, the flexible polymer layer is patterned anistropically and stretching enhances the anisotropy of the tissue formed.

In one embodiment, the flexible polymer layer is stretched using about a 0.1, 0.2, 0.3, 0.4, 0.5, 1.0, 1.5, 2.0, 2.5, 3.0, 3.5, 4, 4.5, 5.0, 5.5, or about 6.0, 6.5, 7.0, 7.5, 8.0, 8.5, 9.0, 9.5, or about 10.0 Hertz (Hz) cyclic stretch. In one embodiment, the flexible polymer layer is stretched using about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, or about 20.0% strength sustained stretch.

To attach cells, substrates are placed in culture with a cell suspension allowing the cells to settle and adhere to the surface. In the case of an adhesive surface treatment, cells bind to the material in a manner dictated by the surface chemistry. For patterned chemistry, cells respond to patterning in terms of maturation, growth and function. Examples of cell types that may be used include contractile cells, such as, but not limited to, vascular smooth muscle cells, vascular endothelial cells, myocytes (e.g., cardiac myocytes), skeletal muscle, myofibroblasts, airway smooth muscle cells and cells that will differentiate into contractile cells (e.g., stem cells, e.g., embryonic stem cells or adult stem cells, progenitor cells or satellite cells).

The term "progenitor cell" is used herein to refer to cells that have a cellular phenotype that is more primitive (e.g., is at an earlier step along a developmental pathway or progression than is a fully differentiated cell) relative to a cell which it can give rise to by differentiation. Often, progenitor cells also have significant or very high proliferative potential. Progenitor cells can give rise to multiple distinct differentiated cell types or to a single differentiated cell type, depending on the developmental pathway and on the environment in which the cells develop and differentiate.

The term "progenitor cell" is used herein synonymously with "stem cell."

The term "stem cell" as used herein, refers to an undifferentiated cell which is capable of proliferation and giving rise to more progenitor cells having the ability to generate a large number of mother cells that can in turn give rise to differentiated, or differentiable daughter cells. The daughter cells themselves can be induced to proliferate and produce progeny that subsequently differentiate into one or more mature cell types, while also retaining one or more cells with parental developmental potential. The term "stem cell" refers to a subset of progenitors that have the capacity or potential, under particular circumstances, to differentiate to a more specialized or differentiated phenotype, and which retains the capacity, under certain circumstances, to proliferate without substantially differentiating. In one embodiment, the term stem cell refers generally to a naturally occurring mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell which itself is derived from a multipotent cell, and so on. While each of these multipotent cells may be considered stem cells, the range of cell types each can give rise to may vary considerably. Some differentiated cells also have the capacity to give rise to cells of greater developmental potential. Such capacity may be natural or may be induced artificially upon treatment with various factors. In many biological instances, stem cells are also "multipotent" because they can produce progeny of more than one distinct cell type, but this is not required for "stem-ness." Self-renewal is the other classical part of the stem cell definition. In theory, self-renewal can occur by either of two major mechanisms. Stem cells may divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only. Formally, it is possible that cells that begin as stem cells might proceed toward a differentiated phenotype, but then "reverse" and re-express the stem cell phenotype, a term often referred to as "dedifferentiation" or "reprogramming" or "retrodifferentiation".

The term "embryonic stem cell" is used to refer to the pluripotent stem cells of the inner cell mass of the embryonic blastocyst (see U.S. Pat. Nos. 5,843,780, 6,200,806, the contents of which are incorporated herein by reference). Such cells can similarly be obtained from the inner cell mass of blastocysts derived from somatic cell nuclear transfer (see, for example, U.S. Pat. Nos. 5,945,577, 5,994,619, 6,235,970, which are incorporated herein by reference). The distinguishing characteristics of an embryonic stem cell define an embryonic stem cell phenotype. Accordingly, a cell has the phenotype of an embryonic stem cell if it possesses one or more of the unique characteristics of an embryonic stem cell such that that cell can be distinguished from other cells. Exemplary distinguishing embryonic stem cell characteristics include, without limitation, gene expression profile, proliferative capacity, differentiation capacity, karyotype, responsiveness to particular culture conditions, and the like.

The term "adult stem cell" or "ASC" is used to refer to any multipotent stem cell derived from non-embryonic tissue, including fetal, juvenile, and adult tissue. Stem cells have been isolated from a wide variety of adult tissues including blood, bone marrow, brain, olfactory epithelium, skin, pancreas, skeletal muscle, and cardiac muscle. Each of these stem cells can be characterized based on gene expression, factor responsiveness, and morphology in culture. Exemplary adult stem cells include neural stem cells, neural crest stem cells, mesenchymal stem cells, hematopoietic stem cells, and pancreatic stem cells.

In one embodiment, progenitor cells suitable for use in the claimed devices and methods are Committed Ventricular Progenitor (CVP) cells as described in PCT Application No. PCT/US09/060224, entitled "Tissue Engineered Myocardium and Methods of Productions and Uses Thereof", filed Sep. 28, 2009, the entire contents of which are incorporated herein by reference.

The cells on the substrates are cultured in an incubator under physiologic conditions (e.g., at 37° C.) until the cells form a two-dimensional (2D) tissue (i.e., a layer of cells that is less than about 200 microns thick, or, in particular embodiments, less than about 100 microns thick, less than about 50 microns thick, or even just a monolayer of cells), the anisotropy or isotropy of which is determined by the engineered surface chemistry.

Any appropriate cell culture method may be used to establish the tissue on the polymer surface. The seeding density of the cells will vary depending on the cell size and cell type, but can easily be determined by methods known in the art. In one embodiment, cardiac myocytes are seeded at a density of between about $1 \times 10^5$ to about $6 \times 10^5$ cells/cm$^2$, or at a density of about $1 \times 10^4$, about $2 \times 10^4$, about $3 \times 10^4$, about $4 \times 10^4$, about $5 \times 10^4$, about $6 \times 10^4$, about $7 \times 10^4$, about $8 \times 10^4$, about $9 \times 10^4$, about $1 \times 10^5$, about $1.5 \times 10^5$, about $2 \times 10^5$, about $2.5 \times 10^5$, about $3 \times 10^5$, about $3.5 \times 10^5$, about $4 \times 10^5$, about $4.5 \times 10^5$, about $5 \times 10^5$, about $5.5 \times 10^5$, about $6 \times 10^5$, about $6.5 \times 10^5$, about $7 \times 10^5$, about $7.5 \times 10^5$, about $8 \times 10^5$, about $8.5 \times 10^5$, about $9 \times 10^5$, about $9.5 \times 10^5$, about $1 \times 10^6$, about $1.5 \times 10^6$, about $2 \times 10^6$, about $2.5 \times 10^6$, about $3 \times 10^6$, about $3.5 \times 10^6$, about $4 \times 10^6$, about $4.5 \times 10^6$, about $5 \times 10^6$, about $5.5 \times 10^6$, about $6 \times 10^6$, about $6.5 \times 10^6$, about $7 \times 10^6$, about $7.5 \times 10^6$, about $8 \times 10^6$, about $8.5 \times 10^6$, about $9 \times 10^6$, or about $9.5 \times 10^6$. Values and ranges intermediate to the above-recited values and ranges are also contemplated by the present invention.

In one embodiment, cardiac myocytes are co-cultured with neurons to prepare innervated engineered tissue comprising pacemaking cells, and/or to accelerate the maturation of the cultured cells as described in U.S. application Ser. No. 13/580,191, filed Aug. 21, 2012, the entire contents of which are incorporated herein by reference.

In one embodiment, a specific shape (e.g., a rectangular strip) is cut in the muscle tissue using a scalpel, razor blade, punch, die or laser. If present, the sacrificial layer is then dissolved or actuated to release the flexible polymer from the rigid base (e.g., by dropping the temperature below 35° C.); and the cut-out shape then floats free or is gently peeled off. The bending stiffness of the muscle tissues along any given axis, much like a cantilever, increases with the elastic modulus, thickness and width while decreasing with length.

Suitable support structures for embodiments of the present invention include, for example, Petri dishes, cover-slips (circular or rectangular), strips of glass, glass slides, multi-well plates, microfluidic chambers, and microfluidic devices. The support structure is ideally biologically inert, it has low friction with the films and it does not interact (e.g., chemically) with the films. Examples of materials that can be used to form the support structure include polystyrene, polycarbonate, polytetrafluoroethylene (PTFE), polyethylene terephthalate, quartz, silicon (e.g., silicon wafers) and glass. In one embodiment, the support structure is transparent. In another embodiment, the support structure is opaque (e.g., light-absorbing). In one embodiment, a portion of the base layer is transparent (i.e., a portion underneath a portion of the muscle tissue) and the remaining portion is opaque. In yet another embodiment, the base layer is translucent.

In one embodiment the base layer and the solid substrate are fabricated from the same material. In another embodiment, the base layer and the solid support are fabricated from different materials.

Examples of suitable materials for a co-culture device include, but are not limited to, tissue culture polystyrene, acid washed glass, extracellular matrix (e.g., collagen, fibronectin, fibrin, laminin) coated glass or polymer (e.g., PET, nylon), poly L-lysine coated glass or polymer.

In the embodiments of the invention in which the muscle tissues are attached to the solid support structure indirectly, via a post (as in FIGS. 1-3), the posts may be formed from a rigid material, such as polystyrene, stainless steel, polytetrafluoroethylene (PTFE) or a cactus needle. The post may also be adhesive to the thin film. In some embodiments, the post and film are mechanically adhesive (e.g., the film and post are clipped to each other).

Figure 3:
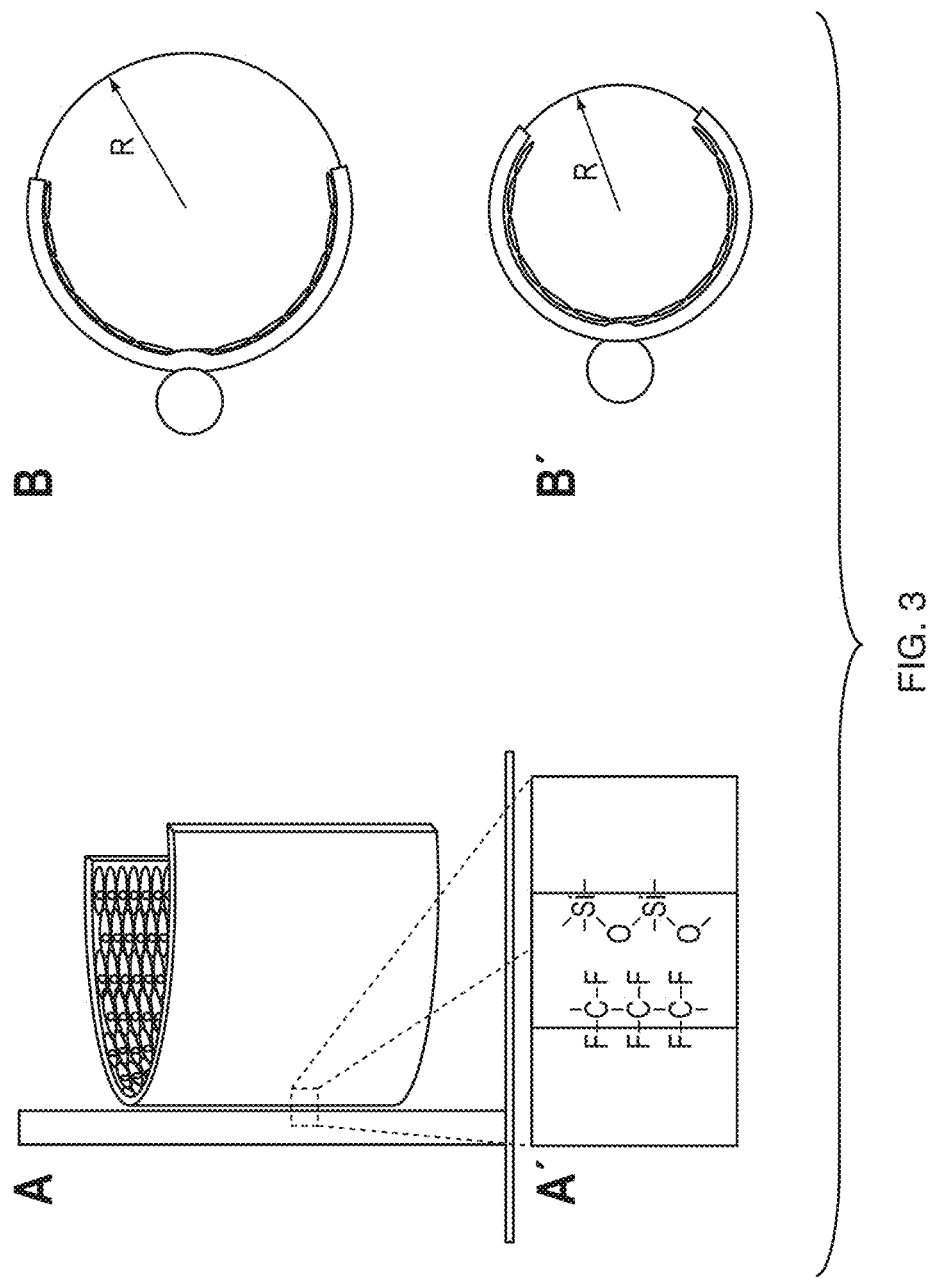
FIG. 3 provides illustrations of a thin film adhered to a post. (A) depicts the embodiment wherein the polymer side of thin film adheres to post. (A') depicts the embodiment wherein a PDMS thin film adheres to a PTFE post through hydrophobic-hydrophonic interaction. (B, B') depicts the embodiment wherein a change in the radius of curvature (R) is used to calculate a change in stress in a cell layer.

In other embodiments, the post and film are chemically adhesive. For example, the post can be coated with adhesive glue. Alternatively, the post is coated or formed from a material that interacts with the flexible polymer layer of the film, if present. For example, as shown in FIG. 3, the PDMS of the flexible polymer layer of the thin film adheres to a PTFE post through a hydrophobic-hydrophobic interaction. In other embodiments, the post may be coated with a material (e.g., poly L-lysine, collagen, fibronectin, fibrin, laminin) that binds to the cell layer of the thin film.

The appended Figures depict various embodiments of the devices of the present invention. For example, FIG. 1 depicts a device of the invention in which a homogeneous cell population is used. As shown in FIGS. 1A and 1B, schematic perspective and top views respectively, the system includes a solid support structure, such as a Petri dish, with posts affixed to it and substantially perpendicular to the base of the solid support structure. Thin films are adhered to the posts. A photograph of a device according to this embodiment is shown in FIG. 1C.

Figure 2:
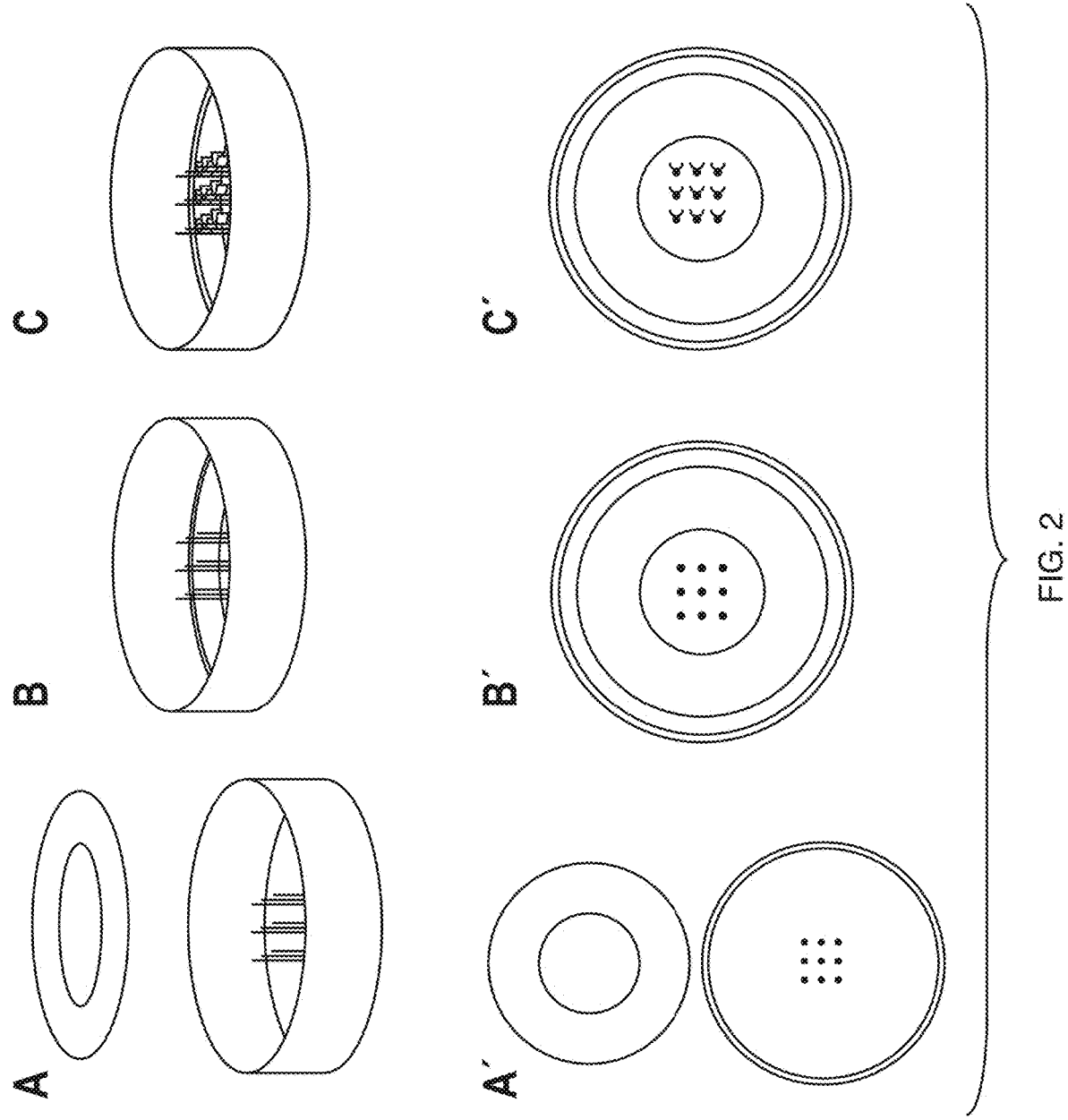
FIG. 2 depicts the system of FIG. 1 that further includes a co-culture slide. (A, A') depicts the embodiment wherein a co-culture slide is cultured separate from the device and (B, B') inserted into the device prior to performing the methods of the invention. (C, C') depicts the embodiment wherein the thin films are adhered to posts parallel to the dish base for optimal viewing.

FIG. 2 depicts a device of FIG. 1 that further includes a co-culture device, e.g., slide, that can be inserted into the assay dish. As shown in FIG. 2, the system includes a ring on which additional cells can be seeded, for the study of cell-cell interactions such as, for example, paracrine signaling. Cell-cell interactions, such as paracrine signaling can be studied by using films cultured with different cell types (e.g., vascular smooth muscle and cardiac myocytes) together. The use of thin films with different cell types together with a co-culture device allows for studies of three or more cell types.

Figure 4:
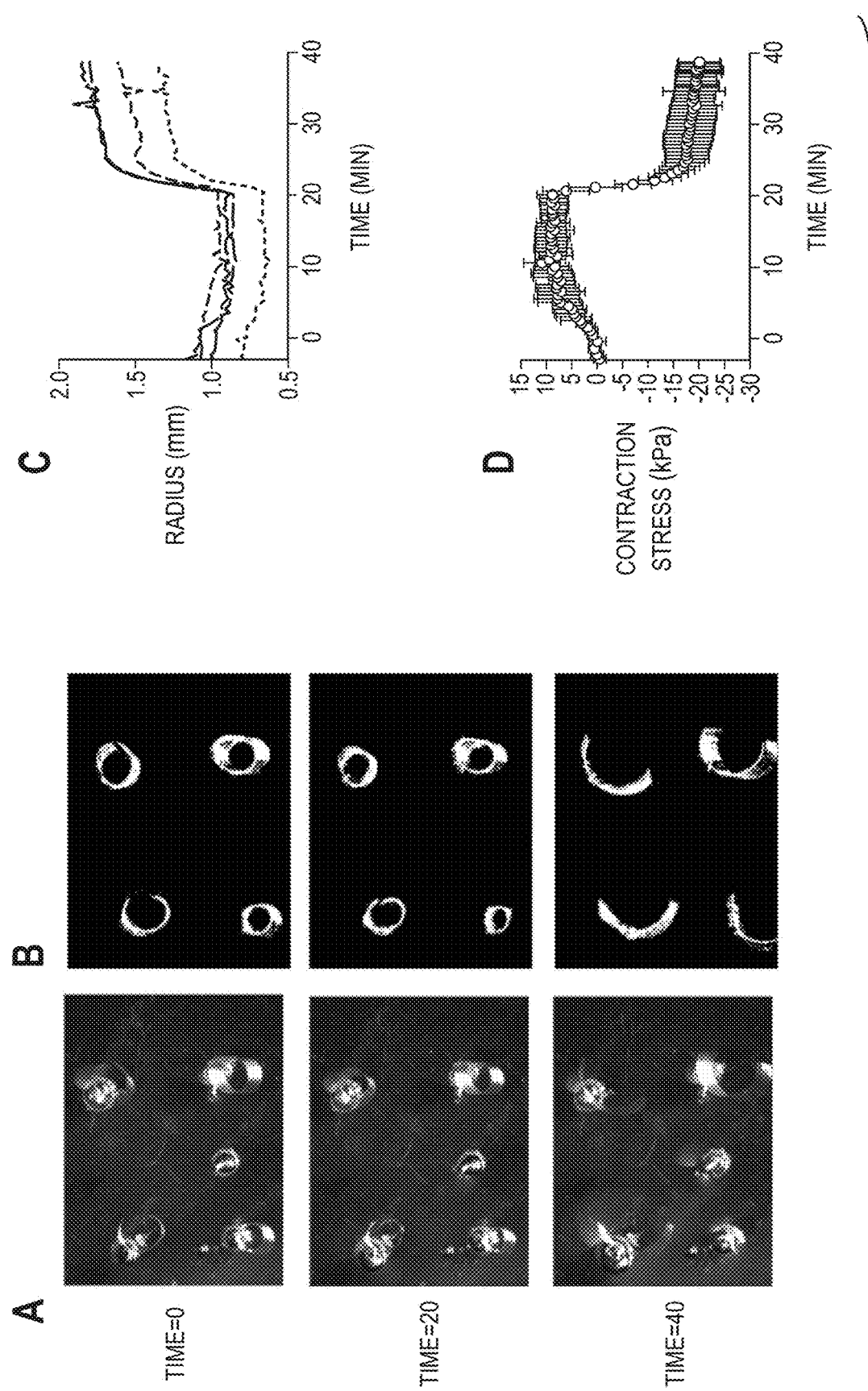
FIG. 4 provides images and charts of the system of FIG. 1 using rectangular-shaped muscular thin films (MTFs) with vascular smooth muscle anisotropically aligned along its length, and the deformation of the muscular thin films with time after treatment with endothelin-1. (A) depicts stereo microscopic images of polymeric thin films, seeded with vascular smooth muscle, adhered to posts. (B) depicts threshold images of thin films with films isolated from background. (C) depicts the measured change in radius of curvature with time. (D) depicts muscle stress necessary to induce change in curvature.

The devices of FIGS. 1 and 2 can be used as follows: When a co-culture device with secondary cells (e.g., aortic endothelial cells) is used, it is placed in the device, e.g., dish, in a buffered medium. Thin films are prepared and cut into strips, as discussed below or as described in PCT Publication No. WO 2008/051265. The strips are transferred to the device and are adhered to the posts such that the plane of primary curvature is parallel with the plane of the device, e.g., Petri dish base. A stimulus is applied to the films to cause stress in the cell layer. The curvature of the films is recorded and cell stress is calculated. A fluid perfusion system can be used to wash out test compounds that are being screened in a high throughput assay or to refresh the culture medium. A typical experiment using the device of FIG. 1 is shown in FIG. 4, where rectangular-shaped muscular thin films with vascular smooth muscle anisotropically aligned along their lengths were used, and the deformation of the muscular thin films with time after treatment with endothelin-1 was measured.

Figure 5:
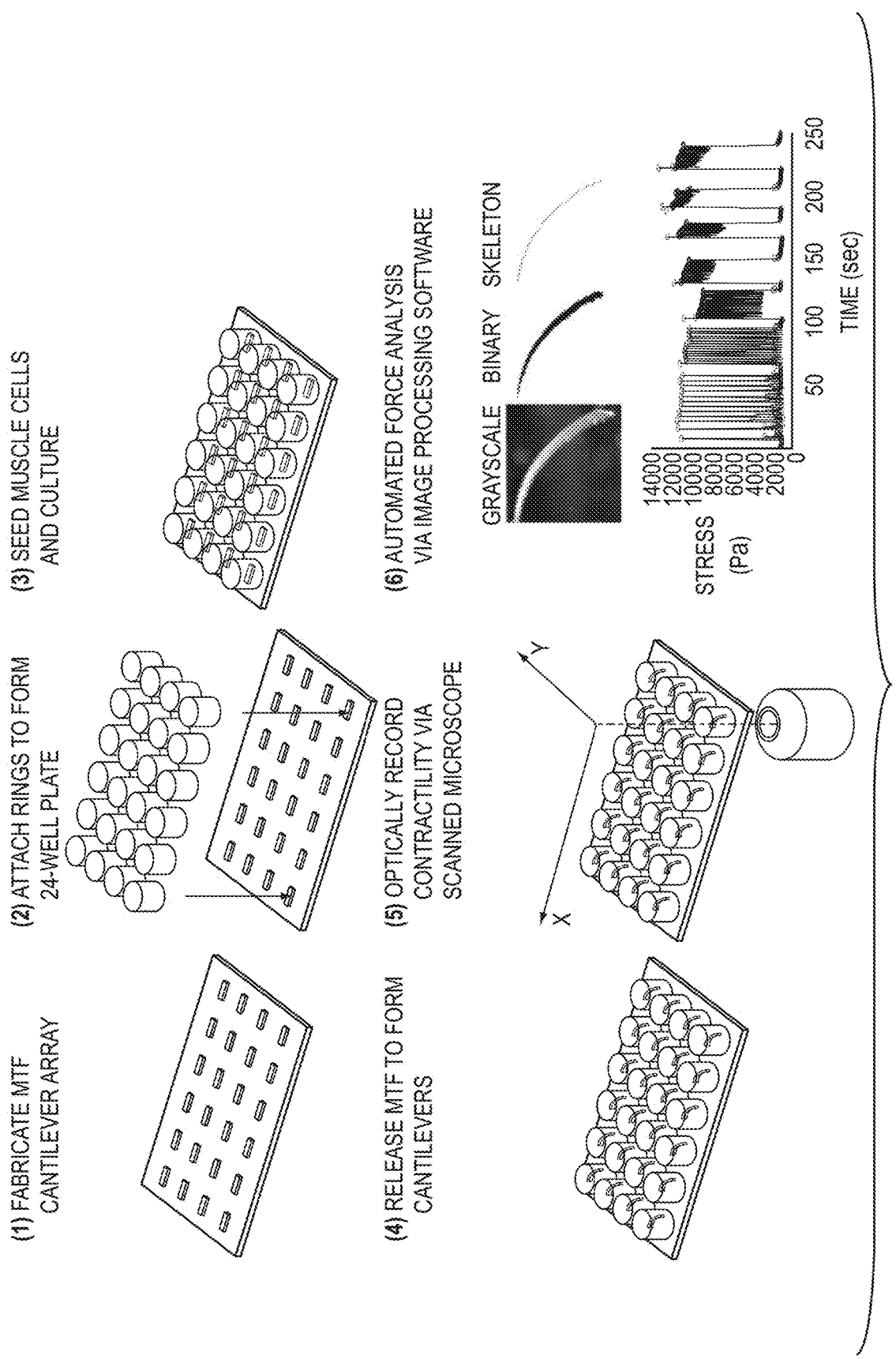
FIG. 5 schematically depicts the fabrication and use of a multi-well based device of the invention.
Figure 6:
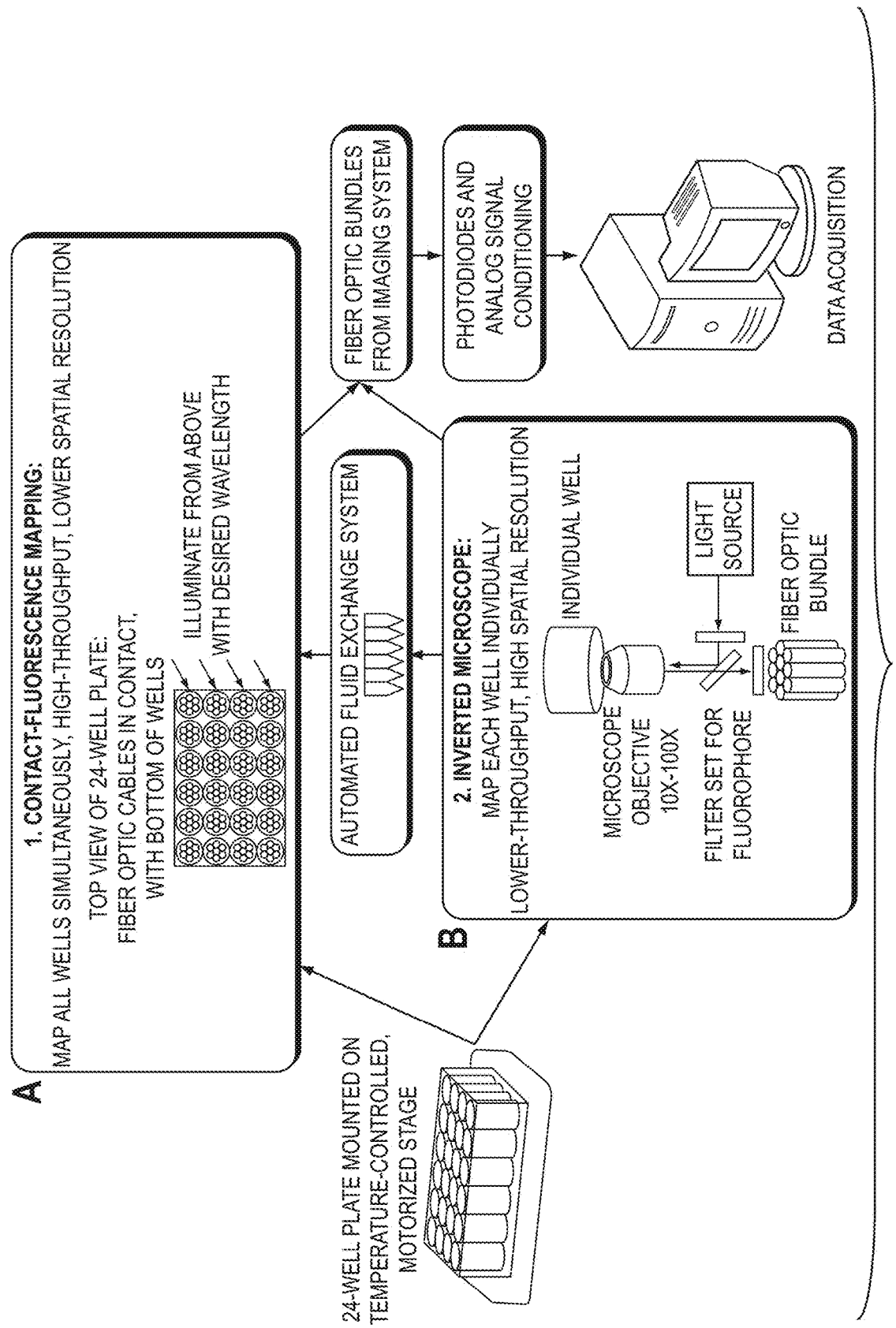
FIG. 6 graphically depicts two approaches for imaging MTFs in the high-throughput methods described herein.

FIG. 5 schematically depicts one embodiment for the fabrication and use of a multi-well based device of the invention. According to this embodiment, an array of thin strips is created on a solid support structure. Rings are placed on the solid support structure creating a multi-well plate (e.g., about 8-, about 12-, about 16-, about 20-, about 24-, about 28-, about 32-about 36-, about 40, about 44, about 48-, about 96-, about 192-, about 384-wells) and isolating the strips. Cells are then seeded and cultured onto the strips to form tissue structures as described below or as described in PCT Publication No. WO 2008/051265. In one embodiment, cells are cultured in the presence of a fluorophore or fluorescent beads. One end of the strips is optionally detached from the solid support structure and released to form structures, e.g., cantilevers, which are free to deform when the tissue structures contract. The deformation (i.e., contractility) of the MTFs may be recorded, e.g., as depicted in FIG. 6. In the embodiment depicted in FIG. 6, contractility may be observed (and optionally recorded) using a microscope, which looks at one strip at a time while it scans across multiple samples (see FIG. 6B). In one embodiment of the invention, multiple strips are observed simultaneously (see FIG. 6A). Optionally, a lens is integrated into the platform. Changes in the curvature of the films are observed and the optical image is converted to a numerical value that corresponds to the curvature of the film. In one embodiment, a movie of muscle tissue contractions in a multi-well dish is acquired (e.g., images are obtained in series). Images are processed and a mechanical analysis is optionally carried out to evaluate contractility. The output may be traction as a function of standard metrics such as peak systolic stress, peak upstroke power, upstroke time, and relaxation time.

Alternative ways of measuring bending of muscle tissues include, e.g., (i) using a laser bounced off of the engineered muscle tissue to record movement, (ii) using an integrated piezoelectric film in the muscle tissue and recording a change in voltage during bending, (iii) integrating magnetic particles in the muscle tissue and measuring the change in magnetic field during bending, (iv) placing a lens in the bottom of each well and simultaneously projecting multiple wells onto a single detector (e.g., camera, CCD or CMOS) at one time, (v) using a single capture device to sequentially record each well (see, e.g., FIG. 6(2)), e.g., the capture device is placed on an automated motorized stage. Finally, the measured bending information (e.g., digital image or voltage) is converted into force, frequency and other contractility metrics.

Figure 7A:
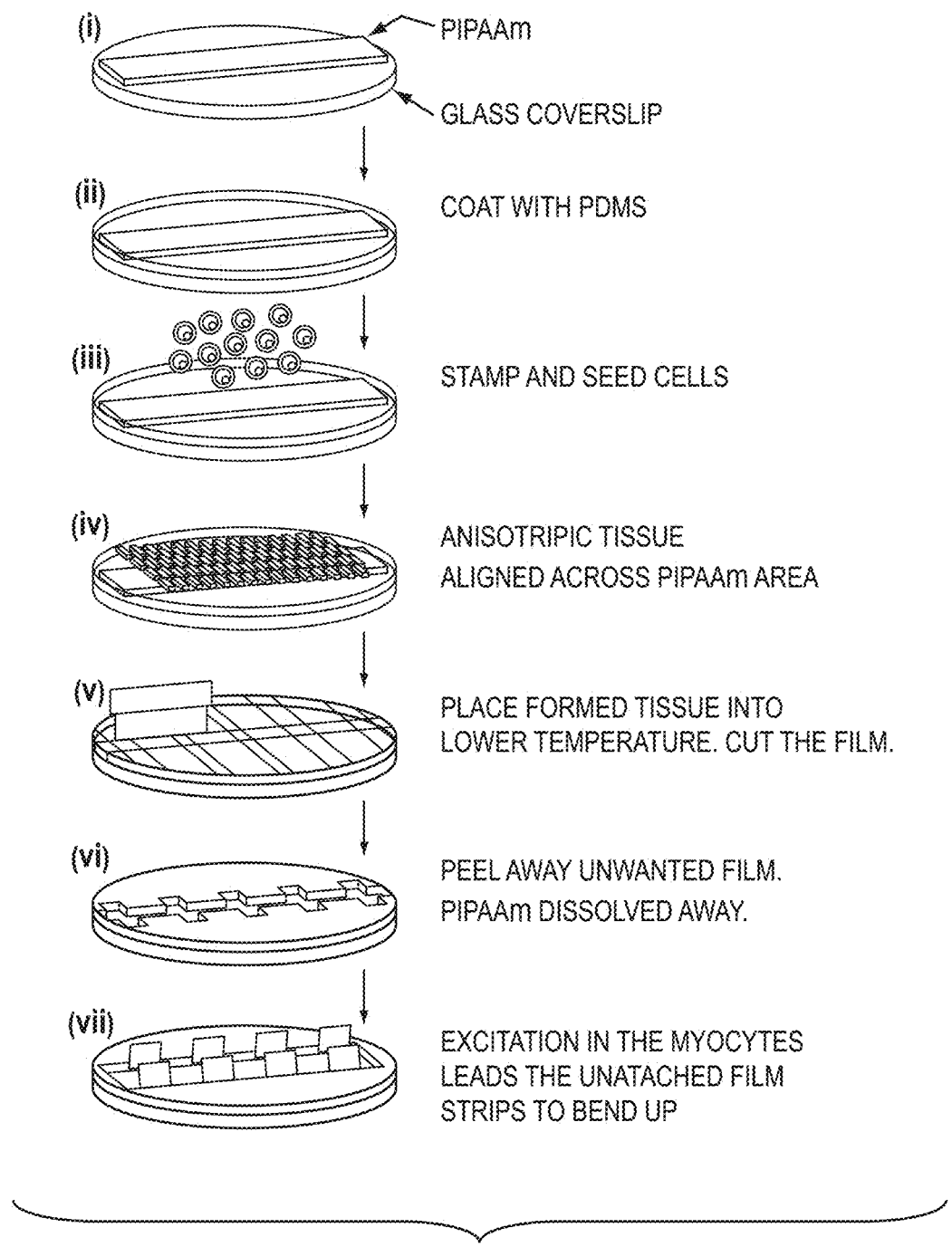
FIG. 7A schematically depicts one embodiment of the fabrication and use of a horizontal MTF device of the present invention.
Figure 7B:
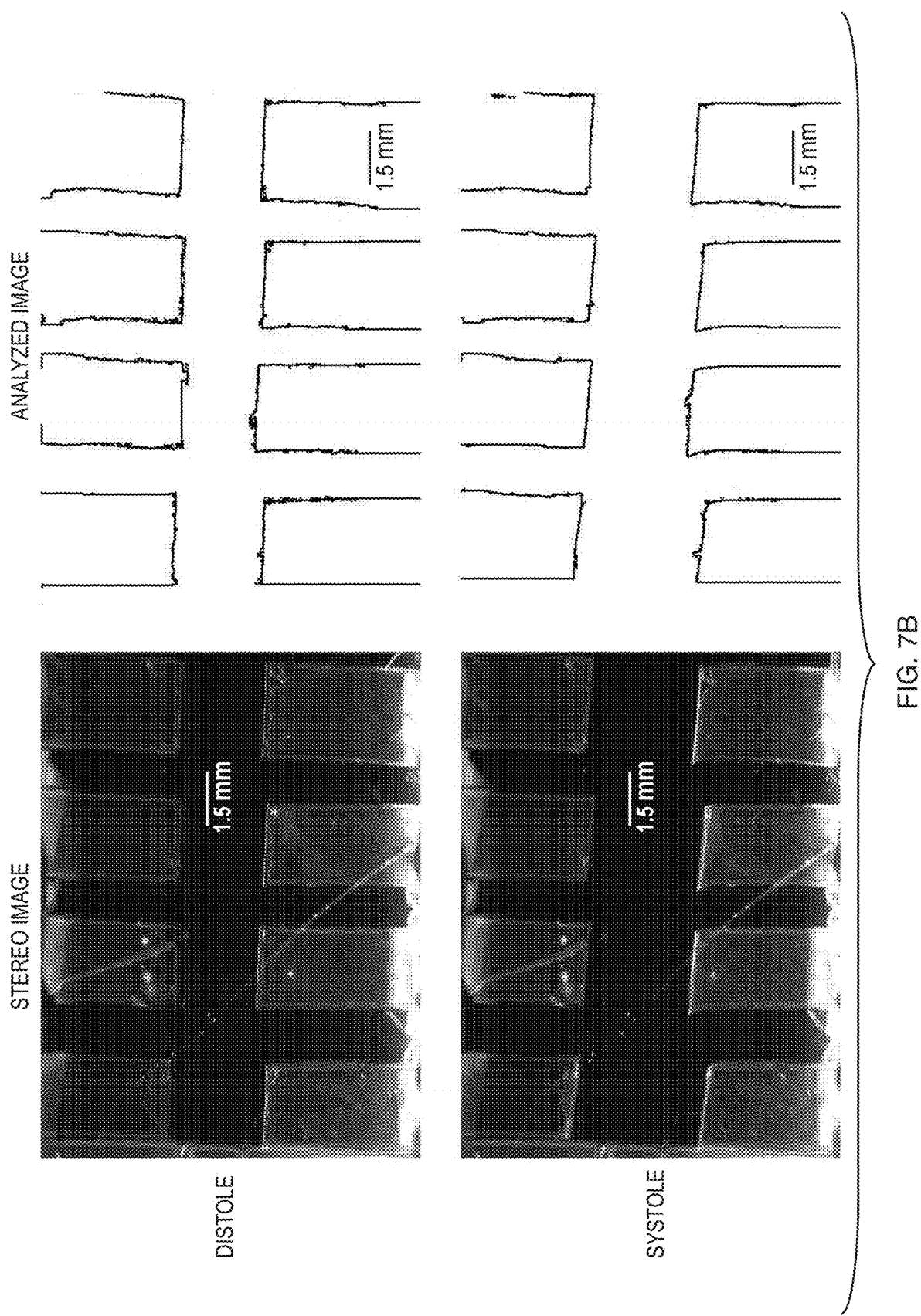
FIG. 7B is a photograph and image processing of the same device.
Figure 7C:
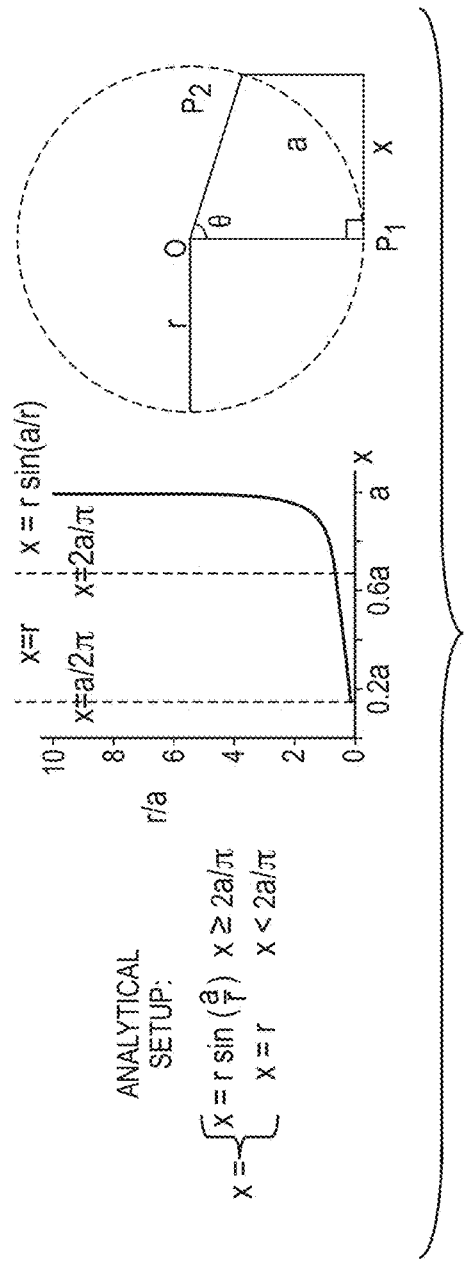
FIGS. 7C and 7D depict the calculation of the radius of curvature of the MTFs in the device depicted in FIG. 7A.

In another embodiment, as depicted in FIGS. 7A, 7B, and 7C, a muscle tissue device is constructed horizontally rather than vertically such that handling of the muscle tissue is not necessary allowing for increased throughput of muscle tissues production. More specifically and similar to the muscle tissue, e.g., MTF fabrication process described in U.S. Patent Publication No. 2009/0317852, a substrate or device is fabricated as a rigid base material which is coated partially, i.e., all of the edges of the base material are not covered with a sacrificial polymer layer; a flexible polymer layer is temporarily bonded to the rigid base material via the sacrificial polymer layer, and an engineered surface chemistry is provided on the flexible polymer layer to enhance or inhibit cell and/or protein adhesion. Cells are seeded onto the flexible polymer layer and cultured to form a tissue. The formed tissue is then placed at a lower temperature (e.g., 35 C°).

In order to create the horizontal muscle tissues, e.g., MTFs and/or hydrogel engineered muscle tissues, sections of the flexible polymer layer and/or tissue can be cut and removed such that strips of the tissue (and flexible film if present), remain secured at their base to the base material and act as a hinge. This method allows the muscle tissues to curve upward off the base layer, i.e., to curve upward from the viewing (horizontal plane), as compared to the muscle tissues described above in which the muscle tissue bends in the viewing plane) when stimulated to contract (see, e.g., FIGS. 1-3). In this embodiment, individual muscle tissues (e.g., 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more muscle tissues) can be prepared on a single solid support structure, e.g., a glass cover slip (round or rectangular), a Petri dish, a glass slide, strips of glass, or a multi-well plate. The functional properties of these muscle tissues, e.g., the contractility of these muscle tissues, may be determined as described above for a vertical muscle tissues.

Figure 8:
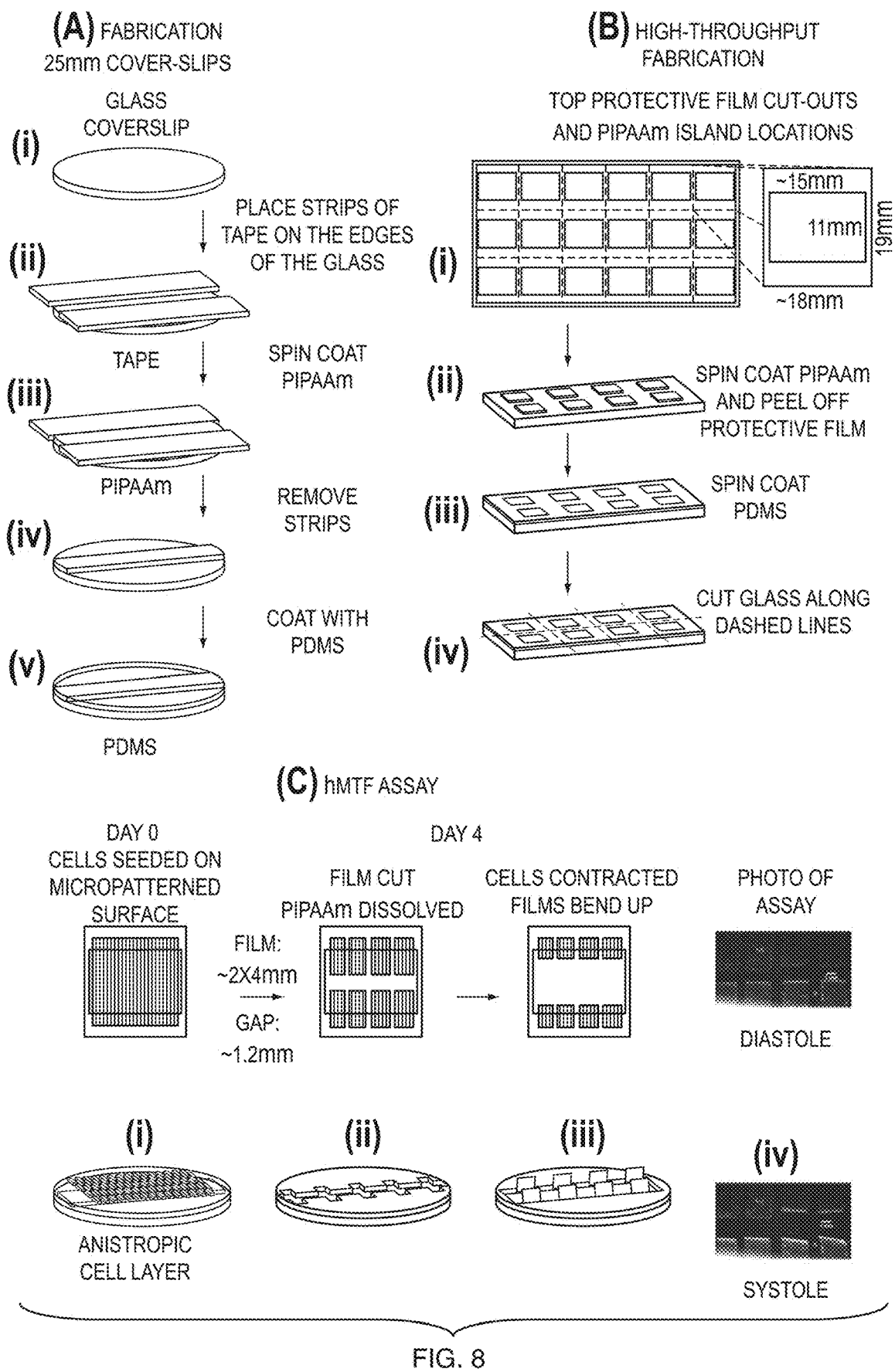
FIG. 8 schematically depicts the contrast between assaying contractility of an MTF using a large, rectangular glass comprising a horizontal MTF versus a round cover-slip comprising a horizontal MTF. (A) Fabrication of a horizontal MTF using a round cover-slip; (B) Fabrication of a horizontal MTF using a rectangular cover-slip (higher throughput); (C) Contrast of running a contractility assay with a round cover-slip versus a square cover-slip. Although the manual fabrication of horizontal MTF is more efficient using square cover-slips, round cover-slips are often more compatible with commercially available microscope equipment.

In another embodiment, horizontal muscle tissues, e.g., MTFs, are fabricated as depicted in FIGS. 8A and 8B. More specifically, a protective film, e.g., static vinyl sheet or tape, e.g., adhesive tape, is applied to one or more portions of a rigid base material in order to prevent adherence of a sacrificial polymer to the rigid base material. The protective film may be applied to the rigid base material by, e.g., contacting the rigid base material with a liquid prior to applying the protective film to generate a liquid interface (e.g., any solvent that does not leave behind a residue on the rigid base material, e.g., ethanol) between the rigid base material and the protective film, and removing the excess liquid. In one embodiment, one or more portions of the top of the rigid base material (i.e., where the horizontal muscle tissue will be formed) is coated with a protective film. In another embodiment, one or more portions, or all of the bottom (i.e., where the horizontal muscle tissue will not be formed) of the rigid base material is coated with a protective film. In another embodiment, one or more portions of the top of the rigid base material and one or more portions or all of the bottom of the rigid base material are coated with a protective film.

In one embodiment, one or more sections of the protective film on the top surface of the rigid base material are cut and removed, thereby creating islands of rigid base material. The rigid base material partially coated with the protective film is then coated with a sacrificial polymer layer and the remaining protective film on the top of the rigid base material is removed. Subsequently, a flexible polymer layer is temporarily bonded to the rigid base material via the sacrificial polymer layer. If used, the bottom protective layer is then removed. Next, an engineered surface chemistry is provided on the flexible polymer layer to enhance or inhibit cell and/or protein adhesion, cells are seeded onto the flexible polymer layer and cultured to form a tissue, as described above. The formed tissue is then placed at a lower temperature (e.g., 35 C°) to dissolve the sacrificial polymer layer and sections of the flexible polymer layer (corresponding to the islands) can be cut to create the horizontal muscle tissues.

Figure 9:
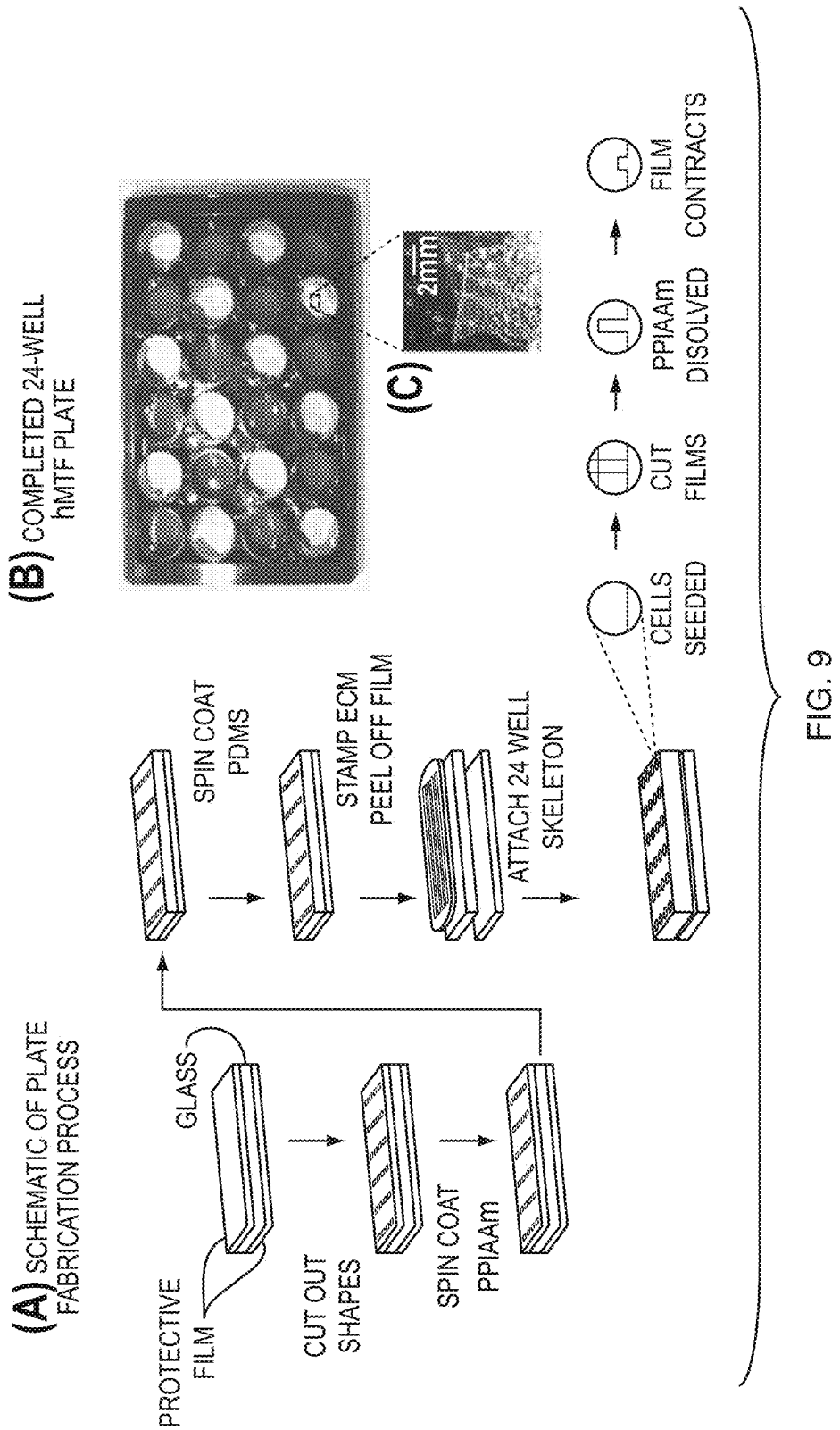
FIG. 9A schematically depicts an embodiment of the fabrication of a horizontal MTF device using the protective film procedure in a multi-well dish with a zoomed in view of the film inside a well (not to scale).
FIG. 9B is a photo of a 24-well plate containing a checkered pattern of buffer with phenol red (grey) and without phenol red (white) used to detect leaks between wells.
FIG. 9C is a photo of a muscle thin film inside of a well of the 24-well plate depicted in FIG. 9B.

In one embodiment, the methods for fabricating a horizontal muscle tissue (using a protective film described above), further comprise attaching a multi-well plate skeleton to the rigid base material subsequent to patterning the flexible polymer layer with an engineered surface chemistry and prior to cell seeding (see, e.g., FIG. 9A).

In one embodiment, a device comprising a horizontal muscle tissue, e.g., an MTF and/or hydrogel engineered muscle tissue, and a multi-well plate further comprises a photodiode array (see, e.g., FIG. 19).

In one embodiment, as described above for a vertical muscle tissue, the solid support structure may further comprise an optical signal capture device and an image processing software to calculate change in an optical signal. The optical signal capture device may further include fiber optic cables in contact with the device and/or a computer processor in contact with the device.

In another embodiment, a piezoresistive, a piezoelectric, or a strain sensor is embedded in the flexible polymer layer and/or hydrogel layer and, thus, the device may further comprises cable in contact with the device and/or a computer processor in contact with the device.

In one embodiment, an electrode is in contact with the device.

Figure 10:
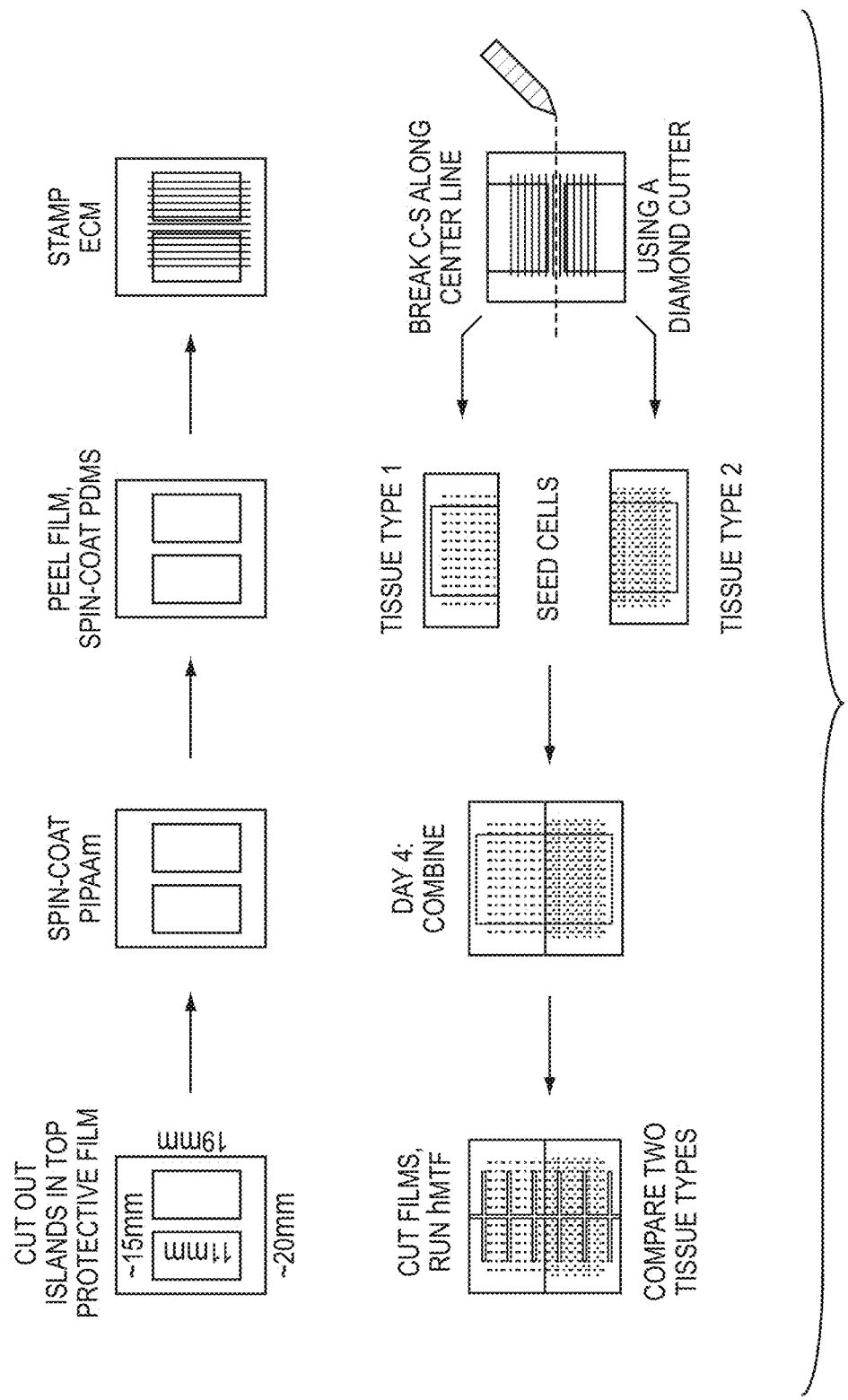
FIG. 10 schematically depicts one embodiment of the fabrication of a two tissue type horizontal MTF device useful for a side-by-side assay.
Figure 11:
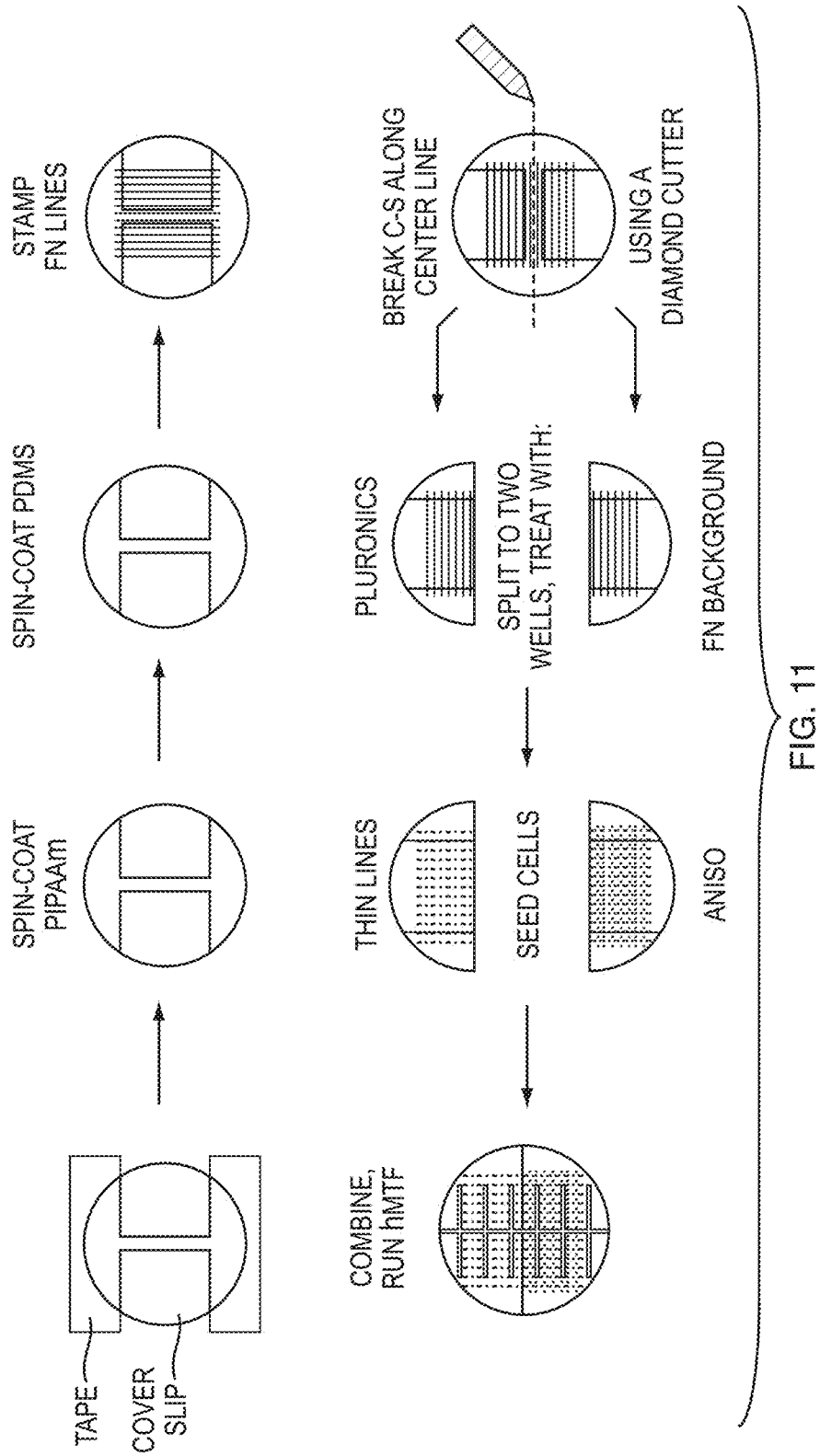
FIG. 11 schematically depicts another embodiment of the fabrication of a two tissue type horizontal MTF device useful for a side-by-side assay.

In certain embodiments of the invention, prior to patterning the flexible polymer layer and/or hydrogel layer with an engineered surface chemistry, the rigid base material coated with a sacrificial polymer layer and a flexible polymer layer (or hydrogel layer), are divided, e.g., are cut, into portions, i.e., separate, individual devices (see, FIGS. 10 and 11). Such devices are useful for "side-by-side" assays that can be used, e.g., to qualitatively compare contractions of two tissue types, to compare the effect of one tissue response in proximity to another tissue, to compare biomechanical measurements of myocyte contraction properties, e.g., in response to various mechanical or chemical stimuli, to compare the effect of various patterning on tissue contractility, to compare different types of cells, or as an appropriate control. In other embodiments, the device is divided into individual devices prior to cell seeding and subsequent to patterning the flexible polymer layer with an engineered surface chemistry.

In one embodiment, devices that are divided subsequent to patterning the flexible polymer layer and/or hydrogel with an engineered surface chemistry may be further contacted with the same or different engineered surface chemistry to elicit or inhibit specific cell growth and/or function. In one embodiment, an individual device is combined with (e.g., placed in physical proximity to) one or more other individual devices subsequent to cell seeding such that the two devices share the same media and/or test compound and/or can send a paracrine signal. In one embodiment, two or more devices placed in physical proximity to each other are separated by a membrane which allows molecules of a certain size to pass through. In another embodiment, two or more devices are combined by a channel such that they share the same media and/or test compound but cannot send a paracrine signal.

In another embodiment, the invention provides a fluidics device, e.g., a millifluidics or microfluidics device, comprising a solid support structure which comprises a plurality of muscle tissue, e.g., MTFs and/or hydrogel engineered muscle tissues (e.g., the device comprises 1, 2, 3, 4, or 5 fluidic chambers each comprising a muscle tissue, the device comprises 1, 2, 3, 4, or 5 fluidic chambers each comprising a plurality of muscle tissues, the device comprises a plurality of fluidic chambers each comprising a plurality of muscle tissues, the device comprises a plurality of fluidic chambers each comprising a muscle tissue), such as depicted in FIGS. 13, 14, 16, 18B, 22, 23, 25-29, 36, 39, 40, 41-43, and 45, and described in, for example, PCT Publication Nos. WO 2010/042284, WO 2007/044888, and WO 2010/041230, the entire contents of each of which are incorporated herein by reference.

In one embodiment, a plurality of fluidic chambers, e.g., millifluidic or microfluidic chambers, comprising a muscle tissue is operably connected to two or more inlet channels each comprising a valve, such as described in, for example, WO 2007/044888, to regulate flow, and two or more outlet channels.

In one embodiment, the two or more inlet channels comprise one or more mixing chambers (a section of the inlet channel that generates turbidity). Such devices may have 2-1002 chambers comprising a muscle tissue, and 2, 3, 4, 5, 6, 7, 8, 9, or 10 inlet channels, each with a valve. Such devices may have from 1-10,000 mixing chambers. Such devices are useful for generating concentration gradients of a test compound to perform a dose response assay with the test compound. The number of concentrations of the test compound that may be produced in such a device is dependent on the number of mixing chambers.

In another embodiment, the plurality of fluidic chambers comprising a muscle tissue is operably connected to one or more inlet ports and does not comprise a mixing chamber. Such devices may comprise 1-1000 inlet ports and 1-1000 chambers comprising a muscle tissue. Such devices are also useful for performing a dose response assay with a test compound, however the various drug concentrations must be pre-mixed and introduced into an inlet port separately.

In one embodiment, the fluidics devices of the invention further optionally comprise one or more (e.g., 1, 2, 3, 4, 5, 6, 7, 8, 9, or 10) collection ports.

Fluid may be moved through the fluidics devices by any suitable means, such as electrochemical or pressure-driven means.

A fluidic chamber and a fluidic channel may be fabricated into one or more materials including but not limited to, Polydimethylsiloxane (PDMS), polyurethanes, other elastomers, thermoplastics (e.g. polymethyl methacrylate (PMMA), polyethylene, polyethylene terephthalate, polystyrene), epoxies and other thermosets, silicon, silicon dioxide, and indium tin oxide (ITO).

Any suitable method may be used to fabricate a fluidic channel and/or chamber, such as, for example, micromachining, injection molding, laser etching, laser cutting, and soft lithography. In one embodiment, an electrode is fabricated into a chamber using a non-reactive metal, such as, platinum, gold, silver chloride, and indium tin oxide.

A muscle tissue suitable for use in a fluidics device may be fabricated as described herein and/or in, for example U.S. Patent Publication No. 2009/0317852-A1, and cut into suitably sized strips which can form the muscle tissue strips used in the devices and methods of the invention. Alternatively, horizontal muscle tissues may be fabricated as described herein.

Cells may be seeded prior to assembly of the polymeric thin film and/or hydrogel into a fluidics device and/or may be seeded subsequent to full assembly of the device. In addition, a hydrogel and/or polymeric thin film may be pre-fabricated into a chamber of the fluidics device, or may be added to a chamber of the device after the device is fabricated.

The benefits of a fluidics device for use in the methods of the invention include, for example, creation of a microenvironment that more closely resembles an in vivo fluidic microenvironment, increasing the number of assays that may be performed simultaneously while decreasing the amount of test compound required, ability to create a wide range of test compound concentrations for simultaneous assaying, and the ability to maintain muscle tissues in culture for up to one month in culture (depending on the tissue type).

In yet other embodiments of the invention, muscle tissues, e.g., muscle tissue strips, may be free standing. In one embodiment, muscle tissues are separated from the well edges by 1-2 lengths of the muscle tissue.

In the embodiments of the invention where the solid support structure is a multi-well plate, each well may contain one muscle tissue, two muscle tissues, or multiple muscle tissues.

In one embodiment, nanoparticles and/or fluorescent beads, e.g., fluorospheres, are mixed with the hydrogel prior to cross-linking and or with the flexible polymer layer prior to spin-coating the flexible polymer layer onto the sacrificial polymer layer. The addition of such beads may enhance data capture. For example, in embodiments in which the muscle tissue strips are free standing and/or substantially all of a muscle tissue strip comprising the hydrogel is attached to the solid support structure (e.g., in embodiments in which contractility is measured as mechanical deformation) contractility is measured as mechanical deformation of the particles using, e.g., an optical system. In some embodiments, when nanoparticles and/or fluorescent beads, e.g., fluorospheres, are not mixed with the hydrogel prior to cross-linking and or with the flexible polymer layer prior to spin-coating the flexible polymer layer onto the sacrificial polymer layer and the muscle tissue strips are free standing and/or substantially all of the strip is attached to the solid support structure, contractility is measured as mechanical deformation by measuring the deformation of the boundaries of the tissue strips, e.g., using an optical system.

In certain embodiments of the invention, e.g., for evaluation of electrophysiological activities, cells are cultured in the presence of a fluorophor such as a voltage-sensitive dye or an ion-sensitive dye. For example, the voltage-sensitive dye is an electrochromic dye such as a styryl dye or a merocyanine dye. Exemplary electrochromic dyes include RH-421 or di-4-ANEPPS. Ion-sensitive, e.g., calcium sensitive dyes, include aequorin, Fluo3, and Rhod2. For simultaneous measurements of action potentials and intracellular calcium, the following exemplary dye pairs are used: di-2-ANEPEQ and calcium green; di-4-ANEPPS and Indo-1; di-4-ANEPPS and Fluo-4; RH237 and Rhod2; and, RH-237 and Fluo-3/4.

In such embodiments, the device includes muscle tissues grown in multi-well, e.g., 2-8-, 12-, 16-, 20-, 24-, 28-, 32-36-, 40, 44, 48-, 96-, 192-, 384-, 798-, or 1536-well, plates prepared as described herein. An inverted microscope or contact-fluorescence imaging system with temperature-controlled, humidity-controlled motorized may be used to monitor muscle activity, e.g., electrophysiological changes, such as action potentials and/or intracellular calcium transients. An integrated fluid-handling system may also be used to apply/exchange fluorophores and test compounds, and a microfluidics chamber may be used for simulated drug delivery. The fluidics chamber simulates microvasculature to mimic the manner in which a compound/drug contacts a target muscle tissue comprising, e.g., cardiomyocytes. For example, a muscle tissue may respond differently to a concentration gradient or different modes of administration. A significant advantage of the devices and systems described herein is that system for measuring contractility, e.g., an optical mapping system described supra and depicted in FIG. 6) permits detection of such gradient effects, whereas earlier systems, e.g., single cell patch clamp studies, cannot measure gradient effects on a cell population.

Appropriate light source and filter sets may be chosen for each desired fluorophore based on the wavelength of the excitation light and fluoresced light of the fluorophore. Integration of excitation wavelength-switching or an additional detector permits ratiometric calcium imaging. For this purpose, exemplary fluorophores include Fura-2 and Indo-1 or Fluo-3 and Fura Red. For example, excitation and emission filters at 515±5 and >695 nm, respectively, are used to measure action potentials with di-4-ANEPPS, and excitation and emission filters at 365±25 and 485±5 nm, respectively, are used to measure calcium transients with Indo-1. Automated software may be used and customized for data acquisition and data analysis.

Advantages of the optical mapping system include non-invasiveness (no damage is inflicted to the cell membrane), recorded signals are real-time action potentials and/or calcium transients in contrast to derivatives of action potentials like extracellular recordings or slowly changing intracellular ionic concentrations or membrane potential like the FLIPR system.

For high-throughput optical mapping, analysis may be carried out using two different imaging approaches. For Contact Fluorescence Mapping, a microscope is not required. Fiber optic cables contact the bottom of a fluidics device, culture plate or wells of a multi-well plate containing muscle tissues. The fluidics device, plate or wells of the plate are then mapped based on the detected fluorescence. To screen compounds, test compounds are added to each individual device, well of a multi-well plate, and each bundle of fiber optic cables collects data from each different device or well providing data pertaining to muscle tissue response to the test compound.

In another embodiment, an inverted microscope may be used to map each well individually. Cells of a muscle tissue are contacted with, e.g., a chromophore, a fluorophor, or a bioluminescent material, and the microscope objective is moved from well to well to measure muscle activities or functions, e.g., electrophysiological changes. For example, the response of the muscle tissue to each test compound is monitored for alterations in cardiac excitation, e.g., to identify drugs that induce or do not cause cardiac arrhythmia. Each of the approaches provides significant advantages (e.g., speed, efficiency, no or minimal user contact with the muscle tissue, reduced user skill required, ability to observe and measure cell-cell interactions, ability to map action potential propagation and conduction velocity, and ability to observe and measure fibrillation and arrhythmia)) compared to previous assays used to measure electrophysiological changes (e.g., patch clamp assay in which a single cell is patch clamped).

These systems are well suited to screen test compounds for, for example, cardiac safety. For example, FDA Guideline S7B addresses "Safety pharmacology studies for assessing the potential for delayed ventricular repolarization by human pharmaceuticals". The devices and high-throughput in vitro assays described herein allow the identification of cardiac safety risks much earlier in the drug discovery process. The devices and methods of the invention are also useful for anti-arrhythmic and/or ion channel-targeted drug discovery.

In another aspect, the present invention provides a muscle chip comprising, in part, a muscle tissue prepared as described above.

Muscle chips are fluidic, e.g., millifluidic and/or microfluidic, devices that comprise living human cells cultured within the fluidic devices that recapitulate the three-dimensional (3D) tissue-tissue interfaces, mechanically active microenvironments, electrical stimulation, chemical conditions and complex organ-level functions. Examples of the muscle chips described herein, include, but are not limited to, heart chips to mimic beating heart, lung airway smooth muscle chips to mimic reactive airway, and skeletal muscle chips to mimic contracting skeletal muscle.

A Muscle Chip is a fluidic, e.g., millifluidic and/or microfluidic, device which can mimic physiological function of at least one mammalian (e.g., human) organ. In some embodiments, a muscle chip can be a fluidic, e.g., millifluidic and.or microfluidic, device which can mimic physiological function of one mammalian (e.g., human) organ. In some embodiments, a muscle chip can be a fluidic, e.g., millifluidic and.or microfluidic, device which can mimic physiological function of at least one (including 1, 2, 3, 4, 5, 6, 7 or more) mammalian (e.g., human) organs.

Figure 22:
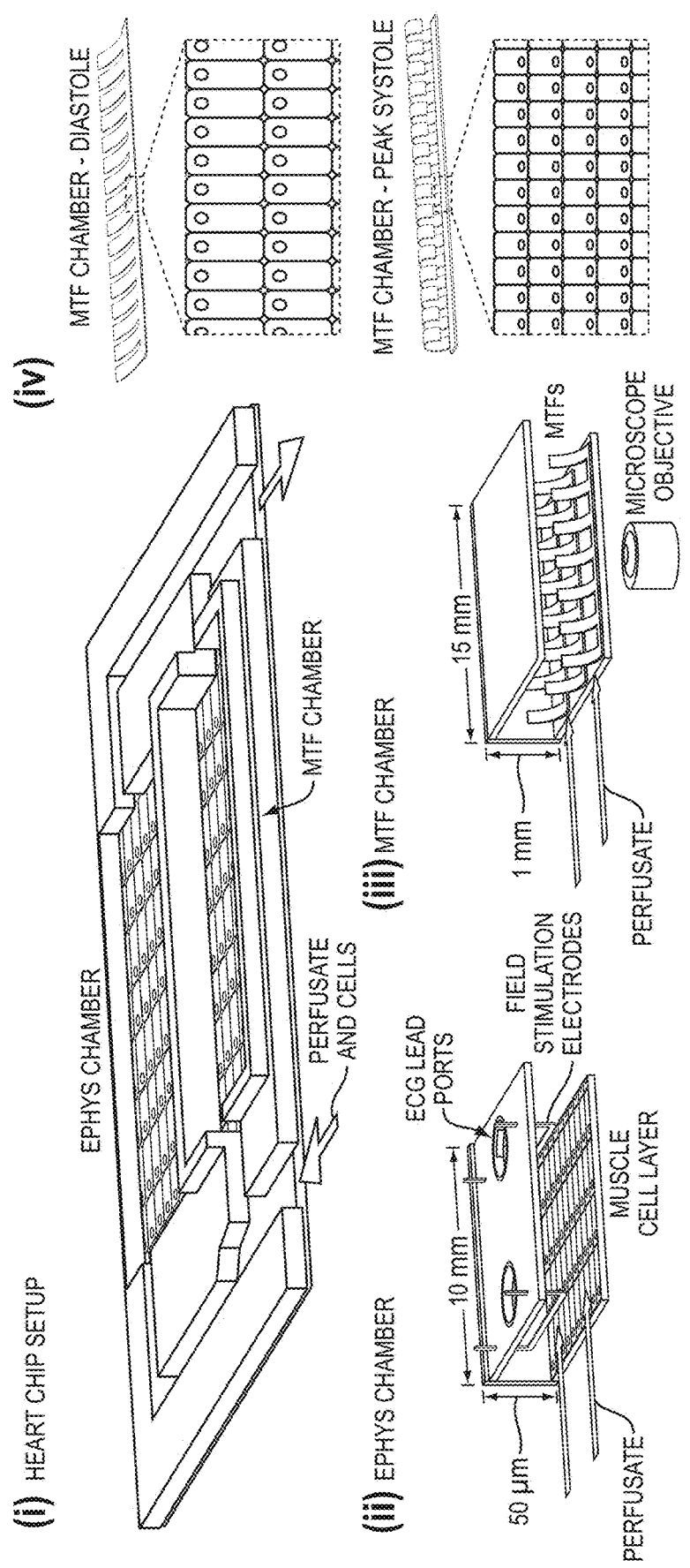
FIG. 22 schematically depicts one embodiment of a heart-on-a-chip. (i) Depicts dual chamber system with a single medium stream that feeds 2 chambers; an EPhys chamber and an MTF chamber. (ii) The EPhys chamber allows electrophysiological recordings on a monolayer of cardiac muscle in a low volume chamber with microelectrodes embedded in the bottom of the chamber. (iii) a larger chamber situated next to the EPhys chamber allows high throughput contractility measurements using an array of muscular thin films. (iv) In one embodiment, the MTF chamber consists of an anisotropic layer of cardiac myocytes cultured on laser-cut horizontal MTFs whose radius of curvature can be measured optically.
Figure 28:
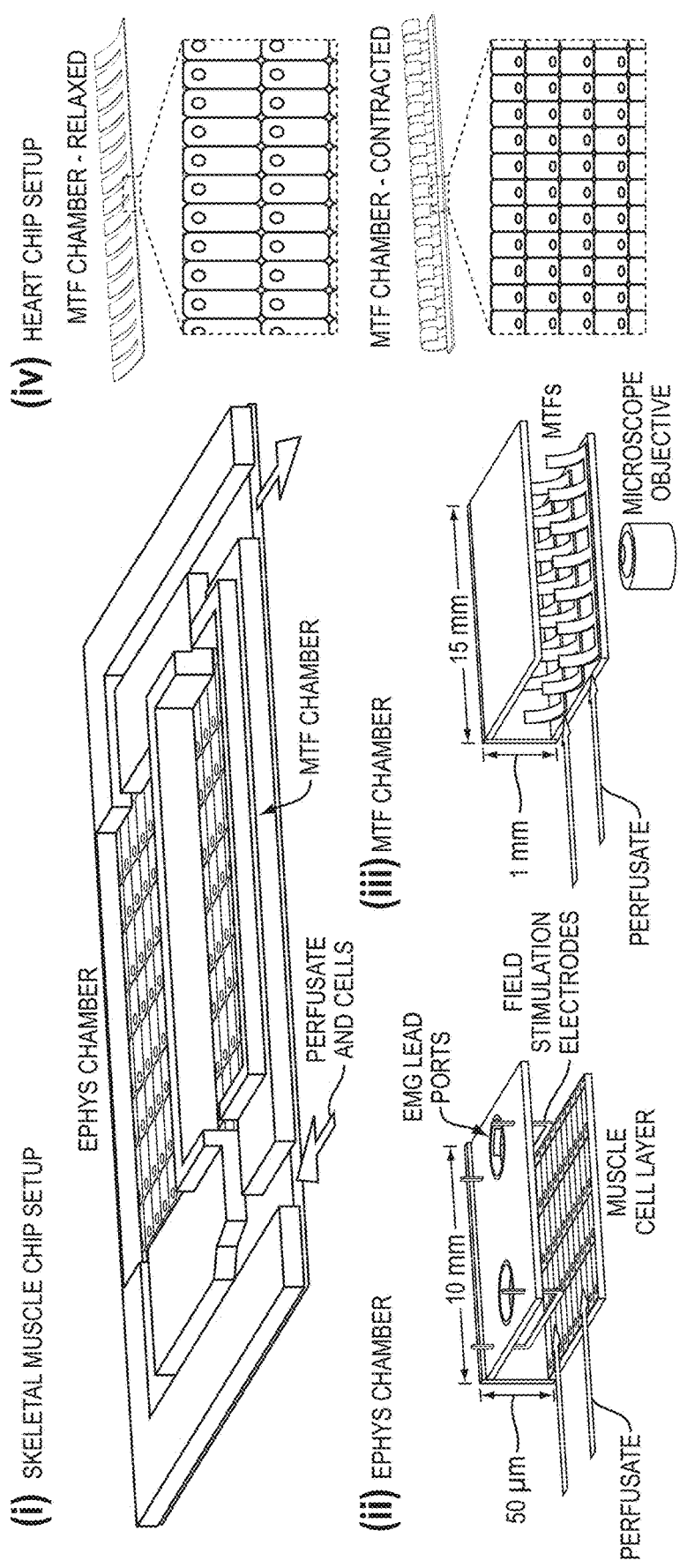
FIG. 28 schematically depicts an embodiment of a skeletal muscle-on-a-chip. Skeletal muscle chamber schematically (i) depicted as a dual chamber system with a single medium stream that feeds 2 chambers; an EPhys chamber and an MTF chamber (ii) The EPhys chamber allows EMG recordings on a monolayer of skeletal muscle in a low volume chamber with micro-electrodes embedded in the bottom of the chamber (iii) a larger chamber situated next to the EPhys chamber allows high throughput contractility measurements using an array of muscular thin films (iv) The MTF chamber consists of an anisotropic layer of skeletal myocytes cultured on laser-cut horizontal MTFs whose radius of curvature can be measured optically.
Figure 29:
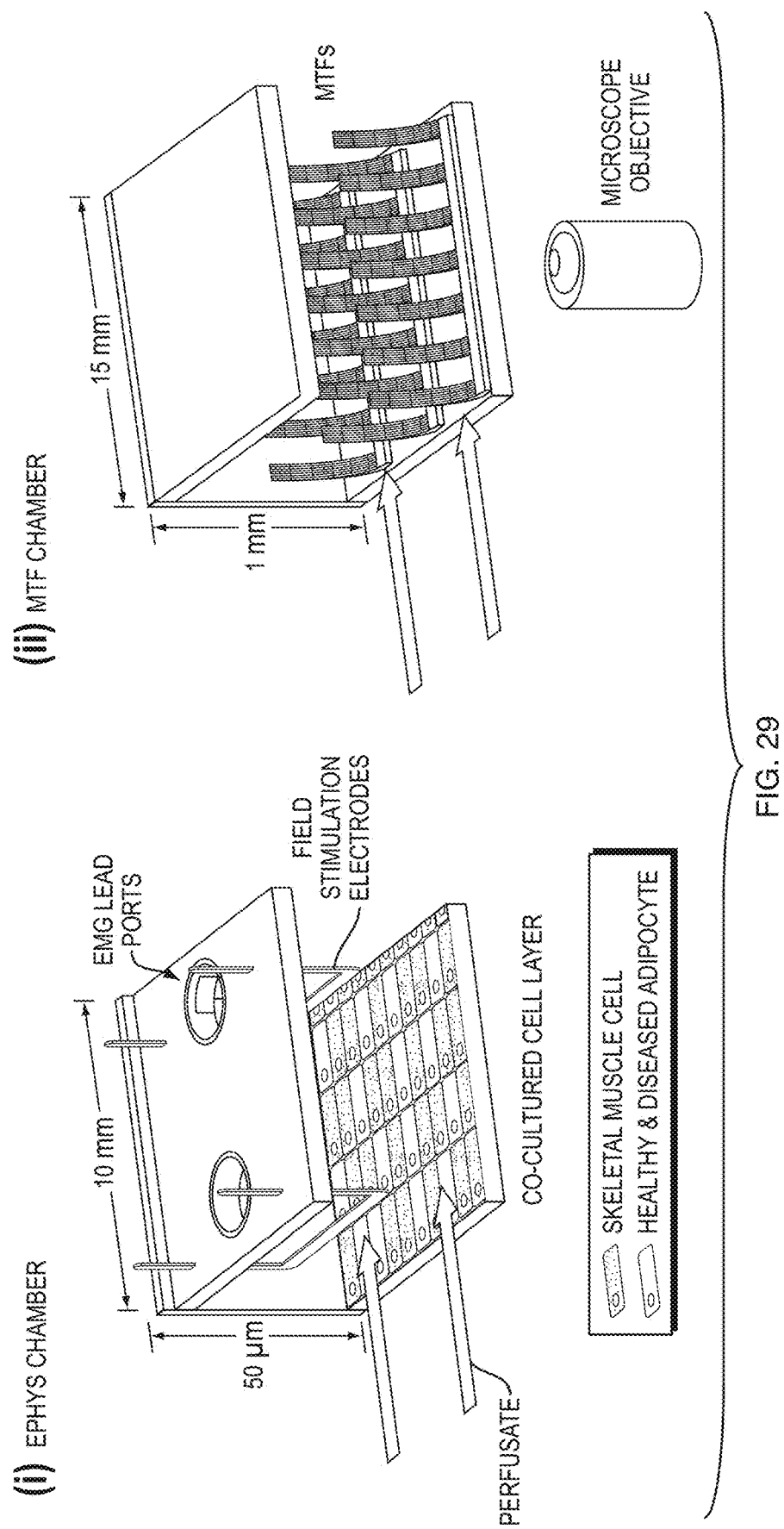
FIG. 29 schematically depicts functional readouts from the co-culture of skeletal muscle and adipocyte layers. (i) EPhys chamber, which allows EMG recordings on a monolayer of a co-culture of adipose and skeletal muscle. (ii) MTF chamber with an array of muscular thin films built from a heterogeneous co-culture of skeletal muscle and adipose tissue.

Accordingly, in one aspect, the present invention provides devices for measuring a contractile function. Exemplary devices are depicted in FIGS. 22, 28, and 29. The devices include a solid support structure, wherein the solid support structure is a fluidic, e.g., millifluidic and/or microfluidic, device comprising a first chamber and a second chamber operably connected. The first chamber comprises a monolayer of isotropically and/or anisotropically aligned muscle cells and an electrophysiological capturing device; and the second chamber comprises a plurality of muscle tissues, muscle tissue strips, e.g., horizontal muscle tissues, e.g., muscle thin films and/or hydrogel engineered muscle tissues (described above), and a device to measure contractility, e.g., an optical signal capturing device or a device for translating contractility into an electrical or magnetic signal, e.g., piezoresistive, piezoelectric, or strain sensor, e.g., embedded within the thin film and/or hydrogel.

In one embodiment, the plurality of muscle tissues comprise a flexible polymer layer and a population of isolated muscle cells seeded on the flexible polymer layer in a predetermined pattern, wherein said cells form a tissue structure which can perform a contractile function.

In another embodiment, the plurality of muscle tissues comprises a hydrogel layer and a population of isolated muscle cells seeded on the hydrogel layer in a predetermined pattern, wherein the cells form a tissue structure which can perform a contractile function.

In one embodiment, the muscle tissue strips are adhered at one end to the solid support structure (e.g., a horizontal muscle tissue). In another embodiment, the muscle tissue strips are not adhered to the solid support structure, e.g., are free standing. In yet other embodiments, a muscle tissue strip e.g., a tissue strip comprising a hydrogel, substantially all of the muscle tissue strip comprising the hydrogel is attached to the solid support structure, e.g., in embodiments in which contractility is measured as mechanical deformation.

In some embodiments, the chamber comprising an electrophysiological capturing device (also referred to herein as an "EPhys chamber") is a millifluidics chamber and the chamber comprising a signal capturing device (also referred to herein as an "MTF chamber") is a microfluidics chamber. In other embodiments, both chambers are microfluidics chambers.

In one embodiment, the monolayer of muscle cells and the cells of the muscle tissue are independently selected from the group consisting of cardiac muscle cells, ventricular cardiac muscle cells, atrial cardiac muscle cells, striated muscle cells, smooth muscle cells, and vascular smooth muscle cells.

In another aspect, the present invention provides devices for measuring a contractile function. The devices include a solid support structure, wherein the solid support structure is a fluidic, e.g., millifluidic and.or microfluidic, device comprising a first chamber and a second chamber operably connected. The first chamber comprises a plurality of muscle tissues, muscle tissues, e.g., horizontal muscle tissues, e.g., muscle thin films and/or hydrogel engineered muscle tissues (described above), and a device for measuring contractility, e.g., an optical signal capturing device or a device for translating contractility into an electrical or magnetic signal, e.g., piezoresistive, piezoelectric, or strain sensor, e.g., embedded within the thin film and/or hydrogel, wherein the plurality of muscle tissues comprise a flexible polymer layer and/or hydrogel and a population of isolated diseased cells seeded on a flexible polymer layer and/or hydrogel in a predetermined pattern, wherein said cells form a tissue structure which can perform a contractile function, and the second chamber comprises a plurality of muscle tissues, muscle tissue strips, e.g., horizontal muscle tissues, e.g., muscle thin films and/or hydrogel engineered muscle tissues (described above) and a device for measuring contractility, e.g., an optical signal capturing device or a device for translating contractility into an electrical or magnetic signal, e.g., piezoresistive, piezoelectric, or strain sensor, e.g., embedded within the thin film and/or hydrogel.

In one embodiment, the plurality of muscle tissues comprise a flexible polymer layer and a population of isolated healthy muscle cells seeded on the flexible polymer layer in a predetermined pattern, wherein the cells form a tissue structure which can perform a contractile function. In another embodiment, the plurality of muscle tissues comprise a hydrogel and a population of isolated healthy muscle cells seeded on the hydrogel layer in a predetermined pattern, wherein the cells form a tissue structure which can perform a contractile function.

In one embodiment, the muscle tissue strips are adhered at one end to the solid support structure (e.g., a horizontal muscle tissue). In another embodiment, the muscle tissue strips are not adhered to the solid support structure, e.g., are free standing. In yet other embodiments, a muscle tissue strip e.g., a tissue strip comprising a hydrogel, substantially all of the muscle tissue strip comprising the hydrogel is attached to the solid support structure, e.g., in embodiments in which contractility is measured as mechanical deformation.

In one embodiment, the cells of the muscle tissue are selected from the group consisting of cardiac muscle cells, ventricular cardiac muscle cells, atrial cardiac muscle cells, striated muscle cells, smooth muscle cells, and vascular smooth muscle cells.

In another aspect, the present invention provides devices for measuring a contractile function. The devices include a solid support structure, wherein the solid support structure is a fluidic, e.g., millifluidic and/or microfluidic, device, a plurality of muscle tissues, e.g., muscle tissue strips, e.g., horizontal muscle tissue, e.g., muscle thin films and/or hydrogel engineered muscle tissues.

In one embodiment, the plurality of muscle tissues comprise a flexible polymer layer and a population of isolated airway smooth muscle cells seeded on the flexible polymer layer in a predetermined pattern, wherein said cells form a tissue structure which can perform a contractile function.

In another embodiment, the plurality of muscle tissues comprise a hydrogel and a population of isolated airway smooth muscle cells seeded on the hydrogel layer in a predetermined pattern, wherein the cells form a tissue structure which can perform a contractile function. See, e.g., FIGS. 25 and 26.

Figure 23:
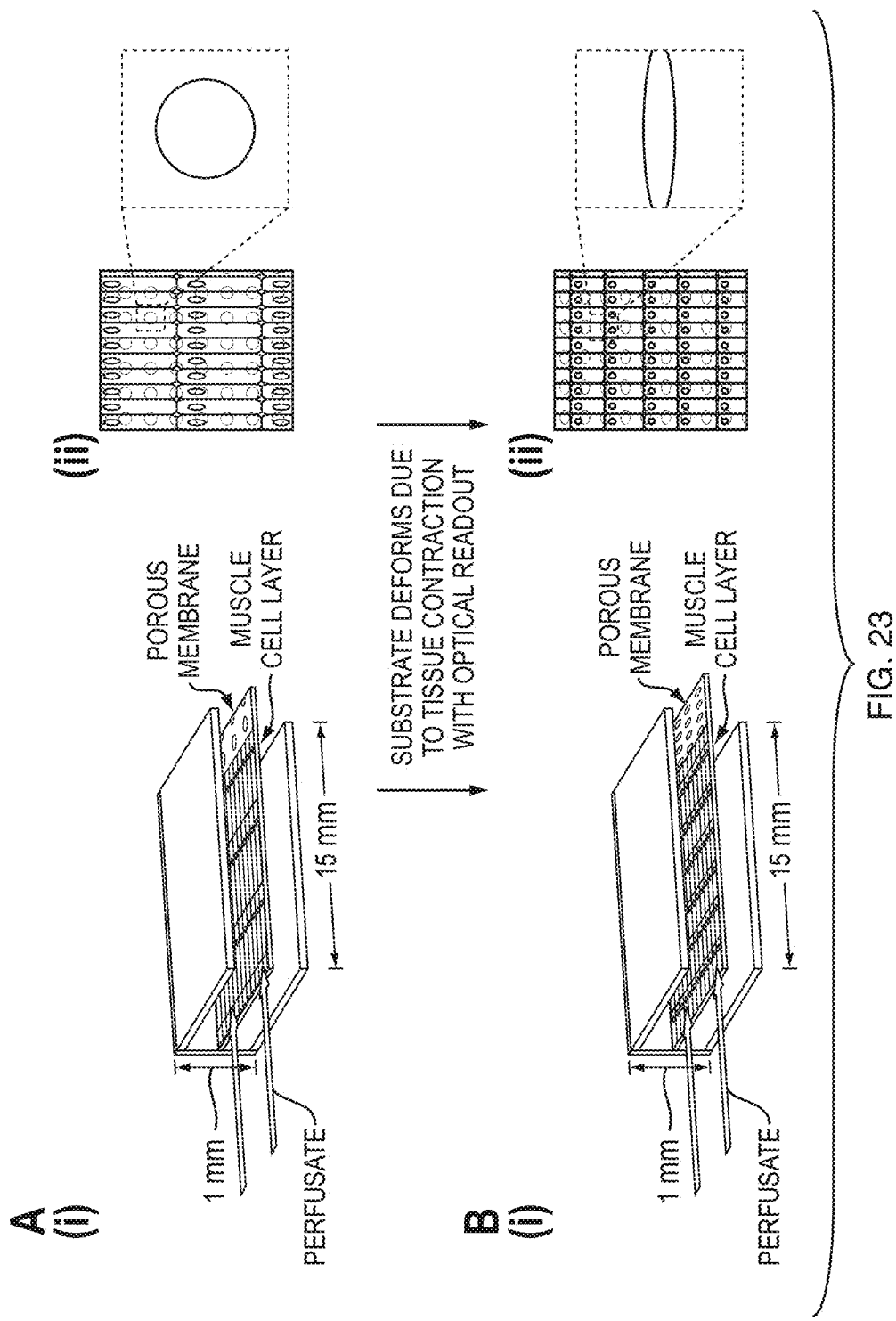
FIG. 23 schematically depicts another embodiment to monitor cellular contraction: (A) Cell monolayers are adhered to a deformable, perforated membrane within a microfluidic device (i & ii). (B) As the muscle cell layer contracts, the membrane deforms, such that the morphology of the holes within the membrane is altered (i & ii). The morphology of the holes within the membrane is monitored optically, with undeformed holes representing the relaxed state (A, ii) and deformed holes representing the contracted state (B, ii). The eccentricity of the holes is evaluated with existing software (see, e.g., FIGS. 7C and 7D).
Figure 27:
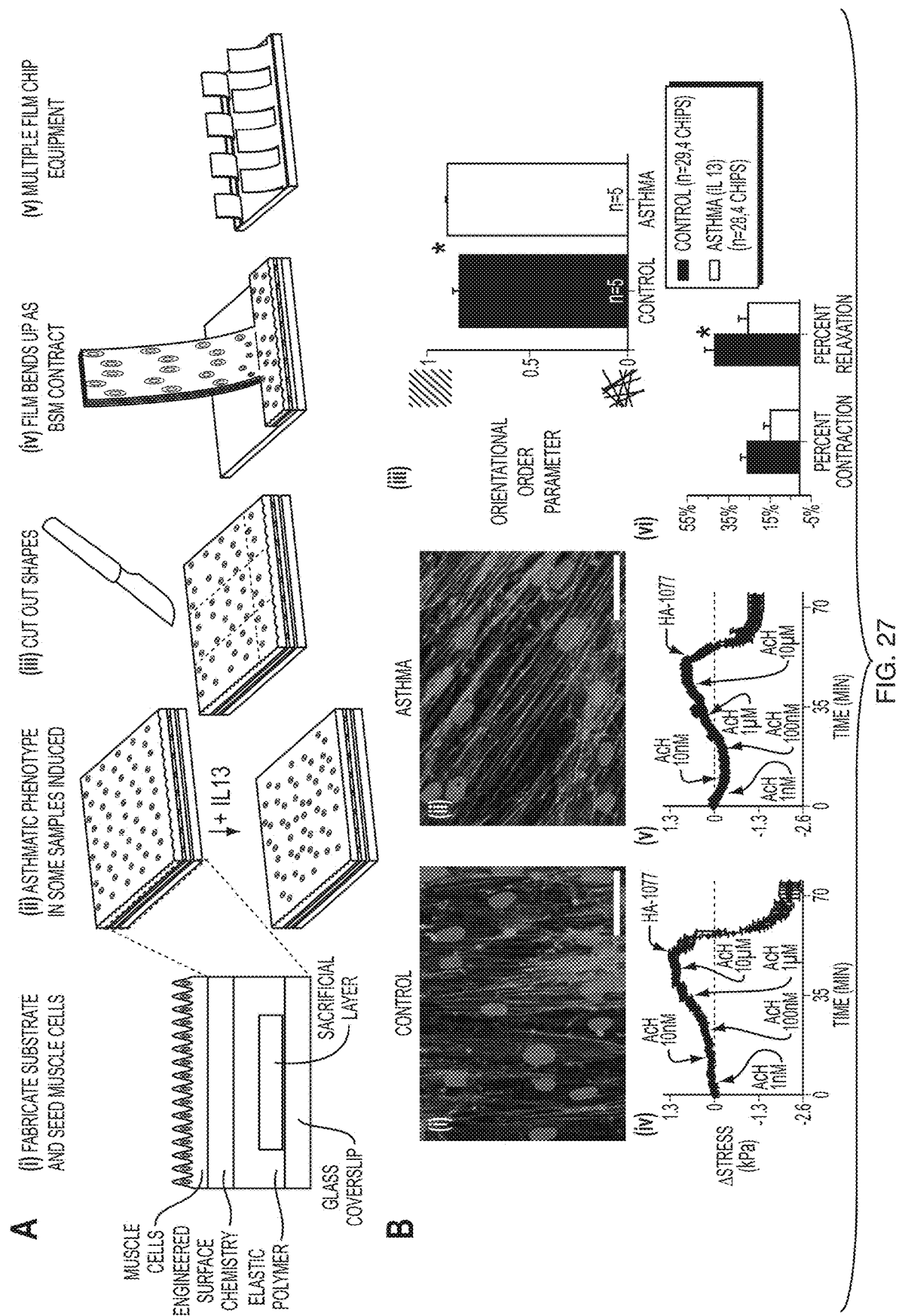
FIG. 27 depicts an embodiment of an airway smooth muscle-on-a-chip engineered to model asthma. (A) Manufacture of the chip containing human bronchial smooth muscle thin films (B) Actin staining of healthy engineered tissue (i) and the chemically induced asthma model (ii). Differences in actin alignment within the tissue constructs, as indicated by the orientational order parameter (iii) demonstrate significant remodeling of the contractile apparatus. Drug experiments (iv for healthy and v for asthma model) demonstrate differences in the contractile response to acetylcholine and to a Rho kinase inhibitor (HA 1077).

In one embodiment, the devices further comprise a porous membrane having epithelial cells adhered thereto and exposed to air flow situated above the muscle thin films, for example, as depicted in FIGS. 23 and 27.

In one embodiment, the muscle tissue strips are adhered at one end to the solid support structure (e.g., a horizontal muscle tissue). In another embodiment, the muscle tissue strips are not adhered to the solid support structure, e.g., are free standing. In yet other embodiments, a muscle tissue strip e.g., a tissue strip comprising a hydrogel, substantially all of the muscle tissue strip comprising the hydrogel is attached to the solid support structure, e.g., in embodiments in which contractility is measured as mechanical deformation.

In one embodiment, one or both of the chambers further comprises a device for measuring contractility, e.g., an optical signal capturing device or a device for translating contractility into an electrical or magnetic signal, e.g., piezoresistive, piezoelectric, or strain sensor, e.g., embedded within the thin film and/or hydrogel.

In one embodiment, the solid support structure is a fluidic, e.g., millifluidic and/or microfluidic, device comprising a first chamber and a second chamber operably connected. The first chamber comprises a plurality of muscle tissues, e.g., muscle tissue strips, e.g., horizontal muscle tissues, e.g., muscle thin films and/or hydrogel engineered muscle tissues, comprising a tissue structure comprising a population of isolated healthy airway smooth muscle cells, and the second chamber comprises a plurality of muscle tissues, e.g., horizontal muscle tissues, e.g., muscle thin films and/or hydrogel engineered muscle tissues, comprising a tissue structure comprising a population of isolated diseased airway smooth muscle cells.

In some embodiments where the muscle chips mimic physiological functions of more than one mammalian (e.g., human) organ, the muscle chips can comprise individual sub-units, each of which can mimic physiological function of one specific mammalian (e.g., human) organ.

A Muscle Chip generally comprises a number of channels. This can provide for a number of read-outs per chip allowing assessment of reproducibility that is the key for validation and implementation of the technology. The dimension of all the channels can be same or different or a combination of same and different. Each channel can be independently lined by differentiated one layer or multilayers of muscle-specific, human parenchymal cell types and vascular endothelium in relevant mechanochemical microenvironments. In some embodiments, a Muscle Chip can comprise at least two parallel (e.g., 2, 3, 4, 5, 6, 7, 8, 9, 10, or more) channels. In one embodiment, a Muscle Chip comprises four parallel channels. Without wishing to be bound by a theory, this configuration can provide quadruplicate read-outs per chip.

In some embodiments, the muscle chips can be disposable. In some embodiments, the muscle chips can be implantable.

In some embodiments, the muscle chips can be fabricated from any biocompatible materials. Examples of biocompatible materials include, but are not limited to, glass, silicons, polyurethanes or derivatives thereof, rubber, molded plastic, polymethylmethacrylate (PMMA), polycarbonate, polytetrafluoroethylene (TEFLON™), polyvinylchloride (PVC), polydimethylsiloxane (PDMS), and polysulfone. In one embodiment, muscle chips can be fabricated from PDMS (poly-dimethylsiloxane).

Muscle chips generally comprise a body and at least one channel disposed therein. The number and dimension of channels in a muscle chip can vary depending on the design, dimension and/or function of the muscle chip. In some embodiments, a muscle chip can comprise at least one, at least two, at least three, at least four, at least five, at least six, at least seven, at least eight, at least nine, at least ten channels.

One of skill in the art is able to design and determine optimum number and dimension of channels required to achieve a certain application. For example, if assessment of reproducibility is desirable, a muscle chip can be constructed to comprise at least two, at least three, at least four, at least five identical channels. This configuration can provide multiple read-outs per chip, which will allow assessment of reproducibility that is the key for validation and implementation of the technology. In one embodiment, a muscle chip can comprise four parallel identical channels, which can provide quadruplicate readout per chips.

In some embodiments, at least one channel of the muscle chips can comprise one or more membranes, e.g., 1, 2, 3 or more membranes to separate the channel into sub-channels. The membrane can be rigid or at least partially flexible. The term "flexible" as used herein refers to a membrane that can be stretched by at least about 3%, at least about 5%, at least about 10%, at least about 15%, at least about 20%, at least about 25%, at least about 50%, at least about 60% or more, of its original length, when a pressure is applied. In some embodiments, the membrane can restore to its original length after the pressure is released.

In some embodiments, the membrane can be non-porous or at least porous. In some embodiments, the pore size of the membrane can be large enough to allow cells pass through it. In some embodiments, the pore size of the membrane is too small for cells to pass through it, but large enough for nutrient or fluid molecules to pass through it.

In some embodiments, the membrane can be non-coated or coated with extracellular matrix molecules (ECM), or other proteins such as growth factors or ligands. In some embodiments, the surface of the membrane can be activated, e.g., with any art-recognized reactions, such that ECM molecules, proteins such as growth factors or ligands, can be attached to it.

In some embodiments, the membrane can be seeded with or without cells. In some embodiments where cells are seeded on the membrane, cells can be seeded on one side or both sides of the membrane. In some embodiments, both sides of the membrane can be seeded with the same cells. In other embodiments, both sides of the membrane can be seeded with different cells.

In some embodiments, the membrane can be seeded with at least one layer of cells, including, at least 2 layers of cells or more. Each layer of cells can be the same or different.

In some embodiments, at least one channel or sub-channel of the muscle chip can be filled with gel, e.g., collagen gel. The gel can be seeded with or without cells.

In some embodiments, at least one channel or sub-channel of the muscle chip can contain a tissue.

In some embodiments, there can be at least one micro-post, including 1, 2, 3, 4, 5, 6, 7, 8, 9, 10 or more micro-posts within one or more channels. The dimension and/or arrangement of the micro-posts can be determined by a user.

In some embodiments, the muscle chips can comprise a plurality of ports. For example, the muscle chips can comprise at least one inlet port for introducing culture medium, nutrients or test agents such as drugs into the muscle chips, and at least one outlet port for a fluid to exit. In some embodiments, at least one port can be connected to a pump or a syringe, e.g., via a tubing, to facilitate the fluid transfer through the channel and/or to apply a pressure to the channel. In some embodiments, at least one port can be connected to at least one electrical component, e.g., an electrode for ECG measurement. In some embodiments, at least one port can be connected to a nebulizer, e.g., to generate aerosolized liquid for aerosol delivery. In some embodiments, at least one port can be connected to or interfaced with a processor, which stores and/or analyzes the signal from a bio sensor incorporated therein. The processor can transfer the data to computer memory (either hard disk or RAM) from where it can be used by a software program to further analyze, print and/or display the results.

As a muscle chip is developed to mimic the respective function of a muscle tissue, the design of each muscle chip can be different according to their respective physiological properties and/or functions. For example, the Muscle Chips can differ in cell populations (e.g., cell types and/or initial cell seeding density), internal design, microarchitecture, dimensions, fluidic control, mechanical and electrical control and read-outs depending on the muscle type.

In some embodiments, however, the muscle chips can be designed to have a common shape and have positioned inlets and outlets for delivery of fluids to the Microvascular and Interstitial fluid channels (see below) lined by human microvascular endothelium and organ-specific parenchymal cells (e.g., alveolar epithelium, heart muscle, hepatocytes), respectively.

To fabricate muscle organ chips, e.g., heart chips, in some embodiments, functional muscle tissues are fabricated first and then multiplexed in a single microfluidic device. For example, functional heart tissues can be fabricated by culturing neonatal rat ventricular cardiomyocytes on elastomeric polymer thin films micropatterned with ECM proteins to promote spatially ordered, two-dimensional myogenesis and create 'muscular thin films' (MTFs), as described above. In other embodiments, a base layer is provided, the muscle tissues are fabricated using any of the methods described herein, and the fluidics components (e.g., fluidics connections, housing) are placed around the muscle tissues to create the fluidics device. These muscle tissue constructs are electrically functional and actively contractile, generating stresses comparable to those produced by whole papillary muscle, and the muscle tissue can be used to measure effects on muscle cell contractile function in vitro during electrical and pharmacological stimulation. The muscle tissues, e.g., MTFs and/or hydrogel engineered muscle tissues (e.g., at least 1, at least 2, at least 3, at least 4, at least 5, at least 6, at least 7, at least 8, at least 9, at least 10) can then be multiplexed, e.g., in an array, within a microfluidic chip (FIG. 22).

In another embodiment, multi-layered Muscle chips, e.g., Heart chips, can be constructed. For example, a multi-layered Heart chip can contain a Microvascular Channel lined by human endothelium adherent to a porous membrane that separates it from an MTF-lined 'Interstitial Channel', such as similar to the configuration of a lung chip. The inventors have demonstrated that microengineered MTFs effectively mimic pharmacological responses of adult rat papillary muscle strips (FIG. 24), which are commonly used to screen cardiac tissue responses to drugs by the pharmaceutical industry.

In some embodiments, the heart chips can further comprise heart-specific parenchymal cells, e.g., cardiomyocytes, to further mimic the physiological environment and/or function of the heart. The cardiomyocytes can be isolated from a tissue or obtained from a commercial source, or by differentiating stems cells to cardiomyocytes, e.g., induced pluriopotent stem cell-derived cardiomyocytes, as described supra.

In some embodiments, the heart chips can be modified for various analyses. For example, the Heart Chips can have at least one set of MTF-lined Interstitial Channels (including at least 2 sets, at least 3 sets, at least 4 sets, at least 5 sets or more) for contractility analysis. Additionally, the heart chips can have at least one parallel set of larger Interstitial Channels (including at least 2 sets, at least 3 sets, at least 4 sets, at least 5 sets or more) lined by one or a plurality of electrodes (e.g., platinum electrodes) as an 'Electrophysiological Chamber' for electrical pacing and analysis of changes in cardiac electrical potential with a lead electrocardiogram. Without wishing to be bound, in some embodiments, both the Interstitial Channels and Electrophysiological Chambers can be fed by single medium stream introduced through an underlying endothelium-lined microvascular channel.

The presence of the endothelium and its basement membrane lining the Microvascular Channel on the opposite side of the membrane, plus the ability to perfuse different media compositions through the Interstitial versus Microvascular Channels can allow different experimental conditions for various applications.

II. Applications of the Devices of the Invention

The devices of the invention are useful for, among other things, measuring muscle activities or functions, investigating muscle developmental biology and disease pathology, as well as in drug discovery and toxicity testing.

Accordingly, the present invention also provides methods for identifying a compound that modulates a contractile function. The methods include providing a plurality of muscle tissues, e.g., muscle tissue strips, e.g., horizontal muscle tissues, e.g., muscle thin films and/or hydrogel engineered muscle tissues; contacting a plurality of the muscle tissues with a test compound; and determining the effect of the test compound on a contractile function in the presence and absence of the test compound, wherein a modulation of the contractile function in the presence of the test compound as compared to the contractile function in the absence of the test compound indicates that the test compound modulates a contractile function, thereby identifying a compound that modulates a contractile function.

In another aspect, the present invention also provides methods for identifying a compound useful for treating or preventing a muscle disease. The methods include providing a plurality of muscle tissues, e.g., muscle strips, e.g., horizontal muscle tissues, e.g., muscle thin films and/or hydrogel engineered muscle tissues; contacting a plurality of the muscle tissues with a test compound; and determining the effect of the test compound on a contractile function in the presence and absence of the test compound, wherein a modulation of the contractile function in the presence of the test compound as compared to the contractile function in the absence of the test compound indicates that the test compound modulates a contractile function, thereby identifying a compound useful for treating or preventing a muscle disease.

The methods of the invention generally comprise determining the effect of a test compound on a muscle tissue, e.g., horizontal muscle tissues, e.g., muscle thin films and/or hydrogel engineered muscle tissues as a whole, however, the methods of the invention may comprise further evaluating the effect of a test compound on an individual cell type(s) of the muscle tissue.

As used herein, the various forms of the term "modulate" are intended to include stimulation (e.g., increasing or upregulating a particular response or activity) and inhibition (e.g., decreasing or downregulating a particular response or activity).

As used herein, the term "contacting" (e.g., contacting a plurality of muscle tissues with a test compound) is intended to include any form of interaction (e.g., direct or indirect interaction) of a test compound and a muscle tissue or a plurality of muscle tissues. The term contacting includes incubating a compound and a muscle tissue or plurality of muscle tissues together (e.g., adding the test compound to an a muscle tissue or plurality of a muscle tissues in culture).

Test compounds, may be any agents including chemical agents (such as toxins), small molecules, pharmaceuticals, peptides, proteins (such as antibodies, cytokines, enzymes, and the like), nanoparticles, and nucleic acids, including gene medicines and introduced genes, which may encode therapeutic agents, such as proteins, antisense agents (i.e., nucleic acids comprising a sequence complementary to a target RNA expressed in a target cell type, such as RNAi or siRNA), ribozymes, and the like.

The test compound may be added to a muscle tissue by any suitable means. For example, the test compound may be added drop-wise onto the surface of a device of the invention and allowed to diffuse into or otherwise enter the device, or it can be added to the nutrient medium and allowed to diffuse through the medium. In the embodiment where the device of the invention comprises a multi-well plate, each of the culture wells may be contacted with a different test compound or the same test compound. In one embodiment, the screening platform includes a microfluidics handling system to deliver a test compound and simulate exposure of the microvasculature to drug delivery. In one embodiment, a solution comprising the test compound may also comprise fluorescent particles, and a muscle cell function may be monitored using Particle Image Velocimetry (PIV).

Numerous physiologically relevant parameters, e.g., muscle activities, e.g., biomechanical and electrophysiological activities, can be evaluated using the methods and devices of the invention. For example, in one embodiment, the devices of the present invention can be used in contractility assays for contractile cells, such as muscular cells or tissues, such as chemically and/or electrically stimulated contraction of vascular, airway or gut smooth muscle, cardiac muscle, vascular endothelial tissue, or skeletal muscle. In addition, the differential contractility of different muscle cell types to the same stimulus (e.g., pharmacological and/or electrical) can be studied.

In another embodiment, the devices of the present invention can be used for measurements of solid stress due to osmotic swelling of cells. For example, as the cells swell the muscle tissue will bend and as a result, volume changes, force and points of rupture due to cell swelling can be measured.

In another embodiment, the devices of the present invention can be used for pre-stress or residual stress measurements in cells. For example, vascular smooth muscle cell remodeling due to long term contraction in the presence of endothelin-1 can be studied.

Further still, the devices of the present invention can be used to study the loss of rigidity in tissue structure after traumatic injury, e.g., traumatic brain injury. Traumatic stress can be applied to vascular smooth muscle thin films as a model of vasospasm. These devices can be used to determine what forces are necessary to cause vascular smooth muscle to enter a hyper-contracted state. These devices can also be used to test drugs suitable for minimizing vasospasm response or improving post-injury response and returning vascular smooth muscle contractility to normal levels more rapidly.

In other embodiments, the devices of the present invention can be used to study biomechanical responses to paracrine released factors (e.g., vascular smooth muscle dilation due to release of nitric oxide from vascular endothelial cells, or cardiac myocyte dilation due to release of nitric oxide).

In other embodiments, the devices of the invention can be used to evaluate the effects of a test compound on an electrophysiological parameter, e.g., an electrophysiological profile comprising a voltage parameter selected from the group consisting of action potential, action potential morphology, action potential duration (APD), conduction velocity (CV), refractory period, wavelength, restitution, bradycardia, tachycardia, reentrant arrhythmia, and/or a calcium flux parameter, e.g., intracellular calcium transient, transient amplitude, rise time (contraction), decay time (relaxation), total area under the transient (force), restitution, focal and spontaneous calcium release, and wave propagation velocity. For example, a decrease in a voltage or calcium flux parameter of a muscle tissue comprising cardiomyocytes upon contacting the MTF with a test compound, would be an indication that the test compound is cardiotoxic.

In yet another embodiment, the devices of the present invention can be used in pharmacological assays for measuring the effect of a test compound on the stress state of a tissue. For example, the assays may involve determining the effect of a drug on tissue stress and structural remodeling of the muscle tissue. In addition, the assays may involve determining the effect of a drug on cytoskeletal structure (e.g., sarcomere alignment) and, thus, the contractility of the muscle tissue.

In still other embodiments, the devices of the present invention can be used to measure the influence of biomaterials on a biomechanical response. For example, differential contraction of vascular smooth muscle remodeling due to variation in material properties (e.g., stiffness, surface topography, surface chemistry or geometric patterning) of polymeric thin films can be studied.

In further embodiments, the devices of the present invention can be used to study functional differentiation of stem cells (e.g., pluripotent stem cells, multipotent stem cells, induced pluripotent stem cells, and progenitor cells of embryonic, fetal, neonatal, juvenile and adult origin) into contractile phenotypes. For example, undifferentiated cells, e.g., stem cells, are coated on the thin films and differentiation into a contractile phenotype is observed by thin film bending. Differentiation into an anisotropic tissue may also be observed by quantifying the degree of alignment of sarcomeres and/or quantifying the orientational order parameter (OOP). Differentiation can be observed as a function of: co-culture (e.g., co-culture with differentiated cells), paracrine signaling, pharmacology, electrical stimulation, magnetic stimulation, thermal fluctuation, transfection with specific genes, chemical and/or biomechanical perturbation (e.g., cyclic and/or static strains).

In one embodiment a biomechanical perturbation is stretching of, e.g., the flexible polymer layer during tissue formation. In one embodiment, the stretching is cyclic stretching. In another embodiment, the stretching is sustained stretching.

In one embodiment, the flexible polymer layer is stretched at an appropriate time after cell seeding that is based on the type(s) of cells seeded. In one embodiment, the flexible polymer layer is stretched at about minutes, hours, or days after cell seeding onto a patterned flexible polymer layer. In one embodiment, the flexible polymer layer is stretched at about 0, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or about 3.0 hours after cell seeding onto a patterned flexible polymer layer.

In one embodiment, the flexible polymer layer is patterned isotropically. Stretching, therefore, results in the formation of anisotropic tissue, the anisotropy of which is in the direction of the stretch.

In another embodiment, the flexible polymer layer is patterned anistropically and stretching enhances the anisotropy of the tissue formed.

In one embodiment, the flexible polymer layer is stretched using about a 0.1, 0.2, 0.3, 0.4, 0.5, 1.0, 1.5, 2.0, 2.5, 3.0, 3.5, 4, 4.5, 5.0, 5.5, 6.0, 6.5, 7.0, 7.5, 8.0, 8.5, 9.0, 9.5, or about 10.0 Hertz (Hz) cyclic stretch. In one embodiment, the flexible polymer layer is stretched using about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, or about 20.0% strength sustained stretch.

In another embodiment, the devices of the invention may be used to determine the toxicity of a test compound by evaluating, e.g., the effect of the compound on an electrophysiological response of a muscle tissue. For example, opening of calcium channels results in influx of calcium ions into the cell, which plays an important role in excitation-contraction coupling in cardiac and skeletal muscle fibers. The reversal potential for calcium is positive, so calcium current is almost always inward, resulting in an action potential plateau in many excitable cells. These channels are the target of therapeutic intervention, e.g., calcium channel blocker sub-type of anti-hypertensive drugs. Candidate drugs may be tested in the electrophysiological characterization assays described herein to identify those compounds that may potentially cause adverse clinical effects, e.g., unacceptable changes in cardiac excitation, that may lead to arrhythmia.

For example, unacceptable changes in cardiac excitation that may lead to arrhythmia include, e.g., blockage of ion channel requisite for normal action potential conduction, e.g., a drug that blocks $Na^+$ channel would block the action potential and no upstroke would be visible; a drug that blocks $Ca^{2+}$ channels would prolong repolarization and increase the refractory period; blockage of $K^+$ channels would block rapid repolarization, and, thus, would be dominated by slower $Ca^{2+}$ channel mediated repolarization.

In addition, metabolic changes may be assessed to determine whether a test compound is toxic by determining, e.g., whether contacting with a test compound results in a decrease in metabolic activity and/or cell death. For example, detection of metabolic changes may be measured using a variety of detectable label systems such as fluormetric/chrmogenic detection or detection of bioluminescence using, e.g., AlamarBlue fluorescent/chromogenic determination of REDOX activity (Invitrogen), REDOX indicator changes from oxidized (non-fluorescent, blue) state to reduced state (fluorescent, red) in metabolically active cells; Vybrant MTT chromogenic determination of metabolic activity (Invitrogen), water soluble MTT reduced to insoluble formazan in metabolically active cells; and Cyquant NF fluorescent measurement of cellular DNA content (Invitrogen), fluorescent DNA dye enters cell with assistance from permeation agent and binds nuclear chromatin. For bioluminescent assays, the following exemplary reagents may be used: Cell-Titer Glo luciferase-based ATP measurement (Promega), a thermally stable firefly luciferase glows in the presence of soluble ATP released from metabolically active cells.

The devices of the invention are also useful for evaluating the effects of particular delivery vehicles for therapeutic agents e.g., to compare the effects of the same agent administered via different delivery systems, or simply to assess whether a delivery vehicle itself (e.g., a viral vector or a liposome) is capable of affecting the biological activity of the muscle tissue. These delivery vehicles may be of any form, from conventional pharmaceutical formulations, to gene delivery vehicles. For example, the devices of the invention may be used to compare the therapeutic effect of the same agent administered by two or more different delivery systems (e.g., a depot formulation and a controlled release formulation). The devices and methods of the invention may also be used to investigate whether a particular vehicle may have effects of itself on the tissue. As the use of gene-based therapeutics increases, the safety issues associated with the various possible delivery systems become increasingly important. Thus, the devices of the present invention may be used to investigate the properties of delivery systems for nucleic acid therapeutics, such as naked DNA or RNA, viral vectors (e.g., retroviral or adenoviral vectors), liposomes and the like. Thus, the test compound may be a delivery vehicle of any appropriate type with or without any associated therapeutic agent.

Furthermore, the devices of the present invention are a suitable in vitro model for evaluation of test compounds for therapeutic activity with respect to, e.g., a muscular and/or neuromuscular disease or disorder. For example, the devices of the present invention (e.g., comprising muscle cells) may be contacted with a candidate compound by, e.g., diffusion of the test compound added drop-wise on the surface of a muscle tissue, diffusion of a test compound through the culture medium, or immersion in a bath of media containing the test compound, and the effect of the test compound on muscle activity (e.g., a biomechanical and/or electrophysiological activity) may measured as described herein, as compared to an appropriate control, e.g., an untreated muscle tissue. Alternatively, a device of the invention may be bathed in a medium containing a candidate compound, and then the cells are washed, prior to measuring a muscle activity (e.g., a biomechanical and/or electrophysiological activity) as described herein. Any alteration to an activity determined using the device in the presence of the test agent (as compared to the same activity using the device in the absence of the test compound) is an indication that the test compound may be useful for treating or preventing a muscle disease, e.g., a neuromuscular disease.

For use in the methods of the invention, the cells seeded onto the muscle tissue may be normal muscle cells (cardiac, smooth, or skeletal muscle cells), abnormal muscle cells (e.g., those derived from a diseased tissue, or those that are physically or genetically altered to achieve a abnormal or pathological phenotype or function), normal or diseased muscle cells derived from embryonic stem cells or induced pluripotent stem cells, or normal cells that are seeded/printed onto the film in an abnormal or aberrant configuration. In some cases, both muscle cells and neuronal cells are present on the film.

Evaluation of muscle activity includes determining the degree of contraction, i.e., the degree of curvature or bend of the muscular film, and the rate or frequency of contraction/rate of relaxation compared to a normal control or control film in the absence of the test compound. An increase in the degree of contraction or rate of contraction indicates that the compound is useful in treatment or amelioration of pathologies associated with myopathies such as muscle weakness or muscular wasting. Such a profile also indicates that the test compound is useful as a vasocontractor. A decrease in the degree of contraction or rate of contraction is an indication that the compound is useful as a vasodilator and as a therapeutic agent for muscle or neuromuscular disorders characterized by excessive contraction or muscle thickening that impairs contractile function.

Compounds evaluated in this manner are useful in treatment or amelioration of the symptoms of muscular and neuromuscular pathologies such as those described below. Muscular Dystrophies include Duchenne Muscular Dystrophy (DMD) (also known as Pseudohypertrophic), Becker Muscular Dystrophy (BMD), Emery-Dreifuss Muscular Dystrophy (EDMD), Limb-Girdle Muscular Dystrophy (LGMD), Facioscapulohumeral Muscular Dystrophy (FSH or FSHD) (Also known as Landouzy-Dejerine), Myotonic Dystrophy (MMD) (Also known as Steinert's Disease), Oculopharyngeal Muscular Dystrophy (OPMD), Distal Muscular Dystrophy (DD), and Congenital Muscular Dystrophy (CMD). Motor Neuron Diseases include Amyotrophic Lateral Sclerosis (ALS) (Also known as Lou Gehrig's Disease), Infantile Progressive Spinal Muscular Atrophy (SMA, SMA1 or WH) (also known as SMA Type 1, Werdnig-Hoffman), Intermediate Spinal Muscular Atrophy (SMA or SMA2) (also known as SMA Type 2), Juvenile Spinal Muscular Atrophy (SMA, SMAS or KW) (also known as SMA Type 3, Kugelberg-Welander), Spinal Bulbar Muscular Atrophy (SBMA) (also known as Kennedy's Disease and X-Linked SBMA), Adult Spinal Muscular Atrophy (SMA). Inflammatory Myopathies include Dermatomyositis (PM/DM), Polymyositis (PM/DM), Inclusion Body Myositis (IBM). Neuromuscular junction pathologies include Myasthenia Gravis (MG), Lambert-Eaton Syndrome (LES), and Congenital Myasthenic Syndrome (CMS). Myopathies due to endocrine abnormalities include Hyperthyroid Myopathy (HYP™), and Hypothyroid Myopathy (HYPO™). Diseases of peripheral nerves include Charcot-Marie-Tooth Disease (CMT) (Also known as Hereditary Motor and Sensory Neuropathy (HMSN) or Peroneal Muscular Atrophy (PMA)), Dejerine-Sottas Disease (DS) (Also known as CMT Type 3 or Progressive Hypertrophic Interstitial Neuropathy), and Friedreich's Ataxia (FA). Other Myopathies include Myotonia Congenita (MC) (Two forms: Thomsen's and Becker's Disease), Paramyotonia Congenita (PC), Central Core Disease (CCD), Nemaline Myopathy (NM), Myotubular Myopathy (MTM or MM), Periodic Paralysis (PP) (Two forms: Hypokalemic—HYPOP—and Hyperkalemic—HYPP) as well as myopathies associated with HIV/AIDS.

The methods and devices of the present invention are also useful for identifying therapeutic agents suitable for treating or ameliorating the symptoms of metabolic muscle disorders such as Phosphorylase Deficiency (MPD or PYGM) (Also known as McArdle's Disease), Acid Maltase Deficiency (AMD) (Also known as Pompe's Disease), Phosphofructokinase Deficiency (PFKM) (Also known as Tarui's Disease), Debrancher Enzyme Deficiency (DBD) (Also known as Cori's or Forbes' Disease), Mitochondrial Myopathy (MITO), Carnitine Deficiency (CD), Carnitine Palmityl Transferase Deficiency (CPT), Phosphoglycerate Kinase Deficiency (PGK), Phosphoglycerate Mutase Deficiency (PGAM or PGAMM), Lactate Dehydrogenase Deficiency (LDHA), and Myoadenylate Deaminase Deficiency (MAD).

In addition to the disorders listed above, the screening methods described herein are useful for identifying agents suitable for reducing vasospasms, heart arrhythmias, and cardiomyopathies.

Vasodilators identified as described above are used to reduce hypertension and compromised muscular function associated with atherosclerotic plaques. Smooth muscle cells associated with atherosclerotic plaques are characterized by an altered cell shape and aberrant contractile function. Such cells are used to populate a thin film, exposed to candidate compounds as described above, and muscular function evaluated as described above. Those agents that improve cell shape and function are useful for treating or reducing the symptoms of such disorders.

Smooth muscle cells and/or striated muscle cells line a number of lumen structures in the body, such as uterine tissues, airways, gastrointestinal tissues (e.g., esophagus, intestines) and urinary tissues, e.g., bladder. The function of smooth muscle cells on thin films in the presence and absence of a candidate compound may be evaluated as described above to identify agents that increase or decrease the degree or rate of muscle contraction to treat or reduce the symptoms associated with a pathological degree or rate of contraction. For example, such agents are used to treat gastrointestinal motility disorders, e.g., irritable bowel syndrome, esophageal spasms, achalasia, Hirschsprung's disease, or chronic intestinal pseudo-obstruction.

The present invention is next described by means of the following examples. However, the use of these and other examples anywhere in the specification is illustrative only, and in no way limits the scope and meaning of the invention or of any exemplified form. The invention is not limited to any particular preferred embodiments described herein. Many modifications and variations of the invention may be apparent to those skilled in the art and can be made without departing from its spirit and scope. The contents of all references, patents and published patent applications cited throughout this application, including the figures, are incorporated herein by reference.

EXAMPLES

Example 1: Muscular Thin Film Device and Use Thereof for Determining a Contractile Function A. Substrate Fabrication Polydimethylsiloxane (PDMS) thin film substrates were fabricated via a multi-step spin coating process. Poly(N-isopropylacrylamide) (PIPAAm) (Polysciences, Inc.) was dissolved at 10 wt % in 99.4% 1-butanol (w/v) and spun coat onto the glass cover slips. Sylgard 184 (Dow Corning) polydimethylsiloxane (PDMS) elastomer was mixed at a 10:1 base to curing agent ratio, doped with 0.1% by volume 0.2 μm Fluorospheres (Invitrogen), and spin coated on top of the PIPAAm coated glass cover slip. Polydimethylsiloxane-coated cover slips were then cured.

B. ECM Patterning

The polydimethylsiloxane thin films were coated with either an isotropic or anisotropic layer of extracellular matrix (ECM) (e.g. fibronectin, laminin, collagen I). In each case, immediately prior to ECM treatment, the polydimethylsiloxane-coated cover slips were UV ozone treated for 8 minutes to sterilize the surface and increase hydrophilicity. All subsequent processing was performed in a biohood under sterile conditions.

ECM patterning was performed using microcontact printing (μCP). The basic μCP technique is well established and allows the rapid patterning of biomolecules on a variety of planar substrates using polydimethylsiloxane stamps. The variation employed here used a polydimethylsiloxane stamp to pattern ECM proteins on the polydimethylsiloxane coated glass cover slips to form anisotropic 2D myocardium. ECM proteins were transferred from the stamp to the polydimethylsiloxane thin film by making conformal contact for 1 minute.

C. 1. Vascular Smooth Muscle Seeding and Culture

Human umbilical artery vascular smooth muscle was seeded on thin films at 300 cells/mm$^2$ in complete M199 medium (M199 supplemented with 10% fetal bovine serum (FBS), penicillin, streptomycin, L-glutamine, glucose and vitamin B12). The tissue was cultured in complete M199 for 48 hours, with a single media change at 24 hours. After 48 hours, the cells were serum starved for an additional 48 hours (M199 supplemented with penicillin, streptomycin, L-glutamine, glucose and vitamin B12, but no FBS).

2. Neonatal Rat Ventricular Myocytes Seeding and Culture

Neonatal rat ventricular myocytes were isolated from 2-day old neonatal Sprague-Dawley rats based on published methods. Briefly, ventricles were extracted and homogenized by washing in Hanks balanced salt solution followed by digestion with trypsin and collagenase with agitation overnight at 4° C. Cells were re-suspended in M199 culture medium supplemented with 10% (v/v) heat-inactivated fetal bovine serum (FBS), 10 mM HEPES, 3.5 g/L glucose, 2 mM L-glutamine, 2 mg/L vitamin B-12, and 50 Um' penicillin and seeded on anisotropically patterned FN at a density of 1 million cells per cover slip. Samples were incubated under standard conditions at 37° C. and 5% CO2. Media was exchanged with maintenance media (2% FBS) every 48 h until use. The MTFs were cultured for a period of 4-6 days and then used in the contractility assay.

D. Thin Film Release

Polydimethylsiloxane films were transferred to a petri dish of Tyrode's solution at 37° C. The Petri dish was placed on a stereomicroscope with darkfield illumination and cut into rectangles, parallel with tissue orientation, using a razor blade. Once the Tyrode's solution cools below 35° C., the PIPAAm layer transitions from a hydrophobic state to a hydrophilic state and begins to dissolve. Once the PIPAAm dissolves, films are pulled free of the coverslip with tweezers.

E. Experimental Testing Parameters (Tyrodes, Pacing, Video Recording)

Muscle thin films were transferred to fresh Tyrode's solution in the testing dish (FIG. 1), which is maintained at 37° C. by a peltier heating system. Films were adhered to Teflon coated posts (FIG. 3) by moving them into close contact using tweezers. The films were imaged using a stereomicroscope outfitted with fluorescent imaging capability. Both brightfield and fluorescent images were captured every thirty seconds. In the experiment shown in FIG. 4, four films were treated with 50 nM endothelin-1 followed by 100 μM HA-1077 (fasudil).

F. Image and Stress Analysis

Quantification and analysis of thin film motion was performed using ImageJ (NIH) and MATLAB software. Thresholded fluorescent images (FIG. 4B) were fit to circles whose radii of curvature could be measured (FIG. 4C). Using elasticity theory, the contraction stress necessary to induce the measured changes in curvature were calculated (FIG. 4D).

Results

Muscular thin films were engineered using both cardiomyocytes (cMTFs) and vascular smooth muscle cells (vMTFs). MTFs were constructed by seeding dissociated muscle cells on a multilayer polymer substrate. PIPAAm was spin coated onto a glass coverslip and PDMS is spin coated onto of the PIPAAm layer. The cells were seeded on ECM proteins micropatterned onto the PDMS layer. When the media temperature was lowered below 35° C., the PIPAAm dissolves and the MTF was released and free standing. The radius of curvature of the resulting bilaminate structure is indicative of the stress in the cell layer.

In order to guide alignment of the cells, lines of ECM proteins (FN or LAM) were microcontact printed onto the PDMS. Atomic Force Microscopy (AFM) surface scanning revealed that this ECM pattern is approximately 10-20 nm in thickness. When cells were cultured on the patterned ECM, they spontaneous organize into a contiguous tissue that is aligned with the patterned matrix lines.

In these cells, the long axis of the cell and the nuclear eccentricity parallel the underlying matrix pattern. Fluorescent staining of the fixed tissues revealed that the actin aligns with the underlying matrix in the vascular smooth muscle. In cardiac muscle the sarcomeric Z-lines are perpendicular to the matrix. In both cases, the cytoskeletal architecture indicates that the primary axis of contraction is in the longitudinal direction.

Cardiac ventricular MTFs (cMTFs) were used to measure systolic contraction stress and contractile wave speed in engineered myocardial tissues. The cMTFs were engineered as anisotropic, with uniaxial cellular alignment. Imaging of the Z-disks by immunostaining sarcomeric α-actinin confirmed that alignment of the myofibrils was also anisotropic. The cMTFs were mounted in a bath with a PDMS clamp to firmly hold the cMTF in place during rapid movement and parallel platinum wire electrodes to field stimulate muscle contraction. During diastole, the cMTF may have a baseline curvature due to resting tension in the tissue construct. During contraction, the radius of curvature decreases dramatically, due to cardiomyocytegenerated stress of 13.9 kPa. In this set of experiments, three cMTFs built from the ventricular myocytes harvested from two different rat pup litters produced a mean peak systolic stress of 9.2±3.5 kPa.

The cMTF goes through substantial bending and deformation during contraction, however, because the cMTF is a thin beam, the actual shortening of the cardiomyocytes is <1%, i.e. contraction is isometric. Knowing the stress generated by the cMTF and the elastic modulus of the cardiomyocytes (E=~30 kPa), the unconstrained shortening was estimated as 25% at peak systole. The accurate measurement of the cell and PDMS layer thicknesses are critical for calculating the contraction stress and unconstrained shortening. The elastic modulus of the cell layer, however, has little affect on the calculated stress but does have a significant effect is on the calculation of $\lambda a$, so calculating unconstrained shortening is strongly dependent on accurate cell modulus measurements.

The cMTF system is able to provide an estimate of the contractile wave velocity based on the mechanical deformation of the cMTFs. Tracking the mechanicalwave requires that contraction in the cMTF initiates at one end and propagates to the other. Spontaneous contraction of cMTFs often initiated at the free end and propagated to the base. Tracking the initial position and propagation of maximum curvature along the cMTF from the initiation of contraction until peak systole (uniform curvature) enabled estimation of contractile wave propagation. In the example shown here, the contractilewave speed was 1.875 cm/s, comparable to the velocity of the mechanical wave reported using phase imaging techniques.

Vascular MTFs (vMTFs) were used to demonstrate the potential of this method as a pharmaceutical screening assay. Human umbilical artery VSMCs were engineered as anisotropic monolayers aligned parallel to the long axis of the MTF. The vMTFs were adhered to PTFE coated posts via hydrophobic interaction with the PDMS. This arrangement allowed multiple vMTFs to be viewed concurrently. Here, eight vMTFs were tested using this assay. The fluorosphere doped PDMS could be viewed using fluorescent stereomicroscopy. In this arrangement, the films are easily approximated as circular arcs.

The vMTFs were treated with the endothelium-produced vasoconstrictor endothelin-1 followed by the rho-kinase inhibitor HA-1077, in order to calculate all of the relevant stress states of arterial muscle. The vMTFs had an initial stable baseline curvature indicating that the cells generated a basal stress, defined as the sum of the passive residual stress and the basal contractile tone, of 17.1±1.7 kPa. This value represents the resting tension of the tissue. At time 0, the vMTFs were stimulated with 50 nM ET-1, inducing contraction, which caused a decrease in their radii of curvature as the cell generated stress increased by 5.06±0.75 kPa. Treatment with 100 mM HA-1077, a rho-kinase inhibitor, caused a rapid increase in radius of curvature, due to inhibition of contraction (FIG. 6G), and resulted in a stress of 3.1±0.8 kPa. The HA-1077 dosage is sufficient to inhibit all myosin light chain phosphorylation, so this value represents the residual stress, or the stress generated by the cytoskeletal elements not involved in the contractile apparatus, but which remains after all other loads are removed. By comparing the residual stress following HA-1077 treatment to the pre ET-1 treated tissue, it can be can determined that the vMTFs had a basal contractile tone of 13.1±2.1 kPa. This protocol demonstrates that the vMTFs are able to mimic well documented native vascular behavior and implies that this assay could be used to test the effects of pharmaceutical agents on vascular contractility.

The measured peak systolic stress and constrained shortening of the muscle thin films (MTF) fabricated using neonatal rat ventricular myocytes as described above, were comparable to isometric measurement of isolated papillary muscle. Thus, this MTF system recapitulates both the anisotropic alignment of normal cardiac muscle and physiologically relevant, systolic stress levels.

A unique aspect of the MTF contractility assay is the capability to track local changes in radius of curvature along its length during the cardiac cycle. Further, dyssynchronous contraction when the mechanical wave fails to propagate, or initiates at multiple locations at the same time, resulting in a fluttering cMTF with no discernable deflection can be detected. Thus, a broad range of qualitative and quantitative data can be extracted from the assay by proper frame by frame analysis of the deformation.

The vascular smooth muscle cell MTFs were used to mimic the lamellae of the arterial tunica media. The vMTF assay confirms the presence of functional ET-1 receptors in the engineered smooth muscle and is able to accurately quantify the magnitude of induced contraction. Concurrent monitoring of eight vMTFs contracting and relaxing demonstrates that this technique produces engineered smooth muscle that repeatability responds to pharmacologic stimulation at physiologic stress levels. Moreover, this assay demonstrates that MTFs can provide a method for studying diseases and potential therapeutic interventions, with the potential to significantly scale up the throughput. As an early screening method, this high-fidelity, in vitro contractility assay could be used to directly test the effect of drugs on contractility and potentially decrease the high failure rate of cardiovascular drugs, as currently, novel molecules reaching Phase 1 clinical trials for cardiovascular drugs have a completion rate of less than 20%.

The methods and devices described above and below for the preparation of muscle thin films (MTFs) permit the preparation of a more relevant in vitro model of engineered tissue in that the engineered tissue displays one or more properties of mature tissues, e.g., mature electrophysiology, such as mature action potential morphology, mature ion channel expression, and mature contractility, rather than the immature properties displayed by tissues/cells cultured using previously described methods. Also see, e.g., WO 2008/051265.

Example 2: Cardiac Myocytes and Muscular Thin Film High Content, Enhanced Throughput Device and Use Thereof for Determining a Contractile Function A. Substrate Fabrication Polydimethylsiloxane (PDMS) thin film substrates were fabricated via a multi-step spin coating process. Poly(N-isopropylacrylamide) (PIPAAm) (Polysciences, Inc.) was dissolved at 10 wt % in 99.4% 1-butanol (w/v) and the PIPAAm is deposited in the mid-section of the cover-slip (as shown in FIG. 7A(i)). Sylgard 184 (Dow Corning) polydimethylsiloxane (PDMS) elastomer was mixed at a 10:1 base to curing agent ratio and spun coat on top of the PIPAAm coated glass cover slip (FIG. 7A(ii)). Polydimethylsiloxane-coated cover slips were then cured.

Substrates suitable for the horizontal muscle thin films were also fabricated using Sylgard 184 (Dow Corning) polydimethylsiloxane (PDMS) elastomer mixed at a 10:1 base to curing agent ratio, doped with 0.1% by volume 0.2 μm Fluorospheres (Invitrogen), and spun coated on top of the PIPAAm coated glass cover slip which were then cured.

B. Fibronectin Anisotropic Patterning

The PDMS thin films were coated with an anisotropic layer of fibronectin (FN). In each case, immediately prior to fibronectin treatment, the PDMS-coated cover slips were UV ozone treated for 8 minutes to sterilize the surface and increase hydrophilicity. All subsequent processing was performed in a biohood under sterile conditions.

Anisotropic patterning of fibronectin was performed using microcontact printing (μCP). The basic μCP technique is well established and allows the rapid patterning of biomolecules on a variety of planar substrates using PDMS stamps. The variation employed here used a polydimethylsiloxane stamp to pattern fibronectin on the polydimethylsiloxane coated glass cover slips to form anisotropic 2D myocardium. Fibronectin (50 μg/mL fibronectin in sterile deionized (DI) water) was transferred from the stamp to the polydimethylsiloxane thin film by making conformal contact for 1 minute. The stamp was position in such a way that the pattern is perpendicular to the PIPAAm deposit (FIG. 7A(iv)). The films were then incubated for 15 minutes in low concentration fibronectin (2.550 μg/mL fibronectin in sterile DI water). Following incubation, excess fibronectin was removed by washing 3 times with a sterile phosphate buffer solution (PBS) and then left in PBS until seeding.

C. Cardiomyocyte Seeding and Culture

Neonatal rat ventricular myocytes were isolated from 2-day old neonatal Sprague-Dawley rats based on well known methods. Cells were diluted to a concentration of ~350,000 per mL in seeding media (SM) (M199 media supplemented with 10% FBS), and 3 mL was seeded on each cover slip. After 24 hours incubation, the cover slips were washed 3 times with phosphate buffered saline (PBS) to remove non-adherent cells and recovered with SM. After an additional 24 hours, the media was exchanged with maintenance media (MM) [M199 media supplemented with 2% fetal bovine serum (FBS)] to minimize growth of fibroblasts inevitably present in the primary harvest cardiomyocyte population.

D. Releasing the Films for a Contractility Study

MTFs were released from the cover slip once the cells have formed the appropriate 2D microstructure. The MTFs were either cut out by hand, cut out using a robotic system, pre-cut prior to cell incubation. In one specific example of, e.g., horizontal MTF production, the middle section was cut out, so that only eight rectangles remained in the area that had PIPAAm (see FIG. 7A(vi) for example of the cutout shape). Once the Tyrode's solution cools below 35° C., the PIPAAm layer transitions from a hydrophobic state to a hydrophilic state and begins to dissolve. As the PIPAAm dissolved the middle section cutout was peeled off the substrate with a pair of tweezers. Once the PIPAAm dissolves completely, the contraction of the myocytes pulls the MTF (the remaining rectangles) free from the rigid substrate. In the case of the horizontal MTF, rectangles remain with one end partially fixed to the substrate (FIG. 7A(vii)).

E. Experimental Testing Parameters (Tyrodes, Pacing, Video Recording)

Actuation and observation of multiple MTFs was carried out in a physiologic solution (e.g., normal Tyrodes solution). MTFs were electrically paced using parallel platinum wire electrodes spaced ~1 cm apart and lowered directly into the center of the Petri dish. An external field stimulator (Myopacer, IonOptix) was used to apply a 10-20 V, 10 msec duration square wave between the electrodes at pacing rates from 0.5 to 2 Hz.

F. Video and Image Analysis

Figure 7D:
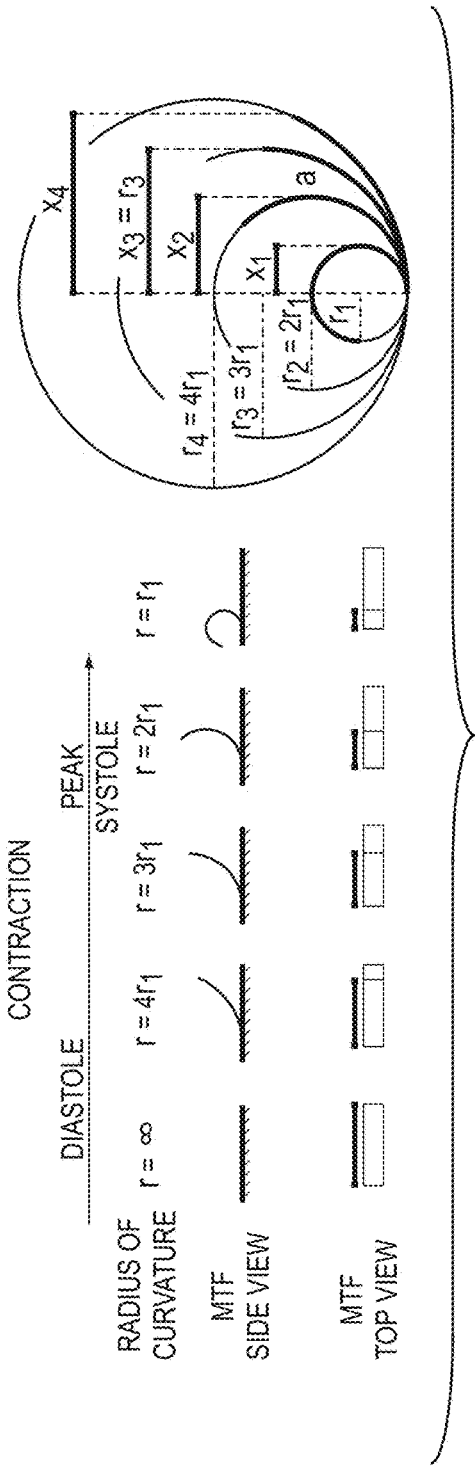

Quantification and analysis of thin film motion was performed using ImageJ (NIH) (FIG. 7B) and MATLAB software. From the thresholded fluorescent images the films length was tracked throughout the contraction and the radius of curvature calculated (FIGS. 7C and 7D). Using elasticity theory, the contraction stress necessary to induce the measured changes in curvature were calculated.

Example 3: Multi-Well Plate Tissue Contractility Device and Assay

This example describes the fabrication of a multi-well plate with micropatterned bottom surfaces wherein each well is used in a horizontal muscular thin film (MTF) assay (see, e.g., FIG. 9A). The micropatterned multi-well plates are especially amenable to assays using automatic imaging of the MTFs in, e.g., a GE InCellAnalyzer.

The multi-well plate with MTF assay, can be used for biomechanical measurements of myocyte contraction properties. In this device the tissue constructs remain partially fixed to a hard substrate, such as the glass bottom of the multi-well plate. This invention is designed for use with polymeric thin films (PCT Publication No. WO 2008/051265 A2), but could be used with any differentially stressed polymer or tissue construct. In this assay the thin films bend up from the viewing (horizontal) plane unlike the original thin film assay in which a single film bends in the viewing plane. The number of wells is limited by the size of the desired films (the films have to be large enough for the cells to constitute a tissue), with a film of at least 1.2 mm×2.4 mm any 6, 12, 24, 48, 96 well plates can be used. The assay may be utilized to measure biomechanical forces due to a number of stimuli including, but not limited to, contraction, osmotic swelling, structural remodeling and tissue level pre-stress. It is possible to further automate the assay by methods that include, but are not limited to, cookie cutter razors that would come down into the wells to cut the films, programmable lasers that cut the films, and automatic aspiration pipettes to aspirate out unwanted film sections. The biomechanical responses due to paracrine signaling events can also be studied through the addition of a co-culture system, making the device attractive for studying cell-to-cell drug effects.

In the context of the present experiment a section of glass was cut to match the dimensions of the multi-well plate skeleton section of glass (7.5 cm×11 cm) and was covered with a protective film (to preserve the optical clarity of the substrate during later fabrication steps), by lowering the protective film onto the glass covered with 200 proof ethyl alcohol, and removing, e.g., using pressure, the excess ethanol from under the film. This process was repeated for the other side of the glass and then islands corresponding to a portion of the wells were cut out of the top protective film. Then, a temperature sensitive polymer, specifically poly(N-isopropylacrylamide) (PIPAAm), was deposited in a thin layer onto the open glass islands and the top protective film layer was peeled off. A biopolymer, specifically polydimethylsiloxane (PDMS), was deposited in a layer, e.g., by spin coating, (~5-25 μm) on top of the whole glass, with the bottom protective film preventing back-splatter of the PDMS onto the glass. The PDMS was allowed to completely cure overnight and the bottom protective film was peeled off. A biopolymer, e.g., extracellular matrix protein (ECM), e.g., fibronectin (FN), was stamped (micro-contact printed) in a pattern onto the PDMS.

In parallel, a second section of glass was cut to match the dimensions of the multi-well plate skeleton (7.5 cm×11 cm). The second glass section was then spin coated with a layer of PDMS, which was immediately brought into contact with and lifted off of the bottom of the multi-well plate skeleton leaving behind a thin layer of PDMS on the bottom of the multi-well plate skeleton. At this point, the ECM patterned PDMS-glass base was pressed into contact with the PDMS coated bottom of the multi-well plate skeleton (24 well A-Plate GBMP Black Porvair Sciences Ltd.), creating a PDMS seal between the wells. To provide additional liquid load bearing capacity, a sealant was painted around the outer border, further adhering the glass base to the multi-well plate skeleton. The plate was then placed in a humid warm (37° C.) incubator overnight to complete the PDMS seal curing while providing the humidity necessary to maintain proper ECM molecule activity.

Phenol red was placed inside various wells of the plate to confirm that the seal between wells did not leak. Following a 48-hour incubation, the phenol red had not spread to adjacent wells demonstrating that the seals of the wells were intact (see, e.g., FIG. 9B).

Contractile cells, specifically cardiomyocytes, were seeded onto the ECM inside each well. For the multi-well plate, the MTFs inside the film with the cells were cut and the unwanted regions peeled off the glass in each well. As a result a single rectangle of film remained attached to the glass at one edge only in each well. The dynamics of these tissue constructs was recorded. The cells in the plate can be fixed and immuno-stained to study cell structure (see, e.g., FIG. 9C).

Example 4: High-Throughput Multi-Tissue Contractility Device and Assay

A multi-tissue contractility assay can be used, for example, to qualitatively compare contractions of two tissue types, to compare the effect of one tissue response in proximity to another tissue, or for biomechanical measurements of myocyte contraction properties.

The substrates for use in a multi-tissue contractility assay are made as described below and herein. In this device, the tissue constructs remain partially fixed to a rigid substrate, e.g., the glass bottom of the multi-well plate, and bend up from the viewing (horizontal) plane. The rigid substrate is made in such a manner that it can be split after the ECM has been patterned into as many parts, at least two, as the number of tissues. Different types of cells are then cultured on the substrate or different types of micropatterning can be patterned onto the substrate, e.g., line patterns, anisotropic monolayers, or isotropic monolayers. The assay could be utilized to measure biomechanical forces due to a number of stimuli including, but not limited to contraction, osmotic swelling, structural remodeling and tissue level pre-stress. The biomechanical responses due to paracrine signaling events can also be studied, making the device attractive for studying cell-to-cell drug effects.

One benefit of the methods described below is the ability to maintain even thickness of the sacrificial polymer layer from island to island, thus, yielding more consistent devices.

In the context of the present experiment and as depicted in FIGS. 10 and 11, a section of glass (7.5 cm×11 cm) was covered with a protective film, by lowering the protective film onto the glass covered with 200 proof ethyl alcohol, and removing, e.g., using pressure, the excess ethanol from under the film. This process was repeated for the other side of the glass and then islands corresponding to the desired size of assay were cut out of the top film. A temperature sensitive polymer, specifically poly(N-isopropylacrylamide) (PIPAAm), was then deposited as a thin layer onto the open glass islands, then the top protective film layer was peeled off. A polymer, specifically polydimethylsiloxane (PDMS), was deposited in a layer (~5-25 μm) on top of the whole glass, with the bottom protective film preventing back-splatter of the PDMS onto the glass. The PDMS was allowed to completely cure overnight and the bottom protective film was peeled off. A mask, printed on transparencies was used to cut the glass into desired shapes. An extracellular matrix protein, such as (ECM) fibronectin (FN), was stamped in the pattern depicted in FIGS. 10 and 11 onto the PDMS. The glass was cut in between the two PIPAAm islands. The two pieces of glass were treated with different agents (Pluronic F127 blocking and low concentration FN background). Contractile cells, such as cardiomyocytes, were seeded onto the ECM. The cells formed lines in the first (Pluronics treated) tissue, and anisotropic monolayers in the second tissue (low concentration FN treated). The cover-slips were then combined and the films cut, with the unwanted regions peeled away. As a result a single rectangle of film remained attached to the glass at one edge only. The dynamics of these tissue constructs were recorded.

Example 5: Vascular Smooth Muscle Thin Film High Content, Enhanced Throughput Device and Use Thereof for Determining a Contractile Function A. Substrate Fabrication A section of glass (7.5 cm×11 cm) was covered with a static vinyl protective film by lowering the protective film onto the glass, and removing, e.g., using pressure, the all air bubble from under the film. This process was repeated for the other side of the glass and then islands corresponding to the desired size of assay were cut out of the top film.

Polydimethylsiloxane (PDMS) thin film substrates were fabricated via a multi-step spin coating process. Poly(N-isopropylacrylamide) (PIPAAm) (Polysciences, Inc.) was dissolved at 10 wt % in 99.4% 1-butanol (w/v) and was then deposited as a thin layer onto the open glass islands, then the top protective film layer was peeled off. Sylgard 184 (Dow Corning) polydimethylsiloxane (PDMS) elastomer was mixed at a 10:1 base to curing agent ratio doped with 0.1% by volume 0.2 mm Fluorospheres (Invitrogen), and spun coated on top of the PIPAAm coated glass cover slip which was then cured. The next day, the bottom protective film was peeled off. A mask, printed on transparencies was used to cut the glass into desired shapes.

B. Fibronectin Anisotropic Patterning

The PDMS thin films were coated with an anisotropic layer of fibronectin (FN). In each case, immediately prior to fibronectin treatment, the PDMS-coated cover slips were UV ozone treated for 8 minutes to sterilize the surface and increase hydrophilicity. All subsequent processing was performed in a biohood under sterile conditions.

Anisotropic patterning of fibronectin was performed using microcontact printing (mCP). The basic mCP technique is well established and allows the rapid patterning of biomolecules on a variety of planar substrates using PDMS stamps. The variation employed here used a polydimethylsiloxane stamp to pattern fibronectin on the polydimethylsiloxane coated glass cover slips to form anisotropic 2D myocardium. Fibronectin (50 μg/mL fibronectin in sterile deionized (DI) water) was transferred from the stamp to the polydimethylsiloxane thin film by making conformal contact for 1 minute. The stamp was positioned in such a way that the pattern is perpendicular to the PIPAAm deposit. Following stamping, excess fibronectin was removed by washing 3 times with a sterile phosphate buffer solution (PBS) and then left dry until seeding.

C. Neonatal Rat Ventricular Myocytes Seeding and Culture

Neonatal rat ventricular myocytes were isolated from 2-day old neonatal Sprague-Dawley rats based on published methods. Briefly, ventricles were extracted and homogenized by washing in Hanks balanced salt solution followed by digestion with trypsin and collagenase with agitation overnight at 4° C. Cells were re-suspended in M199 culture medium supplemented with 10% (v/v) heat-inactivated fetal bovine serum (FBS), 10 mM HEPES, 3.5 g/L glucose, 2 mM L-glutamine, 2 mg/L vitamin B-12, and 50 Um' penicillin and seeded on anisotropically patterned FN at a density of 1 million cells per cover slip. Samples were incubated under standard conditions at 37° C. and 5% CO2. Media was exchanged with maintenance media (2% FBS) every 48 h until use. The MTFs were cultured for a period of 4-6 days and then used in the contractility assay.

D. Releasing the Films for a Contractility Study

MTFs were released from the cover slip once the cells have formed the appropriate 2D microstructure. The MTFs were either cut out by hand, cut out using a robotic system, pre-cut prior to cell incubation. In one specific example of, e.g., horizontal MTF production, the middle section was cut out, so that only six rectangles remained in the area that had PIPAAm). Once the Tyrode's solution cools below 35° C., the PIPAAm layer transitions from a hydrophobic state to a hydrophilic state and begins to dissolve. As the PIPAAm dissolved the middle section cutout was peeled off the substrate with a pair of tweezers. Once the PIPAAm dissolves completely, the contraction of the myocytes pulls the MTF (the remaining rectangles) free from the rigid substrate. In the case of the horizontal MTF, rectangles remain with one end partially fixed to the substrate.

E. Experimental Testing Parameters (Tyrodes, Pacing, Video Recording)

Actuation and observation of multiple MTFs was carried out in a physiologic solution (e.g., normal Tyrodes solution). The horizontal MTFs (hMTFs) fabricated with vascular smooth muscle cells in the presence of fluorescent beads were treated with the endothelium-produced vasoconstrictor endothelin-1 (ET-1) followed by the rho-kinase inhibitor HA-1077.

Figure 12:
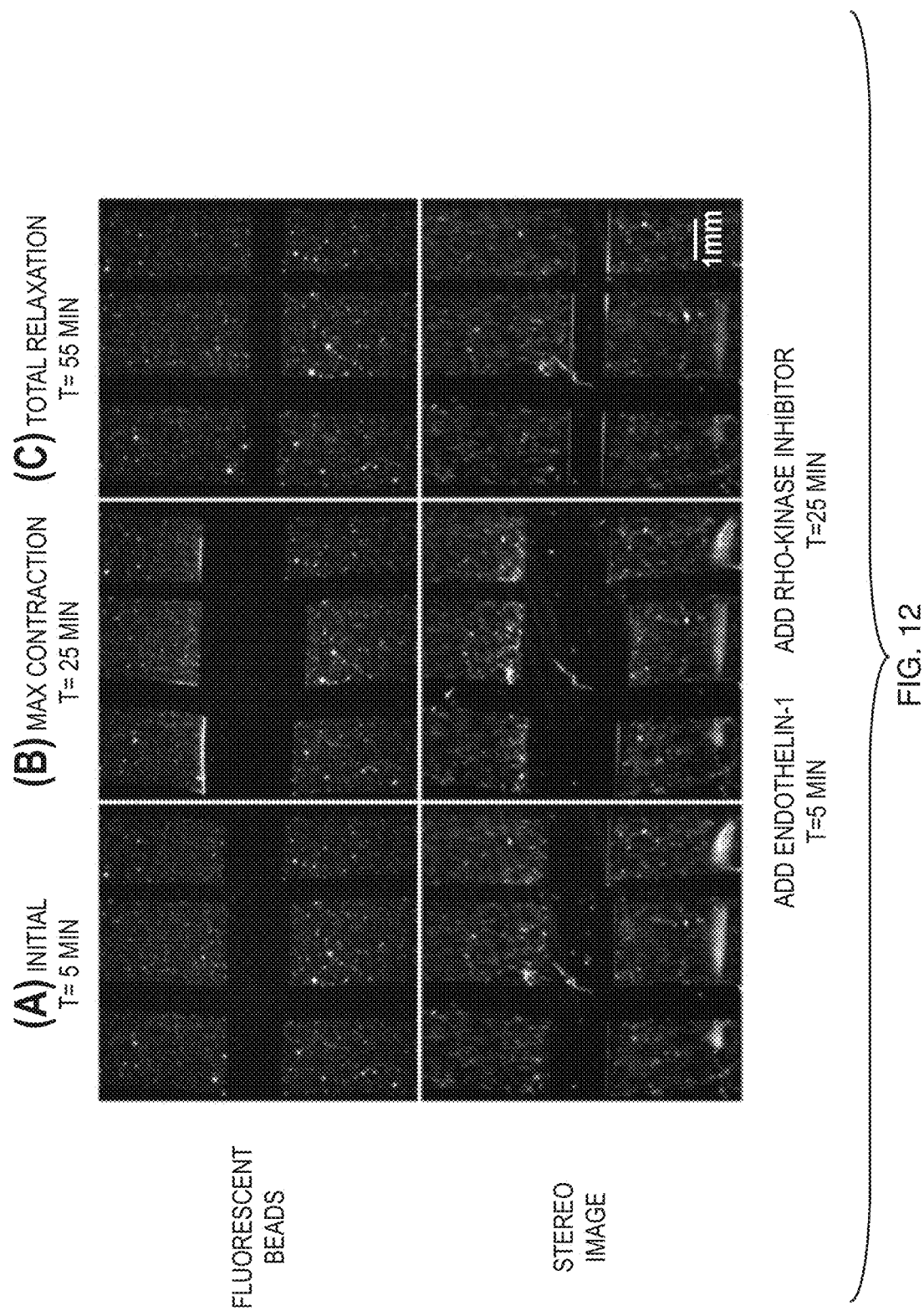
FIG. 12 contrasts the use of fluorescent microscopy and the use of brightfield stereo microscopy of vascular smooth muscle (VSM) horizontal MTFs during an assay of the invention as described in Example 5. The top row depicts fluorescent microscopy photographs of VSM horizontal MTFs comprising fluorescent beads embedded in the PDMS film. The bottom row shows brightfield stereo microscopy images of the same films. (A) Photographs taken 5 minutes after the start of the experiment, the films are slightly bent up from the glass due to the initial contraction of VSM. (B) Photographs taken 20 minutes after addition of the vasoconstrictor (Endothilin-1), which causes the VSM to contract and the films to bend up from the glass. (C) Photographs taken 30 minutes after addition of a rho-kinase inhibitor, which causes the VSM to completely relax and the films to lie flat on the glass. The contrast of the use of fluorescent microscopy shows that fluorescent images may be used to eliminate noise that may be present in regular brightfield images.
Figure 14:
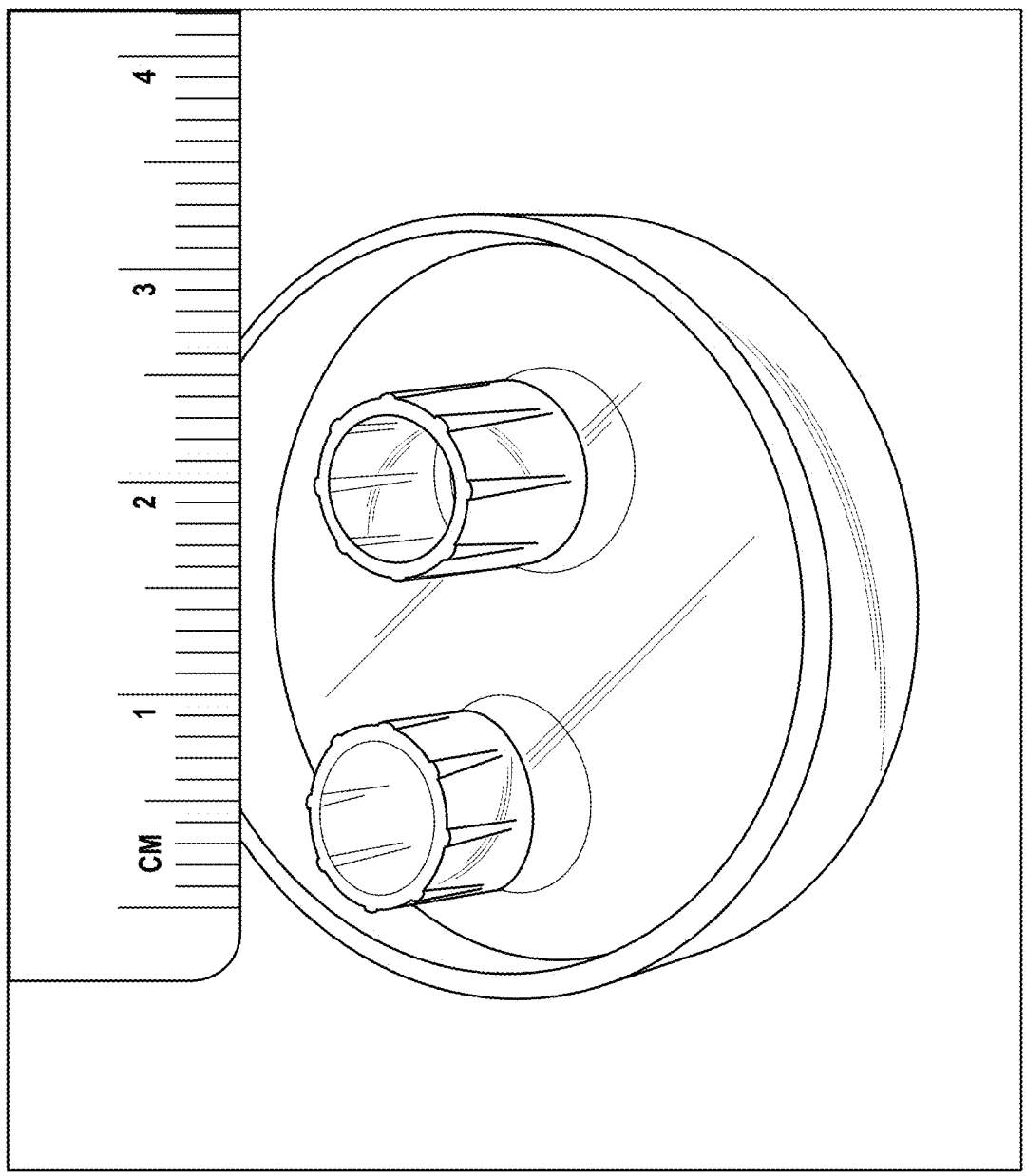
FIG. 14 is a photograph of one embodiment of the devices of the invention depicting a tri-laminate fluidic chamber comprising an MTF and useful in the methods of the invention, such as, a contractility assay. The device is constructed from 1.5 mm PMMA. Number 1 glass cover slips comprise the top and bottom layers. Muscular Thin Films (MTFs) were cut into approximately 1 mm×3 mm cantilevers before assembling the device.
Figure 15:
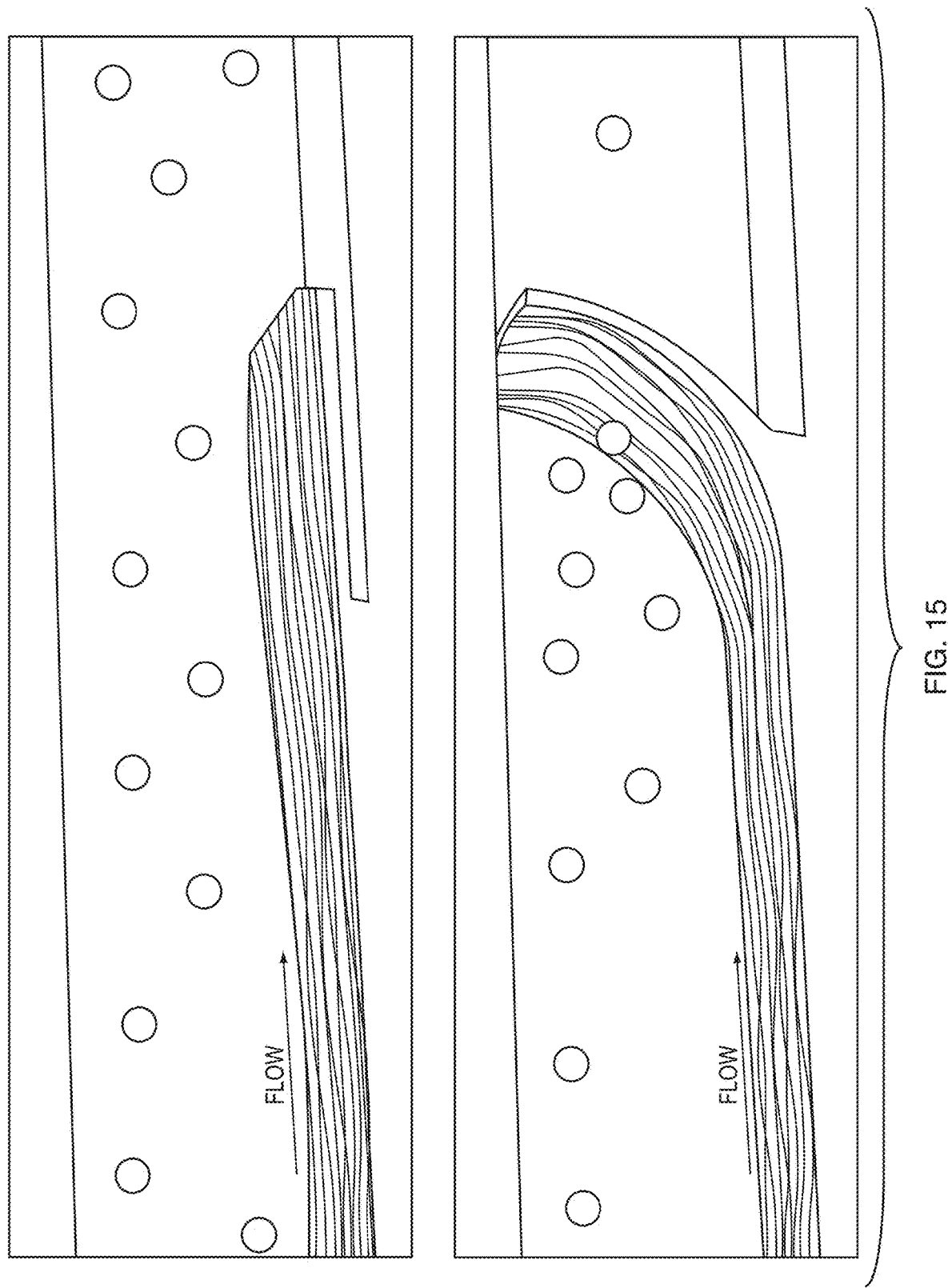
FIG. 15 depicts an anisotropic MTF in a microfluidic chamber exposed to a drug (circles) in diastole (top) and at peak systole (bottom).
Figure 16:
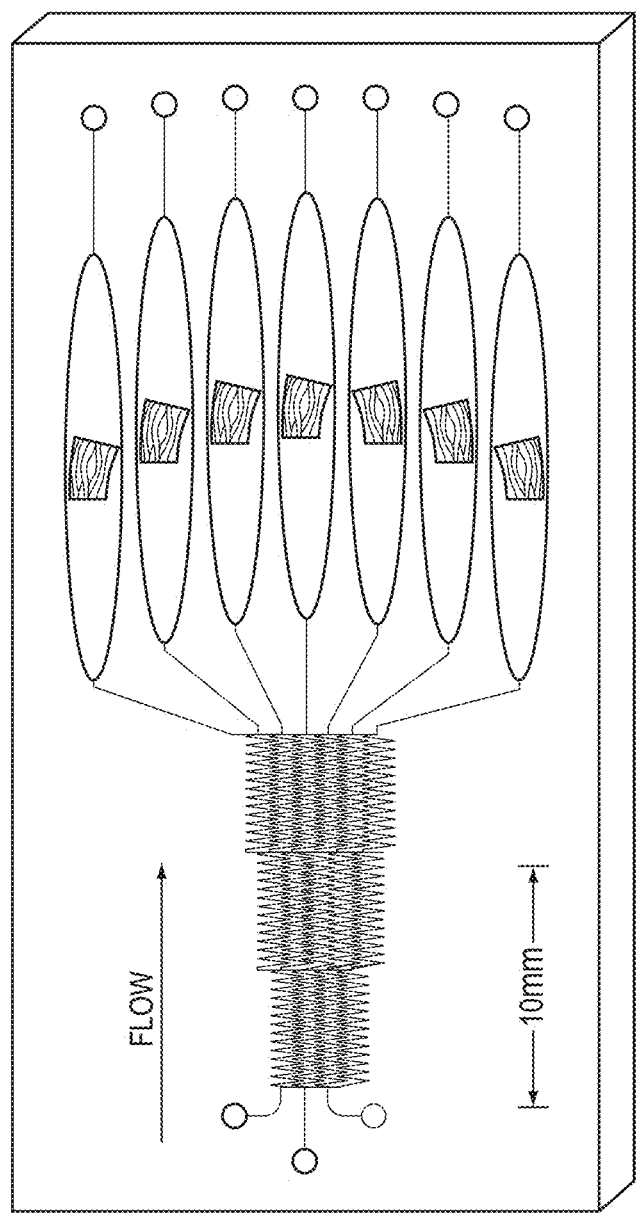
FIG. 16 is a schematic representation of a gradient generation microfluidic device to assay drug-dose responses. The PDMS-based device (25 mm×75 mm), receives three fluids at left, the highest drug dose in the top channel, a decreased drug concentration in the middle channel, and isotonic buffer in the bottom channel. The microfluidic devices generate drug gradients which are then separated and transferred into wide (2.5 mm) channels to decrease fluid velocity in order to simplify fluid dynamics calculations for horizontal MTF (hMTF) assays.
Figure 17:
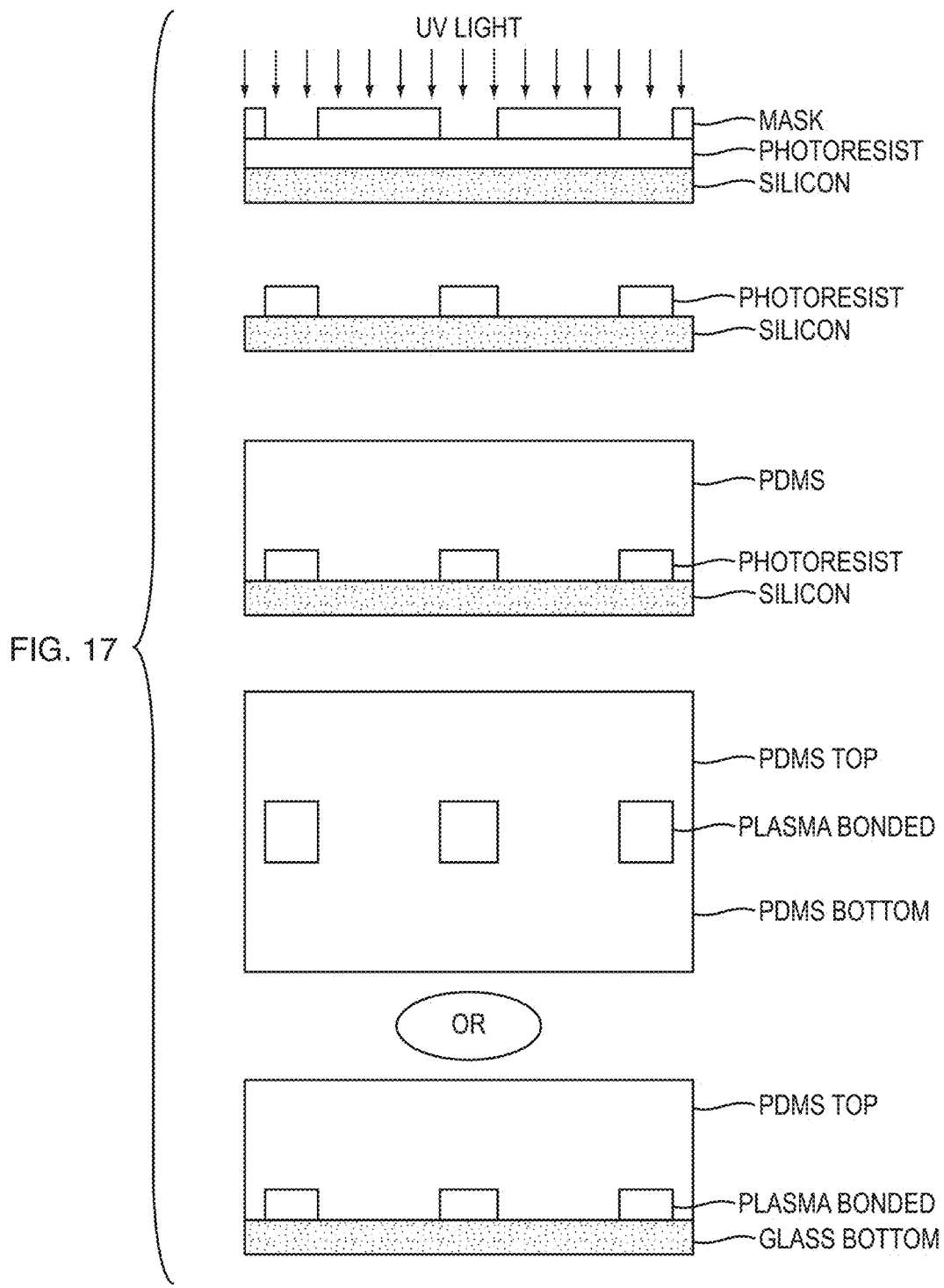
FIG. 17 is a schematic representation illustrating soft lithography-based microfluidic fabrication of one embodiment of the devices of the invention. A negative photoresist underneath a mask is exposed to UV light crosslinking the exposed photoresist. The un-crosslinked photoresist is developed, leaving a negative mold. PDMS elastomer is poured into the photoresist/silicon mold and peeled away after curing. The patterned PDMS can be either bonded to another PDMS pattern or planar polymeric surface via plasma-treated surface covalent bonding.
Figure 18:
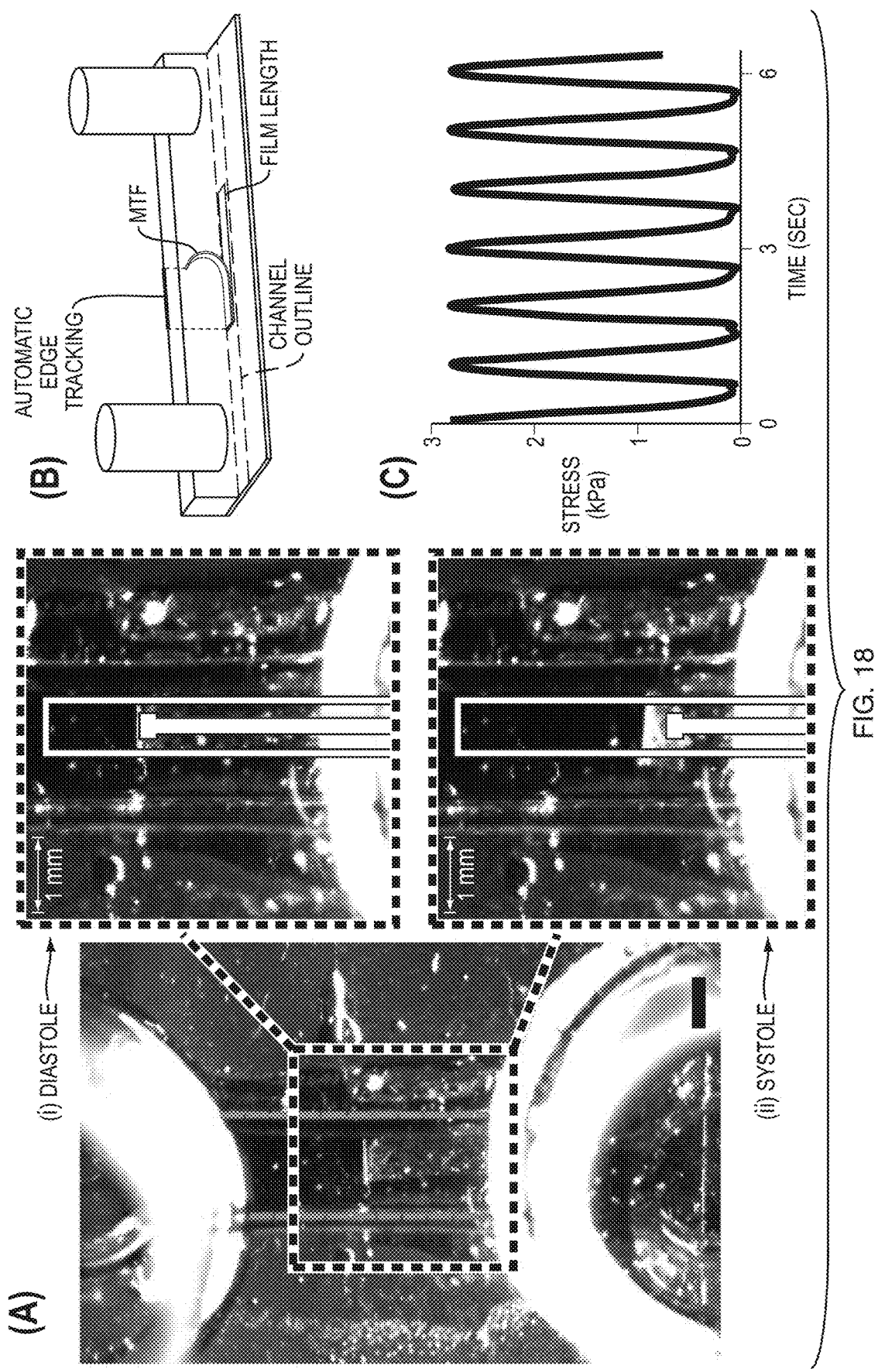
FIG. 18 is a photograph of the top view of a microfluidic channel with a hMTF inside the channel. The inflow, outflow channel are outlined with a dashed light gray line. The myocytes are paced inside the channel and the diastolic and peak systolic positions of the hMTF are shown inside the boxes, with the film edge tracked (light gray) and the film length outlined (black). (B) Schematic showing the microfluidic channel with a hMTF inside, MTF film in medium gray, initial length outline in black, edge tracking in light gray, channel outline in light gray. (C) Filtered stress profile read-out from this film in kPa.

The hMTFs had an initial stable baseline curvature (FIG. 12) indicating that the cells generated a basal stress. At time 0, the hMTFs were stimulated with 50 nM ET-1, inducing contraction, which caused a decrease in their radii of curvature (FIG. 12). Treatment with 100 mM HA-1077, a rho-kinase inhibitor, caused a rapid increase in radius of curvature, due to inhibition of contraction.

This protocol demonstrates that the hMTFs are able to mimic well documented native vascular behavior and implies that this assay could be used to test the effects of pharmaceutical agents on vascular contractility.

F. Video and Image Analysis

Quantification and analysis of thin film motion was performed using ImageJ (NIH) and MATLAB software. From the thresholded fluorescent images the length of the projection of the film on the horizontal plane was tracked throughout the contraction and the radius of curvature calculated. Using elasticity theory, the contraction stress necessary to induce the measured changes in curvature were calculated.

Examples 6-8 describe the preparation and use of muscle organs-on-a-chip.

Example 6: Heart-On-A Chip

Multiple pharmaceutical agents are hampered by cardiotoxcity and these can be broken down into three basic categories.

(1) Metabolic: Antibody-based medications such as Trastuzumab, which is used to treat HER2+ breast cancer, are known to affect ATP production in myocytes through adverse effects on mitochondria (Force T, et al. (2007) Cancer 7(5):332).

(2) Structural: Anti-proliferative agents such as doxorubicin, which is used for a wide variety of malignancies, adversely affects myocyte growth and mass maintenance (Zhu W, et al. (2008) Circulation:CIRCULATIONAHA. 108.799700).

(3) Ion Channel (Arrhythmia-inducing): hERG channel binding of many drugs (e.g. albuterol) increases action potential duration, leaving the heart susceptible to arrhythmia (long QT syndrome)

Although various drug toxicities might affect myocytes with distinct mechanisms, all will adversely affect cardiac contractility and ultimately the ability of the heart to pump blood. Thus, by measuring the contractility and electrophysiological output of the organ, one may quantitatively measure the impact of various agents on heart performance.

For example, drugs such as doxorubicin (anthracycline family of chemotherapeutics), which display cardiotoxic effects primarily by inducing dilated cardiomyopathy, predominately affect the ventricles with some left atrial involvement. Trastuzumab, a monoclonal antibody to HER2 receptor used for the treatment of (HER2+) breast cancers, has been shown to decrease left ventricular ejection fraction.

Since the above mentioned drugs show primarily ventricular toxicity, it would be useful to be able to mimic the contractile action of these chambers in vitro. Accordingly, there is a need in the art for robust in vitro systems that can recapitulate the heart and can provide a platform to screen a large number of compounds for toxicity, a feat not possible with in vivo models.

The present example demonstrates fulfillment of these needs by construction of a microfluidic device that can simultaneously measure electrophysiology and contractile performance of engineered myocardial tissues.

In one embodiment, this example describes the preparation of fluidic, e.g., millifluidic and/or microfluidic, devices comprising a physiologically relevant in vitro heart muscle system which incorporates the myocardium.

In particular, this example describes the preparation of fluidic, e.g., millifluidic and/or microfluidic, devices comprising mature human cardiomyocytes of different origins (i.e., ventricular, atrial, etc) on 2D PDMS substrates or hydrogel substrates, e.g., micro-contact printed and/or micromolded alginate and/or gelatin substrates. These devices integrate both a muscle tissue chamber, e.g., a muscle thin film chamber and/or a microcontact printed and/or micromolded hydrogel muscle tissue chamber for contractility measurements and a low volume electrophysiological ("EPhys") readout chamber (see, e.g., FIGS. 22 and 28).

In another embodiment, this example describes the preparation of fluidic, e.g., millifluidic and/or microfluidic devices comprising mature human cardiomyocytes of different origins (i.e. ventricular, atrial, etc) on a swiss cheese-like polyurethane membrane, (where muscular contraction causes deformation of the holes within the membrane) integrated with a low volume electrophysiological readout chamber (see, e.g., FIG. 23).

The foregoing devices are referred to herein as a "heart-on-a-chip". In one embodiment, a heart-on-a-chip is further integrated, e.g., via fluidic, e.g., microfluidic, connection, with additional organs-on-a-chip, e.g., lung chips to mimic breathing lung, liver chips to mimic metabolic liver, kidney chips to mimic flowing kidney, gut chips to mimic peristalsing gut, lung airway smooth muscle chips to mimic reactive airway, skeletal muscle chips to mimic contracting skeletal muscle, skin chips to mimic skin barrier, brain chips to mimic blood-brain barrier, testis chips to mimic reproductive/endocrine testis and bone marrow chips to mimic self-renewing bone marrow.

In certain embodiments, one chamber comprises horizontal strips of muscle tissue, e.g., MTFs (also referred to as the MTF chamber) and contractility of the tissue is read out via device to track muscle tissue deformation/membrane deformation. The device may be e.g., an optical signal capturing device or a device for translating contractility into an electrical or magnetic signal, e.g., piezoresistive, piezoelectric, or strain sensor, e.g., embedded within the thin film and/or hydrogel. In certain embodiments, a second chamber comprises a monolayer of isotropically and/or anisotropically aligned muscle tissue (also referred to as the EPhys chamber) and electrophysiological recordings are taken via ECG, e.g., a multi-lead ECG. In other embodiments, one chamber comprises micro-contact printed and/or micromolded hydrogels comprising a muscle tissue (e.g., cardiac tissue) (also referred to as the MTF chamber) and contractility of the tissue is read out via a device to track deformation/membrane deformation, e.g., an optical signal capturing device or a device for translating contractility into an electrical or magnetic signal, e.g., piezoresistive, piezoelectric, or strain sensor, e.g., embedded within the thin film and/or hydrogel. In still other embodiments, a second chamber comprises micro-contact and/or micromolded hydrogels comprising a muscle tissue (e.g., cardiac tissue) (also referred to as the EPhys chamber) and electrophysiological recordings are taken via a one lead ECG. (See, e.g., FIG. 32). The tissues from one or both chambers may be further used to determine the effect of various test compounds on the expression and/or activity of various markers of muscle damage such as creatine kinase and troponin.

The benefits of micro-contact and/or micromolded hydrogels in such fluidic devices is that the hydrogel stiffness may be finely tuned to mimic the mechanic properties of both healthy and diseased tissue, e.g., cardiac tissue by, for example, modulating the concentration of cross-linking agent, e.g., $CaCl_2$ and transglutaminase (see, e.g., FIGS. 32-35).

Figure 38:
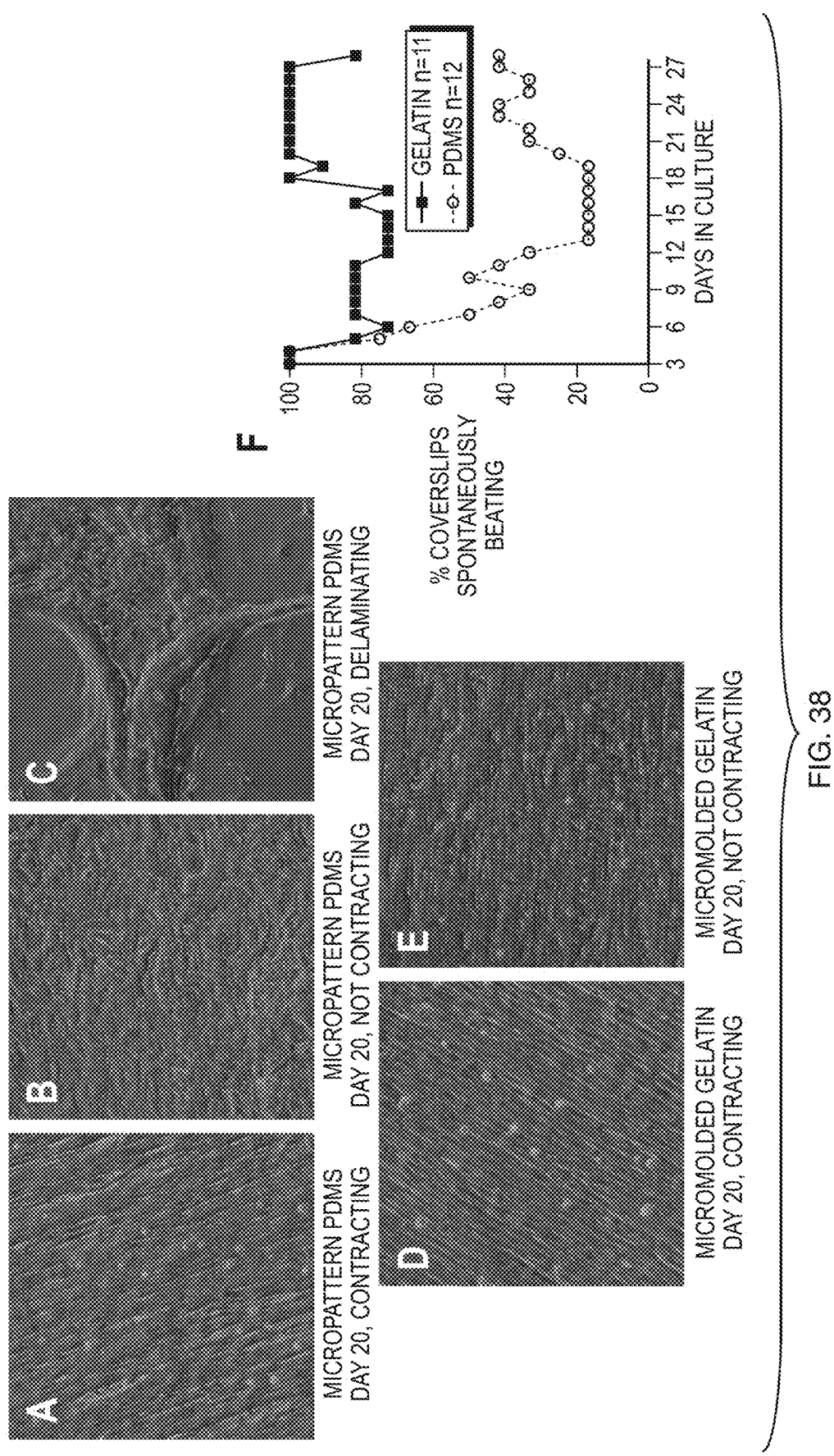
FIG. 38 depicts anisotropic cardiac monolayers on micro-patterned PDMS (e.g., MTFs) (A-C) and micromolded hydrogel, e.g., gelatin (D-E). Spontaneously contracting (A, D) and non-contracting (B, E) monolayers were observed on both substrates. Over extended periods of culture, monolayers of cells often delaminated on PDMS (C). (F) Quantification of the number of coverslips spontaneously beating over 28 days demonstrate that gelatin maintains long-term functionality of cells as compared to MTFs.
Figure 39:
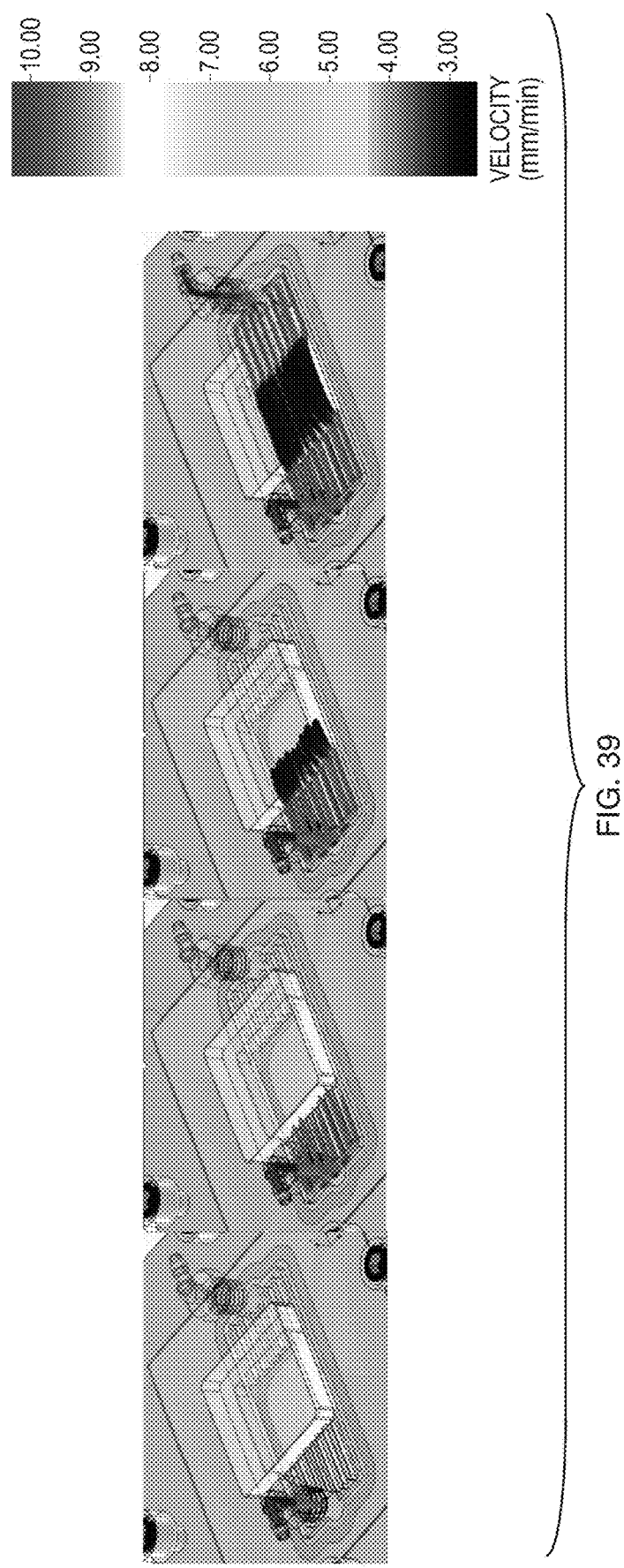
FIG. 39 schematically depicts image sequences from computational fluidic simulations demonstrating laminar fluid flow in a 1 ml fluid chamber with a single flow channel and which contains arrays of 1-20 muscular thin films and/or hydrogel engineered muscle tissues. In order to achieve laminar flow under these conditions, small channels were designed between the inlet and the chamber (and conversely between the chamber and the outlet) wherein the further the liquid travels laterally from the inlet, the wider the channel. This effect of channel widening balances the fluidic front, which is necessary to achieve even drug dosing for the tissues.
Figure 40:
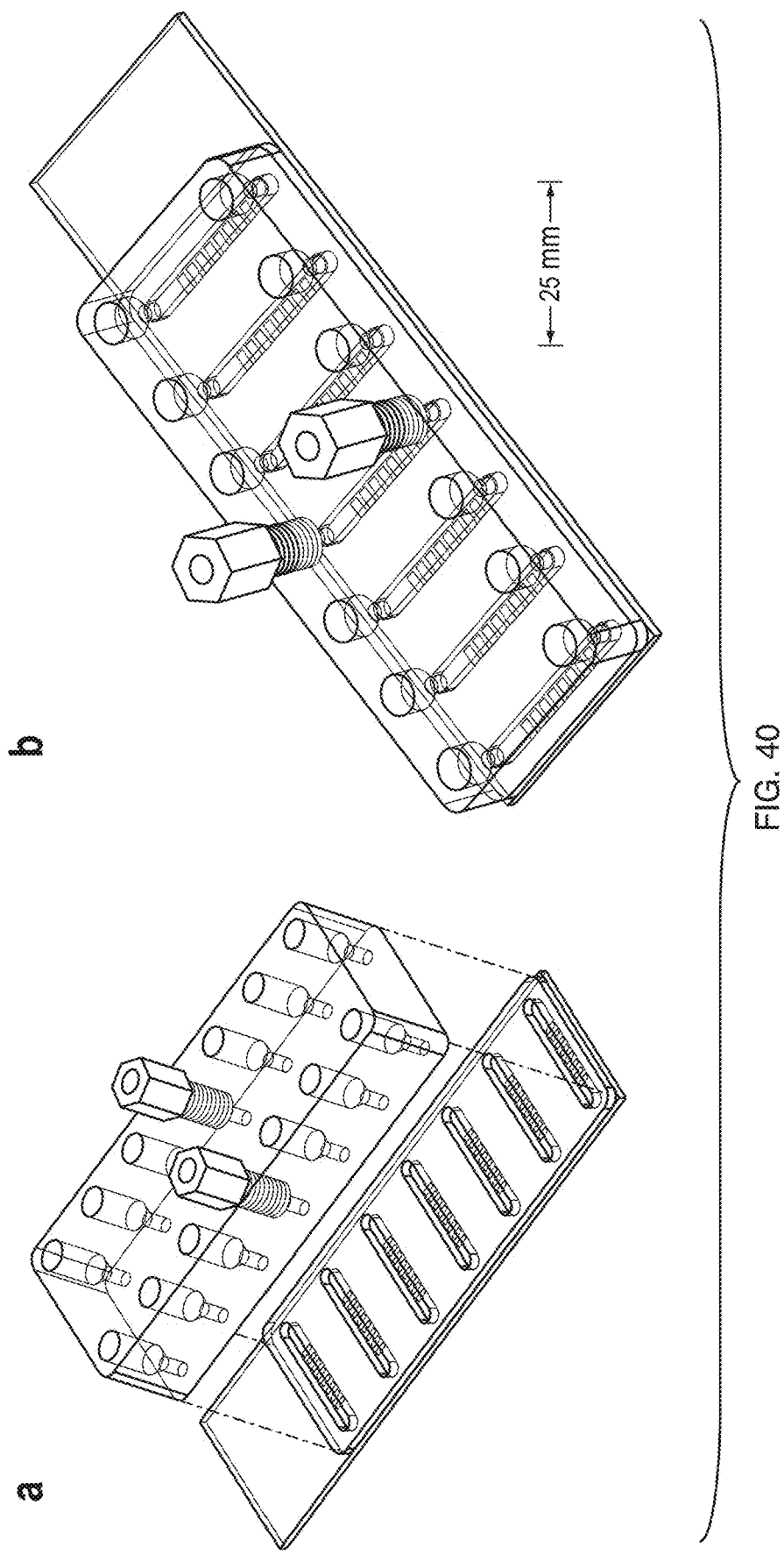
FIG. 40 is a CAD render of a 25×75 mm muscle-on-a-chip design which is comprised of 7 independent flow channels. Each flow cell can contain 1-10 MTF and/or hydrogel engineered tissue replicate. A manifold, depicted above the chip, allows for the simultaneous connections of any connections to the chip (fluidic, pneumatic, and electric). B) A chip with an attached manifold. In this embodiment, threaded fittings are screwed into the manifold to facilitate the leak-free connection of liquid or air tubing. Both the chip layers and the manifold may be made from any suitable synthetic or natural polymers such as glass, polycarbonate, Poly(methyl methacrylate) (PMMA), Polydimethylsiloxane (PDMS), Cyclic Olefin Copolymer (COC), Cyclic Olefin Polymer (COP), and Polyether ether ketone (PEEK).
Figure 41:
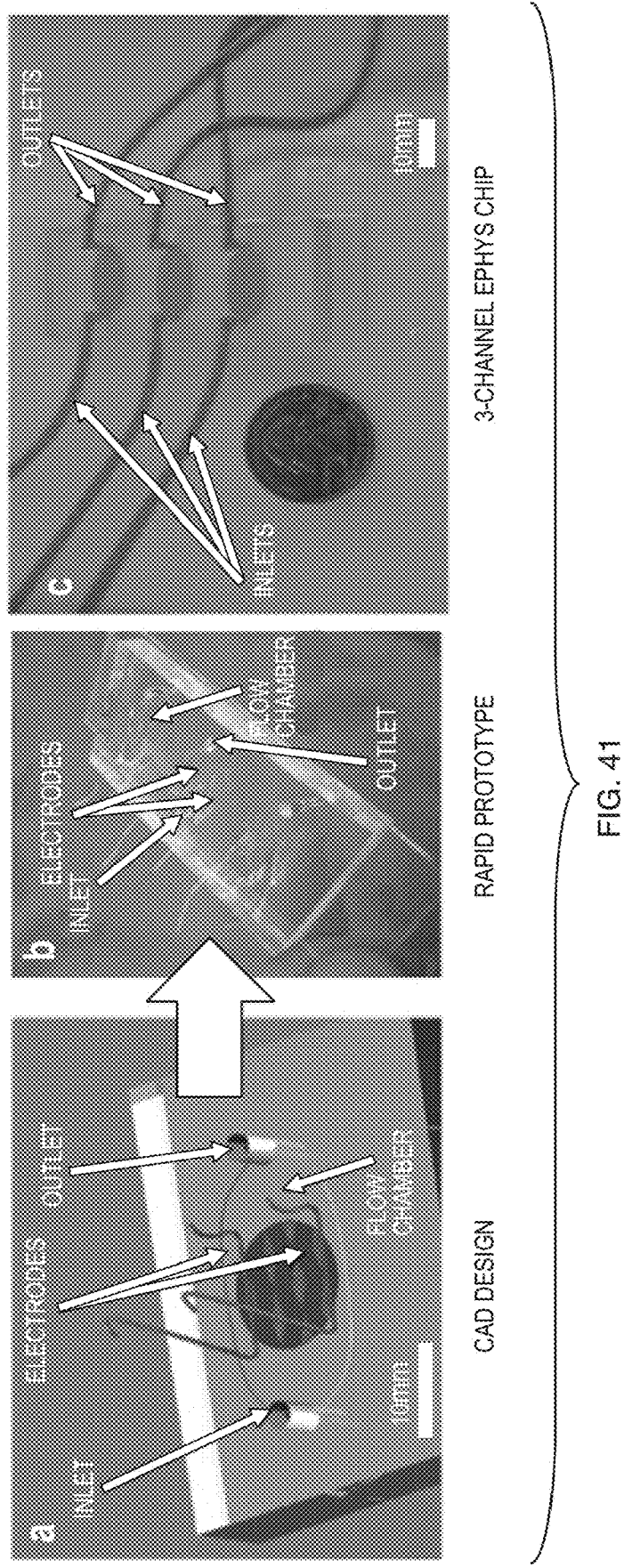
FIG. 41 is a CAD render of a single electrophysiology (EPhys) chamber which is comprised of a patterned hydrogel, anisoptropically aligned cells, electrodes, and fluidic ports. b) A fabricated prototype of the design constructed using soft lithography. c) Allura red dye is added to a 25×75 mm chip which contains three independent channels, illustrating the flow paths for introducing drugs and linking the muscle chips to other chips.

The micro-contact and/or micromolded hydrogels when used in the devices of the invention also permit longer-term culture of muscle tissue, e.g., in a closed system, e.g., a microfluidics device. For example, MTFs remain viable and spontaneously contract for about 5, 6, 7, 8, 9, 10, 11, or 12 days, while micro-contact printed and/or micromolded hydrogels comprising muscle tissue remain viable and spontaneous contract for at least about 14, 15, 16, 17, 18, 19, 20, 21, 22, 23, 24, 25, 26, 27, 28, 29, 30, 31, 32, 33, 34, 35, or 36 days (see, e.g., FIGS. 34, 35, and 38).

Furthermore, micro-contact and/or micro-molded hydrogels do not absorb drugs applied to the muscle tissue and, therefore, do not interfere with assessment of the effect of the drug on a muscle tissue function.

Culture/Maturation of Human Cardiomyocytes

Figure 20:
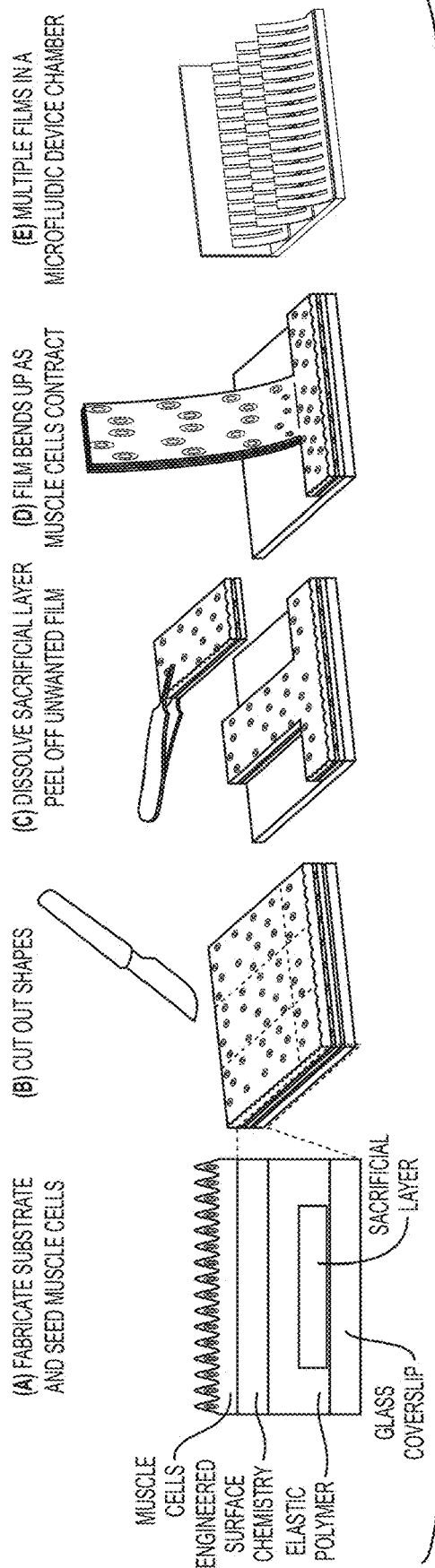
FIG. 20 schematically depicts the assembly steps for the muscular thin film contractility assay based on a PDMS thin film in a fluidic chamber.
Figure 21:
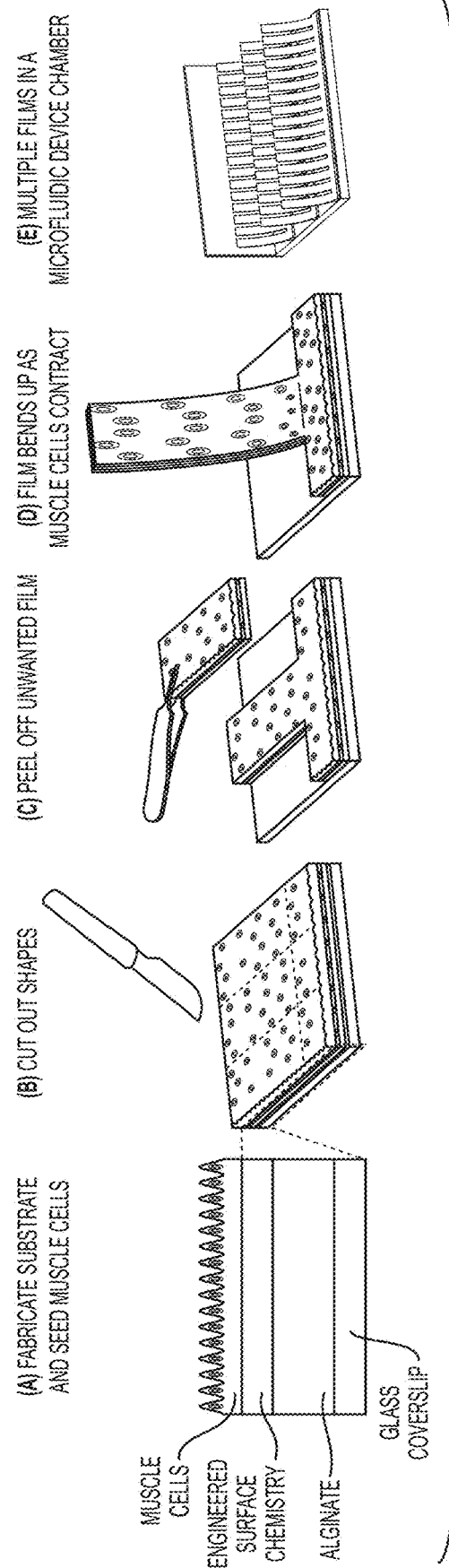
FIG. 21 schematically depicts the assembly steps for the muscular thin film contractility assay based on a patterned alginate thin film in a fluidic chamber.

Human cardiomyocytes are commercially available from, for example, Axiogenesis, CDI, Vistagen, Coriell, Reprocell. Aligned monolayers of muscle cells are cultured on microcontact printed PDMS substrates, microcontact printed polyurethane membranes, and/or micro-contact printed and/or micromolded hydrogel substrates, e.g., microcontact printed and/or micromolded gelatin and alginate substrates Microphysiological Heart Chip Design and Fabrication For the MTF chamber, laser engraving processes are used to cut PDMS thin films (FIG. 20), ECM proteins are microcontact printed (as described above) and this assembly is enclosed in a microfluidic chamber. Alternatively, the thin films are produced with a hydrogel (FIGS. 21 and 31). Muscle cells are cultured on these thin films and/or hydrogels and the contractile stresses are quantified by optically monitoring the extent of curvature of the muscular thin films (FIG. 22). An alternative strategy for measuring contractility is depicted in FIG. 23, where the cells are grown on a wrinkling substrate.

Figure 42:
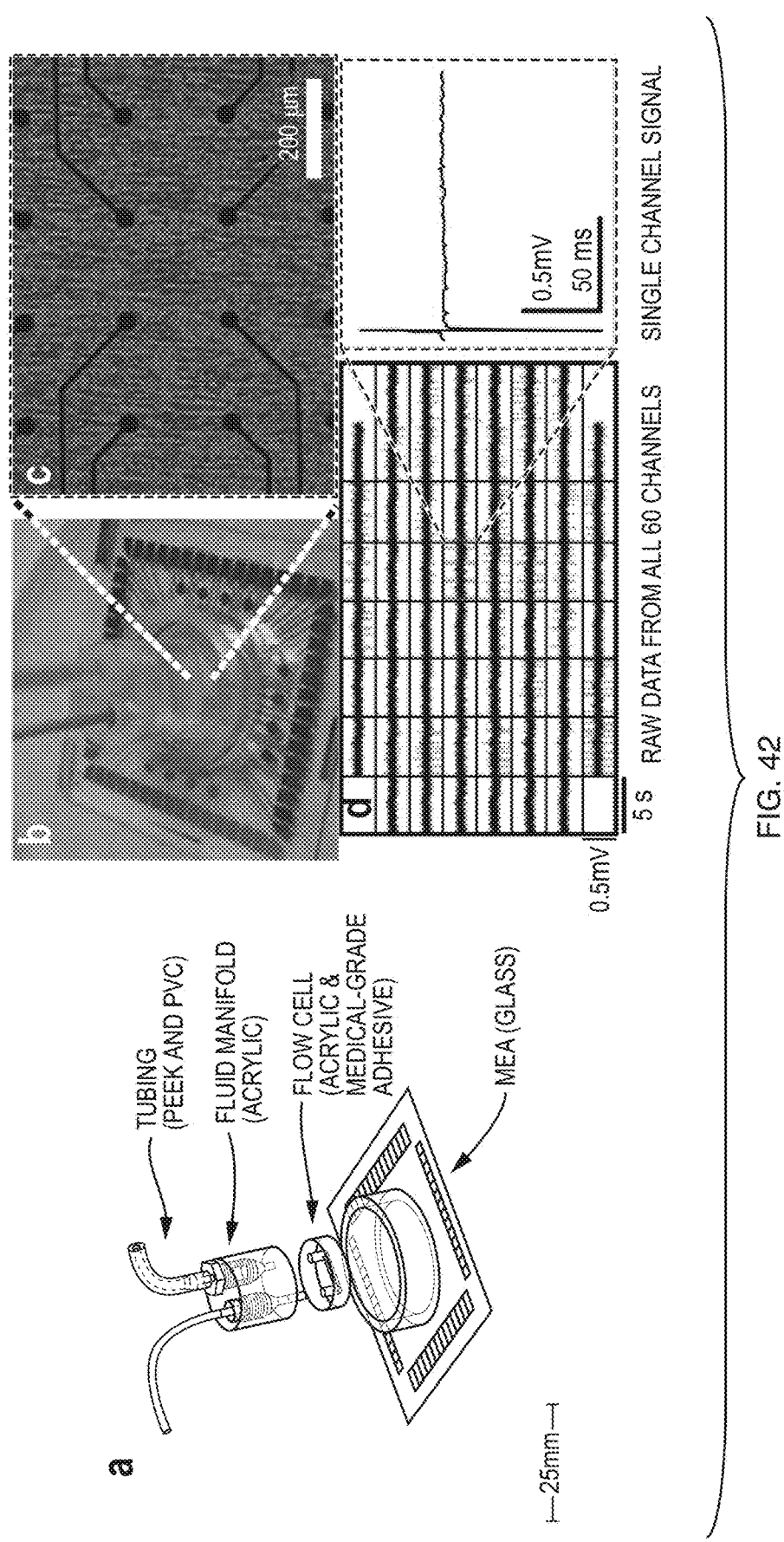
FIG. 42 depicts one embodiment of an electrophysiology (EPhys) chip using commercially-available multiple electrode array substrates. a) A CAD render of a fluidic, e.g., microfluidic, chip design utilizing layers of non-cytotoxic double-sided adhesive and machined and/or laser cut PMMA layers which are bonded to an electrode array base. Above, a manifold, which has fluidic and pneumatic tubing pre-installed, is attached. In this fashion, other chips can be integrated in series or in parallel with the electrophysiology chamber.
Figure 43:
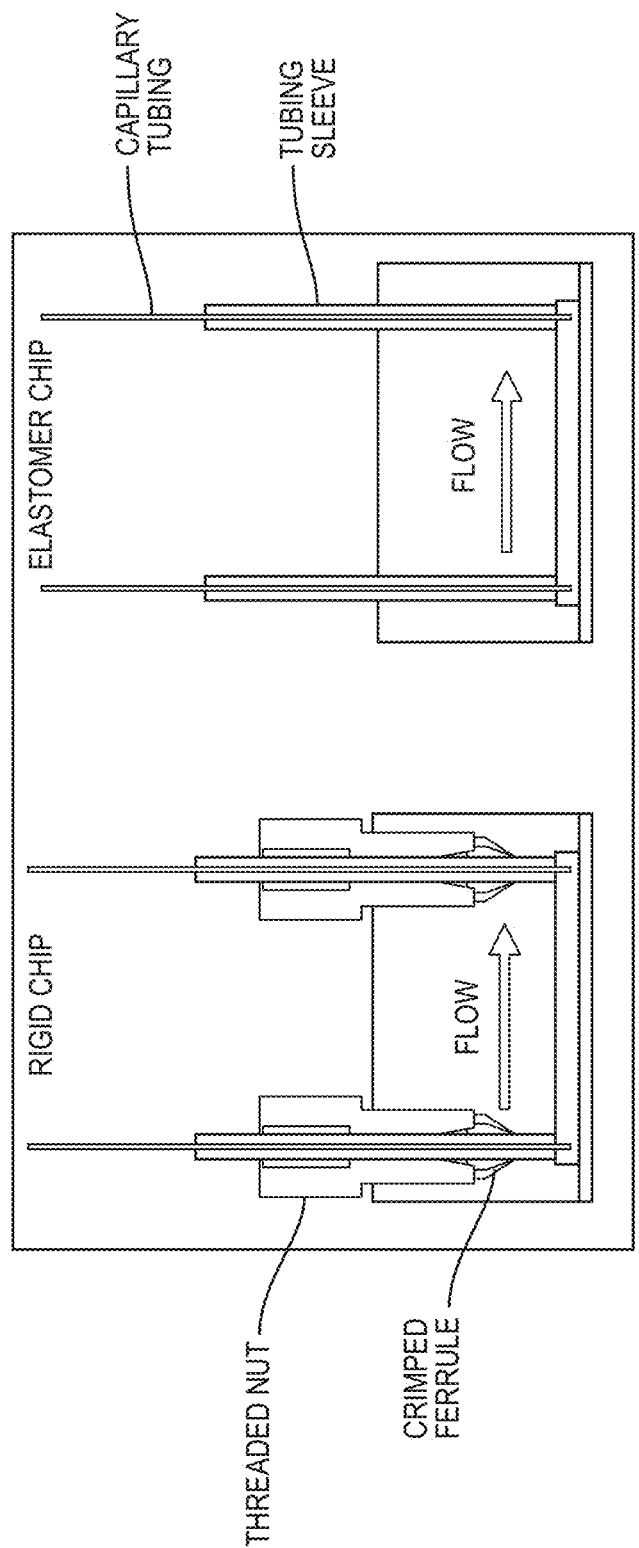
FIG. 43 depicts two embodiments for connecting chips fabricated using various techniques to commercially-available tubing and fittings. The rigid chip connects through the use of a manifold, which contains a gasket between the manifold and the chip to create a hermetic seal. In an elastomeric chip, the elastomer may be used as a gasket. In this manifestation, a manifold may be used or the tubing can be introduced into pre-existing ports to provide a hermetic seal. Using commercially-available tubing, this creates a fluidic volume between 10 nL and 5 uL for a minimum length of tubing between two chips.
Figure 44:
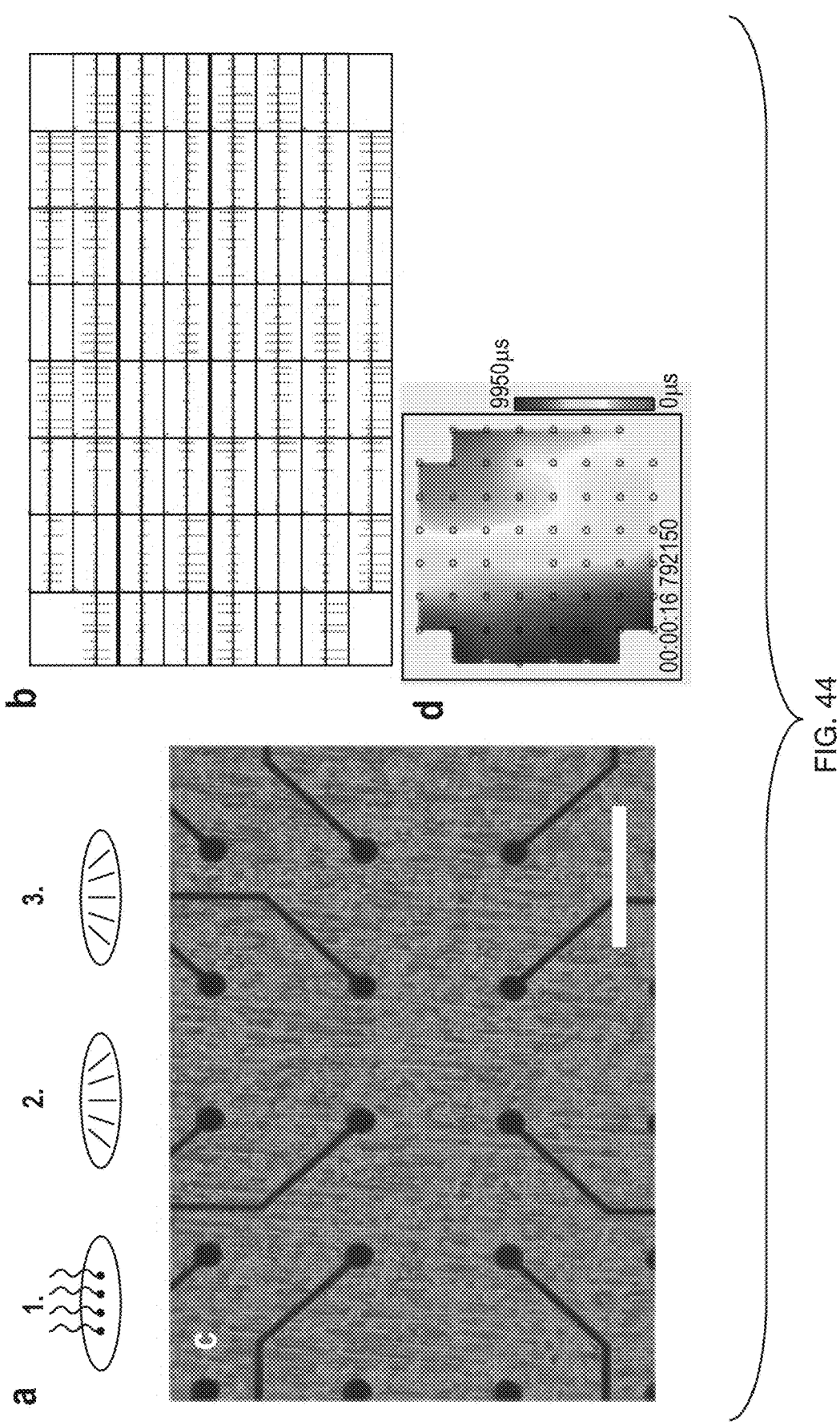
FIG. 44 depicts one embodiment for fabricating an EPhys chamber comprising aligned muscle tissues for electrophysiological recording. a) process for creating aligned muscular tissue on electrode array surface. 1. UV-ozone treatment of silicon nitride surface of MEA. 2. Stamp oxidized surface with fibronectin (or any ECM protein) using microcontact printing with desired pattern (this manifestation demonstrates 15 micron wide lines with 2 micron spacing) 3. Block non-patterned area with surfactant, such as Pluronics F-127 (BASF). b) Field potential recordings from all 60 channels (top) from day 4 NRVMs on 15×2 um micropatterned fibronectin on MEA surface. Windows: x=5 sec, y=±500 μV. c) Day 3 cardiomyocytes on 15×2 um micropatterned fibronectin on MEA surface. Scale bar=200 μm. d) Conduction velocity represented by isochrone map of field potential arrival times. Scale: red=0 ms, blue=10 ms.
Figure 45:
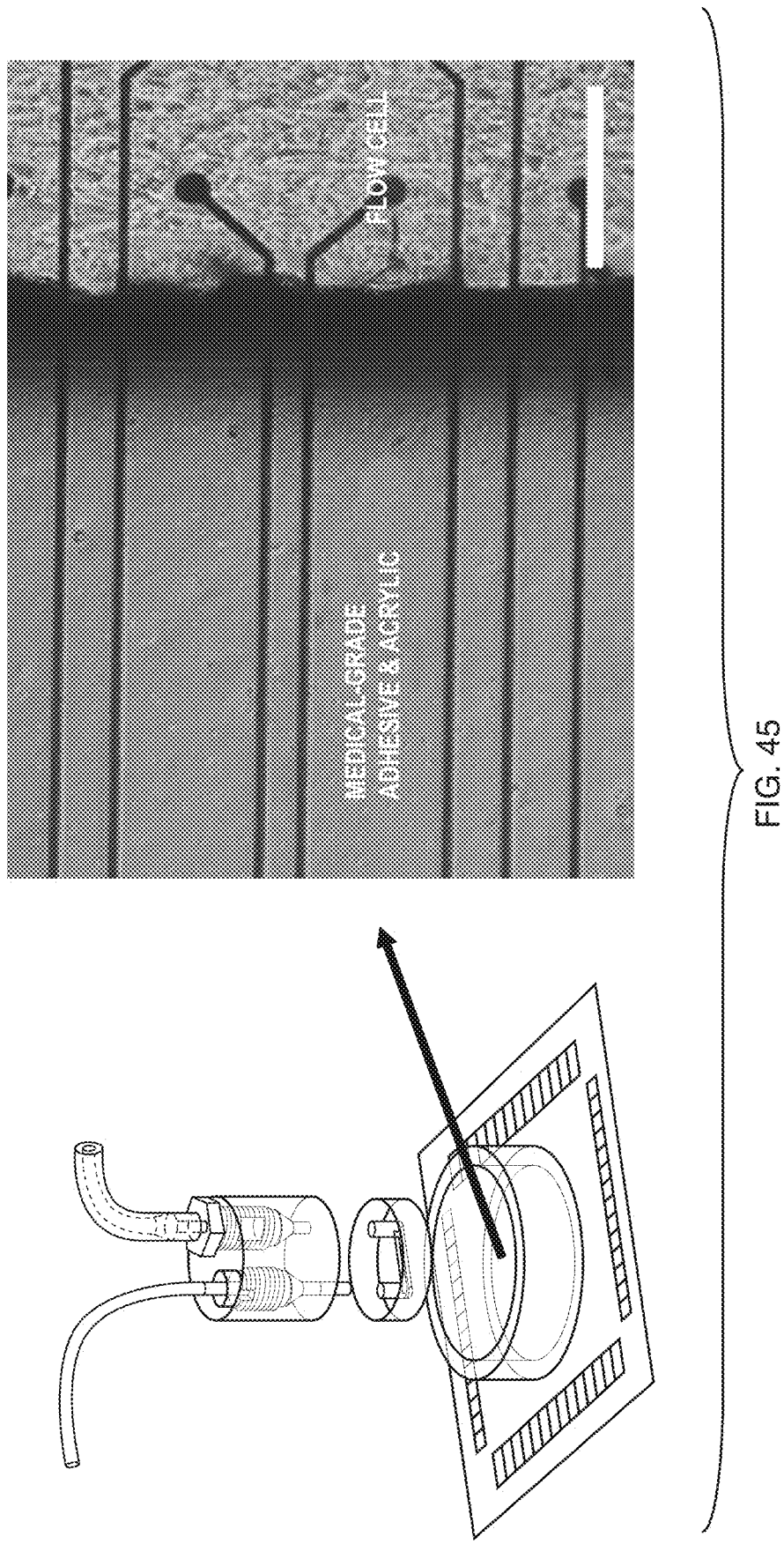
FIG. 45 depicts an embodiment of an electrode array chip. Using rapid prototype fabrication tools to create chip layers, cardiac cells have been cultured in microfluidic flow cells for up to four days or more on stiff surfaces (GPa), e.g., PDMS. On soft surfaces, e.g., hydrogels (kPa) cells stay adherent and contractile for up to 29 days or more. In the embodiment depicted in this figure, the cells were seeded at a density of $2-3\times10^6$ cells/mL medium, which results in $20-30\times10^3$ cells per chamber (10 μL chamber). The image on the right was taken at 10× magnification and illustrates the border of the flow cell. Scale bar=200 μm.

For the EPhys chambers, anisotropic muscle cell monolayers are cultured in a low volume chamber, electrically field stimulated using the electrodes on the top and action potentials are recorded using the microelectrode array on the bottom (see, e.g., FIGS. 42 and 44). The base of the EPhys chamber may be, for example glass with embedded electrodes, e.g., MEA, or a flexible polymer, e.g., PDMS, with embedded electrodes.

The electrode(s) read-outs provide the action potential characteristics of the cardiomyocyte monolayer.

The cells are exposed to test compounds to determine if they have any cardiotoxic effects. Since the tissue architecture is controlled, the effect of a test compound can be determined by determining the contractile efficiency of the tissues. In addition, since the tissue architecture can be controlled, various disease states can be modeled and the effect of the disease state and/or a test compound can be determined by determining the contractile efficiency of the tissues.

Figure 24:
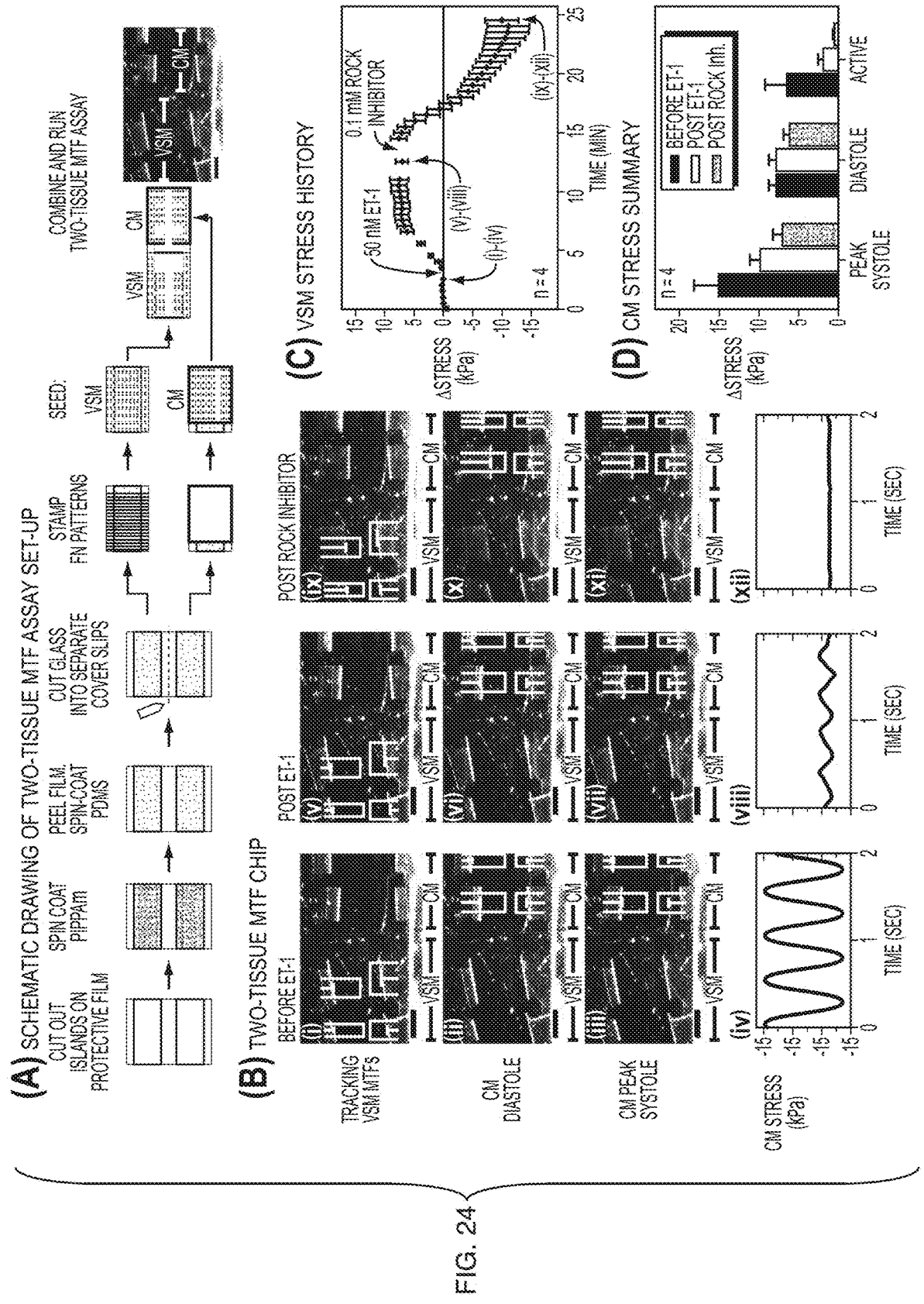
FIG. 24 depicts the physiological response of human vascular smooth muscle (VSM) and engineered rat cardiac muscle (CM) on the same chip to drugs. (A) Manufacture of the chip with two different kinds of muscle (striated and smooth) (B) Tracking MTF deformation during the contractility assay. (C) and (D) The contractility of the VSM is considerably slower than the CM and the stress histories are depicted uniquely for each one.
Figure 25:
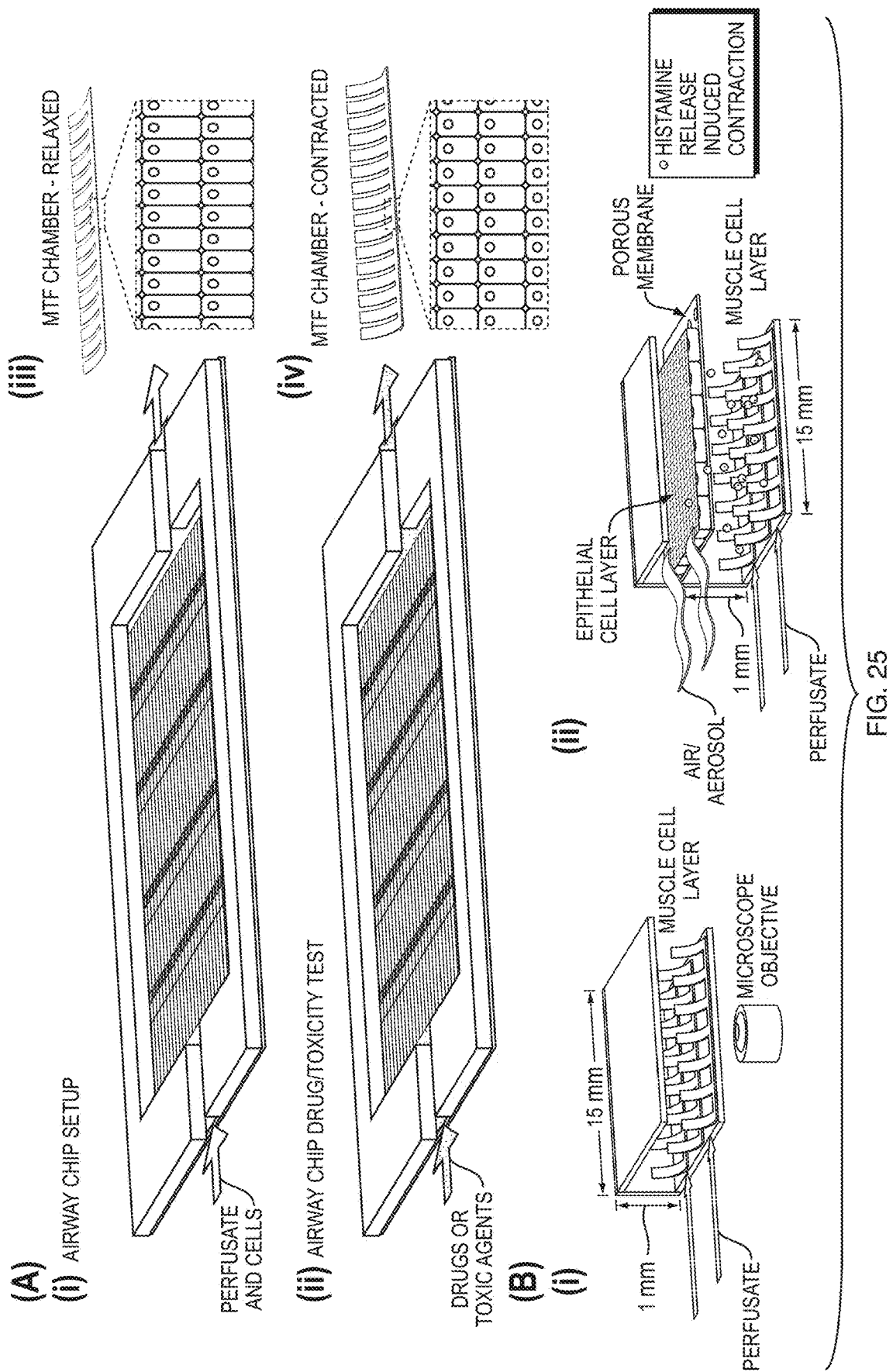
FIG. 25 schematically depicts an airway-on-a-chip. (A) Airway on a chip is composed of healthy bronchial tissue, cultured in liquid media (i) with the possibility of drug perfusion (ii). The cell monolayer will exhibit a linear arrangement of cells, adhered to the top surface of a PDMS muscular thin film. Incubation in culture media would yield relaxed bronchial thin films (iii), while incubation with drugs yields contracted bronchial thin films (iv). The contractility is measured for grading the drug response in the tissue. (B) Schematic represents the dimensions of an airway chip containing multiple bronchial thin films (i), with the possibility to add a layer of epithelial columnar cells (ii). This cell layer is adhered to a porous membrane that separates the bronchial from epithelial cells, and is exposed to air flow or air flow plus aerosoles.
Figure 26:
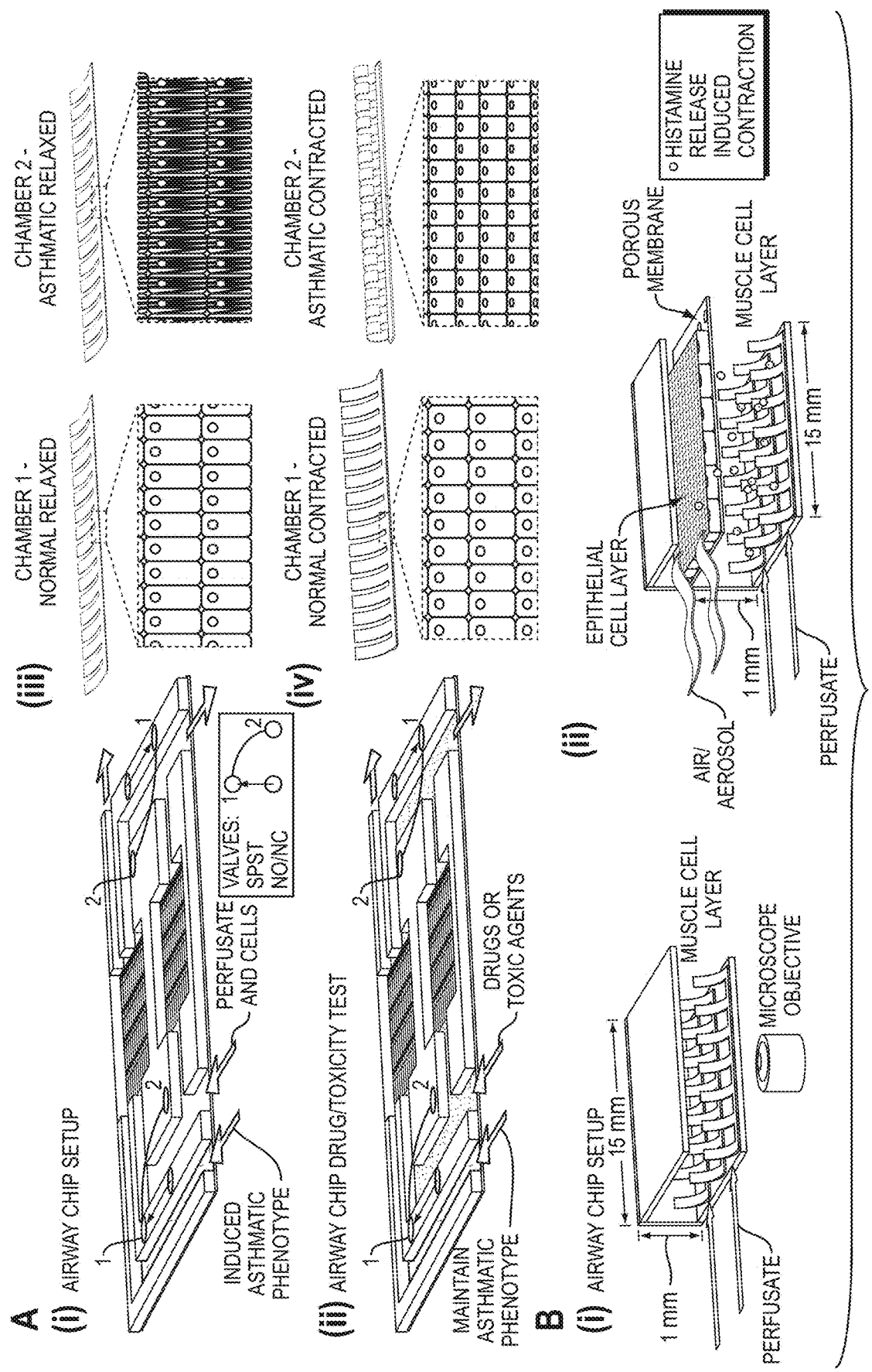
FIG. 26 schematically depicts an airway-on-a-chip comprising two microfluidic chambers. (A) Airway-on-a-chip with two chambers. Chamber 1 contains healthy bronchial tissue, while bronchial tissue with an asthmatic phenotype is contained in Chamber 2. The asthmatic phenotype is composed of cultures from human diseased cells or induced artificially (i.e., by toxic agents, temperature). Chambers 1 and 2 are cultured in liquid media (i) with the possibility of drug perfusion (ii). Media and/or drugs can be kept separate between Chamber 1 and Chamber 2 by the closing of a valve (pictured in the legend, with a single pole, single throw (SPST) and Normal Open/Normal Close (NO/NC) valve). Monolayers of healthy and asthmatic cells exhibit an anisotropic organization and may be adhered to the top surface of PDMS muscular thin films and/or a hydrogel. Incubation in culture media yields relaxed thin films and/or hydrogels (iii), while incubation with drugs yields contracted thin films and/or hydrogels (iv). The contractility is measured for grading the response of the different tissue types to the drugs. (B) One embodiment of the invention which schematically depicts the dimensions of an airway chip containing multiple bronchial thin films (i), with the possibility to add a layer of epithelial columnar cells (ii). This epithelial cell layer is adhered to a porous membrane that separates the bronchial muscle from the epithelium, and is exposed to air flow or aerosoles.

For example, FIG. 24, shows the physiological response of human vascular muscle cell MTFs and cardiac muscle MTFs on the same heart-on-a chip to various drugs.

Example 7: Airway Smooth Muscle-On-A Chip

Asthma is a prevalent disease affecting ~8% percent of the population, and it is caused by the maladaptive remodeling of bronchial smooth muscle. Airborne toxins and air pollution can affect the bronchial smooth muscle, but these are difficult to detect and their effect on the tissue health is also difficult to predict (and reflects a large scale problem in developing countries). There are currently no commercially available instruments to test cytotoxicity and allergic responses and associated inflammation in vitro, despite the existence of human bronchial smooth muscle cell lines. Beyond the difference in species responses to toxic or therapeutic agents, animal models do not necessarily provide human relevance, predictability, and lower failure rates in the drug pipe-line.

Bronchial smooth muscle spasms are a possible response to both allergens and toxins. This response can be amplified if the muscle undergoes a maladaptive remodeling prior to the introduction of the toxic agent (such as in asthmatic patients). An efficient, "on a chip," in vitro system to test for bronchial smooth muscle spasms would provide a tool to test drugs for curing or exacerbating asthma, test toxins in the field, and/or predict the allergic response of different patient populations.

The present example demonstrates a solution to fill this need by the preparation of a device that provides an in vitro platform for bronchial smooth muscle spasm testing. The devices described herein also provide a platform to test the contractility of human bronchial smooth muscle tissue. In addition, primary cells isolated from different populations of patients can be used with these devices to study the effectiveness of drugs for different subsets of the population. For example, read-outs from these devices regarding the contractility and proliferation of the bronchial smooth muscle can be related to lung capacity curves (rate of inhale/exhale) and compared to the output of pulmonary function tests in the clinic. In addition, the secretion of mucus granules and spherules in the epithelium are monitored optically as a means to test for mucous secretion that is a hallmark of bronchitis and other obstructive pulmonary diseases. Furthermore, patients with advanced chronic obstructive pulmonary disease like chronic bronchitis often exhibit bluish tinted skin, resulting from hypoxia and fluid retention. The devices described herein can be used to test the media for low oxygen levels and arterial blood gas (measuring ability to oxygenate blood at alveoli) "downstream" of obstructed airways.

Accordingly in some embodiments the present example provides fluidic, e.g., millifluidic and/or microfluidic, devices comprising bronchial smooth muscle tissue and an endothelial cell monolayer to test for "spasms" in response to drugs or toxins. This example also provides fluidic, e.g., millifluidic and/or microfluidic, devices comprising one chamber comprising bronchial smooth muscle tissue and an endothelial cell monolayer and another chamber comprising bronchial epithelial and/or pulmonary mast cells, which are a key to exacerbation and inflammation response (see, e.g., FIGS. 24-26).

In particular, in some embodiments, the airway smooth muscle-on-a-chip may comprise a hybrid bronchial smooth muscle and columnar epithelium organ system to test bronchial spasms in response to drugs and/or toxins. This hybrid chip is installed inside a two-chamber microfluidic device that contains a top layer of human epithelial cells adhered to a porous membrane and exposed to air flow and a bottom layer containing horizontal muscle tissues, e.g., MTS and/or hydrogel engineered tissues, each composed of a confluent monolayer of bronchial smooth muscle situated on top of a PDMS and/or hydrogel substrate, which are incubated within a liquid medium. The contraction of the bronchial smooth muscle is measured with a device, e.g., an optical signal capturing device or a device for translating contractility into an electrical or magnetic signal, e.g., piezoresistive, piezoelectric, or strain sensor, e.g., embedded within the thin film and/or hydrogel by monitoring the extent of curvature of the muscle tissue. Approximately 0.25 million muscle cells are needed for each muscle tissue chamber.

In some embodiments, muscle contraction is measured by adhesion of a bronchial smooth muscle cell monolayer on a swiss cheese-like PDMS and/or hydrogel membrane, where muscular contraction causes deformation of the holes within the membrane. The porous membrane separating the top and bottom layers of the chamber acts as a barrier between the two cell types and allows for chemical exchange. The human bronchial smooth muscle cells are composed of commercially available lines or primary human cells, from either healthy or asthmatic patients.

These devices also permit induction of an asthmatic phenotype chemically (e.g., by introducing IL-13 to the culture medium) or by alteration of temperature or media composition. Additionally, some drug therapies for the treatment of asthma can themselves cause asthmatic attacks. The asthmatic phenotype would present as exaggerated bronchial muscle spasms, which would be reflected by changes in contractility. As a control, the effect of substances with known toxicity in humans (e.g., local anesthetics such as procaine, chloroprocaine, and tetracaine) are introduced to induce bronchial smooth muscle spasms and provide a calibration to existing patient response from the clinic. The co-culture system allows for monitoring the presence of inflammation factors (IL-3, IL-4, IL-5, IL-13) that cause bronchial smooth muscle spasms. Further, the hyperplasia and hypertrophy of the columnar epithelial cells (hallmarks of obstructive pulmonary disease) are assessed optically, as is the secretion of mucous granules and spherules. Further, reduction in oxygen levels in the media are also monitored. An added benefit of integration in a multi-organ system is that it is possible to evaluate drugs that are effective for treating bronchial smooth muscle spasms, but toxic to other organs (e.g., ventolin). Likewise, the devices of the invention allow for the testing of drugs commonly used to affect the function of other organs (e.g., beta blockers that reduce cardiac contractility), but can adversely affect airway resistance in asthmatics.

In order to prepare an airway smooth muscle cell-on-a-chip, human bronchial smooth muscle cells (commercially available form Lonza, CC2576) are cultured. Engineered smooth muscle tissue with well-defined cellular organization and tissue geometry is fabricated as described herein.

Commercially-available healthy human columnar epithelial cells (ATCC; PCS-300-010, PCS-310-010, Lonza: CC-2540, CC-2547) and/or diseased human bronchial epithelial cells (available from Lonza; Ser. No. 00/195,275, 00194911) are cultured and micro-contact printing is used to fabricate engineered human columnar epithelium with well-defined cellular organization and tissue geometry.

The devices and methods may be used to study diseased human airway smooth muscle.

Microphysiological Chip Design and Fabrication

To fabricate an airway smooth muscle cell-on-a-chip, an MTFchamber comprising laser muscle tissue, e.g., horizontal muscle tissue, e.g., engraved PDMS and/or hydrogel thin films are prepared as described supra and are enclosed in an assembly of a fluidics chamber. Muscle cells are cultured on these thin films and the contractile stresses are quantified using a device, e.g., an optical signal capturing device or a device for translating contractility into an electrical or magnetic signal, e.g., piezoresistive, piezoelectric, or strain sensor, e.g., embedded within the thin film and/or hydrogel, monitoring the extent of curvature of the muscle tissue. A two chamber system can also be engineered for dual outputs (see, e.g., FIG. 26).

In order to separate airway smooth muscle from the epithelium within the hybrid organ system, a membrane material, such as Clear flex 50 polyurethane may be used. Such a membrane has the following properties: it is biocompatible, complies with IS 10993-5 (in vitro cytotoxicity tests for medical devices), has low absorption of hydrophobic dye/drug and other chemical compounds, is cell adhesive, is optically clear, is highly flexible, moldable, bondable, has low autofluorescence, and does not swell in water The adhesion of cells onto the membrane may be shown by characterizing the structural and functional response of cells by quantifying cytoskeletal alignment and effects on gene expression and protein translation. Cellular response to mechanical stimuli may also be monitored. For example, the bronchial smooth muscle tissue is monitored for contraction in response to drug or toxic agents (e.g., IL-13, acetylcholine). The contractility is measured for grading the response of the different tissue types to the drugs.

To generate disease models of airway smooth muscle by integration of diseased cells (e.g., asthmatic or COPD) or by chemical stimulation of the asthmatic phenotype, the asthmatic muscle phenotype is integrated into the microfluidic device(s) described above. In the same chamber, the levels of oxygen within the medium, cellular ATP, apoptosis, and intracellular calcium are monitored.

An asthmatic phenotype may be induced by introduction of allergens/drug compounds that drive bronchial spasms associated with asthmatic attacks into the devices. In addition, toxic agents (e.g., acetylcholine, IL-13) may be perfused into the culture medium containing the muscle cell monolayer. Alterations in smooth muscle contraction in response to allergens or toxic agents is monitored. In the same channel, the levels of oxygen within the medium, cellular ATP, apoptosis, and intracellular calcium are monitored. In the upper channel containing the epithelium, the levels of mucus granules and spherules and presence of inflammation factors (IL-3, IL-4, IL-5, IL-13) are monitored.

In some embodiments, asthmatic or COPD human primary smooth muscle cells (from either commercially available cell lines or samples from asthmatic patients) are co-cultured with the diseased human primary bronchial epithelial cell.

More specifically, in order to fabricate an airway smooth muscle cell-on-a-chip with multiple chambers, patterning of ECM, microgrooves, stretching of the chip, or other similar techniques can be used to control cell shape and tissue alignment within the chambers to recapitulate the native microenvironments. Cells are seeded and media is supplied through micro-fluidic channels. The bronchial smooth muscle cells are of human origin from commercially available cell-lines or primary cells from human healthy or asthmatic patients (FIG. 24).

In some embodiments, the bronchial smooth muscle cells may be co-cultured with other cell types. For example, bronchial epithelial cells can be cultured within the same chamber separated by a transwell membrane, and exposed to exacerbating pollutants, such as oil fly ash (available commercially), dust mites, or smoke. Bronchial smooth muscle cells can be combined with pulmonary mast cells either upstream in the microfluidic device or within a transwell chamber. An asthmatic phenotype can be induced chemically (e.g., by adding IL-13 during culture), by temperature control, or alteration of media composition in some of the chambers (FIG. 26A(i), chamber 2). Further, the asthmatic phenotype can be incorporated into the chip by samples derived from asthmatic patients.

If desired, a therapeutic drug may be added to the chamber (e.g., a drug is introduced to induce a normal smooth muscle contractile response, or a toxic agent to test for bronchial spasms (e.g., acetylcholine)). Drugs can be added via both intravenous and aerosol routes, exhibiting the versatility of the chip design.

Contraction of the muscle can be detected using multiple approaches. For example, by making the chamber substrates out of PDMS and or hydrogels, it is possible to optically track the bending of each muscle tissue as a measure of contractility. Alternatively, a substrate with micro-holes, which will be small enough to be impermeable to the cells, may be used. These holes will provide the material with greater flexibility, and their shape can be used as an indicator of the amount of contraction by reading out their shape based on the transmitted light (FIG. 23B(i)). Rows of oval micro-holes of varying flexibilities may also be used, such that conduction is possible through the wires in the material if the holes are completely closed. The row of micro-holes with minimal flexibility that still conducts will provide the readout of the degree of contraction of the tissue (FIG. 23B(ii)). Materials that will vary color with different degrees of stress may also be used.

The output readout of the contractility and proliferation of the bronchial smooth muscle will be related to lung capacity curves (rate of inhale/exhale) by modeling the average material properties of the endothelial layer estimated from histological data and the stiffness of the muscle layer will be calculated from the in vitro experimental data (from chip). These data will be used to calculate the diameter of the bronchial tube, which will be used to calculate the airflow/resistance (e.g., clinical outputs).

For example, FIG. 27 shows physiological responses of healthy engineered human bronchial smooth muscle cells and chemically induced asthma bronchial smooth muscle cells using the devices of the present example.

The foregoing devices are referred to herein as a "airway smooth muscle-on-a-chip". In one embodiment, a airway smooth muscle-on-a-chip is further integrated, e.g., via microfluidic connection, with additional organs-on-a-chip, e.g., heart chips as described above, lung chips to mimic breathing lung, liver chips to mimic metabolic liver, kidney chips to mimic flowing kidney, gut chips to mimic peristalsing gut, skeletal muscle chips to mimic contracting skeletal muscle, skin chips to mimic skin barrier, brain chips to mimic blood-brain barrier, testis chips to mimic reproductive/endocrine testis and bone marrow chips to mimic self-renewing bone marrow.

Example 8: Skeletal Muscle-On-A Chip

This example describes the preparation and use of a fluidic, e.g., millifluidic and/or microfluidic, device which, in one embodiment, comprises cultured mature human skeletal muscle myotubes on 2D PDMS substrates and/or microcontact printed and/or micromolded hydrogel, e.g., alginate and/or gelatin, substrates. These tissue constructs are integrated into both a "muscular thin film" chamber for contractility measurements and a low volume electrophysiological readout chamber. In another embodiment, this example describes the preparation and use of a fluidic, e.g., millifluidic and/or microfluidic, device which comprises cultured mature human skeletal muscle myotubes and human adipocyes co-cultured on 2D PDMS substrates and/or microcontact printed and/or micromolded hydrogel, e.g., alginate and/or gelatin, to recapitulate two tissue interfaces and create disease models within the device.

Human Skeletal muscle cells which are cultured in an anisotropic monolayer or healthy and Type-I and Type-II diabetic adipocytes may be used.

Contractility is measured via a device, e.g., an optical signal capturing device or a device for translating contractility into an electrical or magnetic signal, e.g., piezoresistive, piezoelectric, or strain sensor, e.g., embedded within the thin film and/or hydrogel, to track muscle tissue deformation/membrane deformation. Electrophysiological recordings (1 lead or 2 lead EMG measurements) are taken via an embedded microelectrode array. The tissues from one or both chambers may be further used to determine the effect of various test compounds on the expression and/or activity of various markers of muscle damage such as creatine kinase and slow and fast-twitch troponin I (ssTnl, fsTnl). In addition, metabolic burn rates and insulin level may be quantified.

The devices described herein may also be used to replicate statin induced skeletal muscle myopathy by exposing the chip to Cerivastatin and measuring damage markers such as creatine kinase and slow and fast-twitch troponin I (ssTnl, fsTnl). Since muscle weakness is also a generalized complaint of patients undergoing statin treatment, skeletal muscle contractility measurements are used to validate statin-induced in vitro muscle weakness. A diabetic muscle microenvironment may also be created in the devices described herein by co-culturing type I and type II preadipocytes with skeletal muscle cells. Type I diabetic mimic chips are used to evaluate insulin replacement therapies while Type II diabetic mimic chips are used to determine effectiveness of metformin-induced metabolic benefits.

Cellular Components of an In Vitro Skeletal Muscle Construct

Human myoblasts are commercially available (primary cell lines (healthy; Lonza, XM13A1 and XM15B1) and primary satellite cells from healthy patients) are cultured as aligned monolayers of muscle cells on microcontact printed PDMS substrates, microcontact printed polyurethane membranes and/or microcontact printed and/or micromolded hydrogel, e.g., alginate and gealtin substrates.

Human adipocytes (commercially primary preadipocytes (Lonza; PT-5022)) are differentiated into adipocytes using supplied differentiation medium and culture adipocyte on opposite side of porous membrane that myoblast/neurons are cultured. Diabetic (Type I and II) human adipocytes (from patients with diabetes) preadipocytes (Lonza; PT-5023—Type I and PT-5024 Type II)) are differentiated into adipocytes by using supplied differentiation medium and culture adipocyte on opposite side of porous membrane that myoblast/neurons are cultured.

Microphysiological Chip Design and Fabrication

The devices are fabricated (FIG. 28) using laser engraving process to prepare horizontal muscle tissues, e.g., horizontal MTFs on PDMS and/or horizontal hydrogel engineered muscle tissues, microcontact print ECM proteins and enclose the assembly in a fluidic chamber. Muscle cells are cultured on these thin films and the contractile stresses are quantified by monitoring the extent of curvature of the muscular thin films using e.g., an optical signal capturing device or a device for translating contractility into an electrical or magnetic signal, e.g., piezoresistive, piezoelectric, or strain sensor, e.g., embedded within the thin film and/or hydrogel.

Anisotropic muscle cell monolayers are cultured in a low volume chamber, electrically field stimulated using the electrodes on the top and action potentials are recorded using the microelectrode array on the bottom as described supra.

Figure 30:
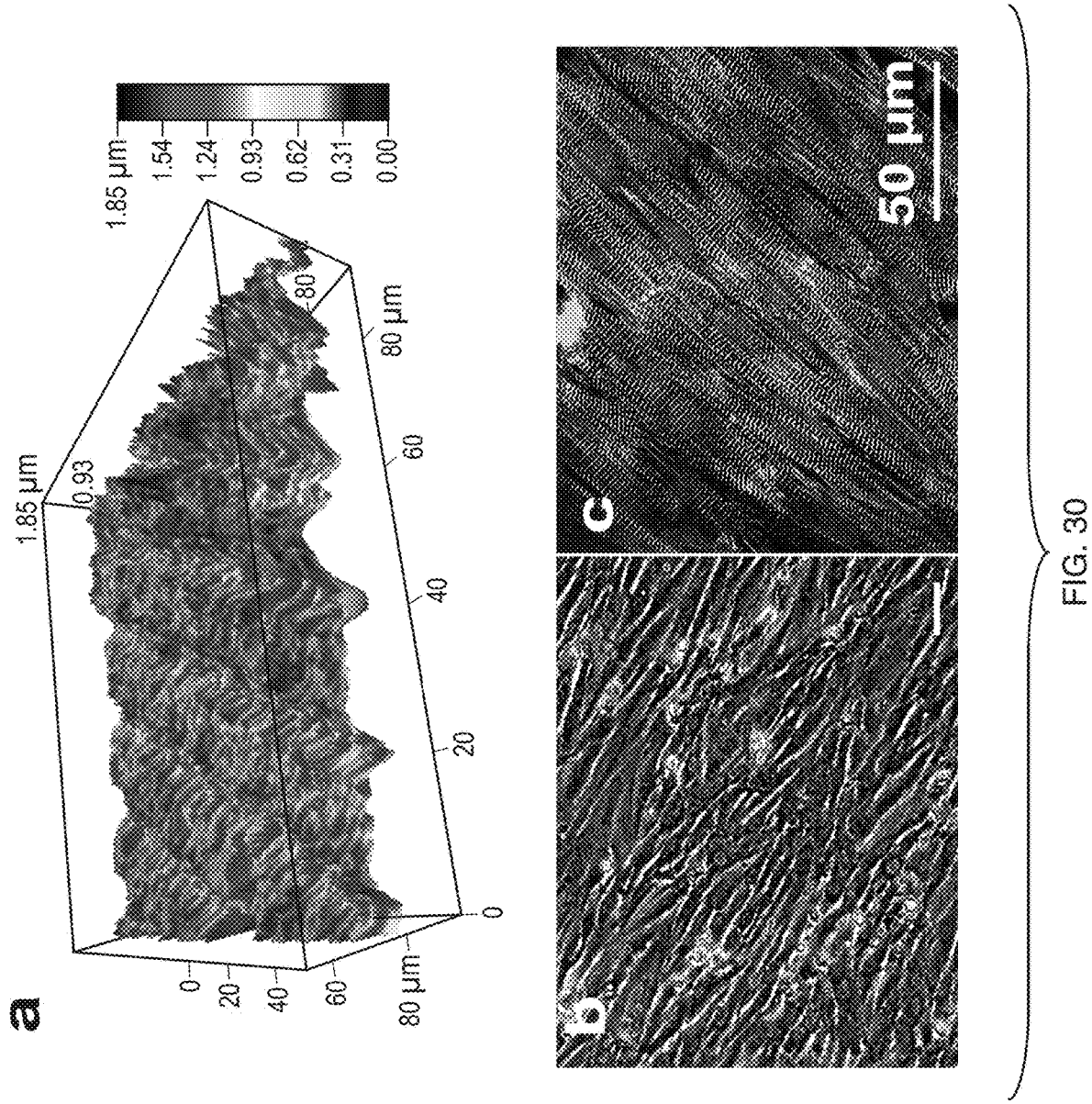
FIG. 30 depicts anisotropic cardiac tissue formation on micromolded alginate substrates. (a) The micromolding techniques, described herein, replicate faithfully the original pattern. (b) Phase contrast image of representative anisotropic tissues cultured on micromolded alginate surfaces, (c) Immunofluorescence composite images of anisotropic tissues cultured on micromolded alginate surfaces; actin is dark gray, nuclei are medium gray and α-actinin is light gray. Scale bar equals 50 µm.

Contractility is measured and recorded in devices comprising co-cultured muscle cells and adipose cells in the MTF chamber and the EPhys chamber is used to record EMG (FIG. 29). To ensure that mature myotubes receive the proper 3D cues, the skeletal muscletissues may be micromolded with grooves sufficient to maintain mature contracting muscle in culture (FIG. 30).

The foregoing devices are referred to herein as a "skeletal muscle-on-a-chip". In one embodiment, a airway smooth muscle-on-a-chip is further integrated, e.g., via microfluidic connection, with additional organs-on-a-chip, e.g., heart chips and/or airway smooth muscle cell chips as described above, lung chips to mimic breathing lung, liver chips to mimic metabolic liver, kidney chips to mimic flowing kidney, gut chips to mimic peristalsing gut, skin chips to mimic skin barrier, brain chips to mimic blood-brain barrier, testis chips to mimic reproductive/endocrine testis and bone marrow chips to mimic self-renewing bone marrow.

EQUIVALENTS

In describing embodiments of the invention, specific terminology is used for the sake of clarity. For purposes of description, each specific term is intended to at least include all technical and functional equivalents that operate in a similar manner to accomplish a similar purpose. Additionally, in some instances where a particular embodiment of the invention includes a plurality of system elements or method steps, those elements or steps may be replaced with a single element or step; likewise, a single element or step may be replaced with a plurality of elements or steps that serve the same purpose. Further, where parameters for various properties are specified herein for embodiments of the invention, those parameters can be adjusted up or down by $\frac{1}{20}$th, $\frac{1}{10}$th, $\frac{1}{5}$th, $\frac{1}{3}$rd, $\frac{1}{2}$, etc., or by rounded-off approximations thereof, unless otherwise specified. Moreover, while this invention has been shown and described with references to particular embodiments thereof, those skilled in the art will understand that various substitutions and alterations in form and details may be made therein without departing from the scope of the invention; further still, other aspects, functions and advantages are also within the scope of the invention. The contents of all references, including patents and patent applications, cited throughout this application are hereby incorporated by reference in their entirety. The appropriate components and methods of those references may be selected for the invention and embodiments thereof. Still further, the components and methods identified in the Background section are integral to this disclosure and can be used in conjunction with or substituted for components and methods described elsewhere in the disclosure within the scope of the invention.

What is claimed:

1. A device for measuring a contractile function, the device comprising:
    a solid support structure, wherein the solid support structure is a fluidic device comprising a first chamber and a second chamber operably connected,
    wherein said first chamber comprises a monolayer of muscle cells and an electrophysiological capturing device; and
    said second chamber comprises a plurality of muscle tissue strips and a device to measure contractility,
    wherein the plurality of muscle tissue strips comprise a flexible polymer layer and/or a hydrogel layer and a population of isolated muscle cells seeded on the flexible polymer layer and/or the hydrogel layer in a predetermined pattern, wherein said muscle cells form a muscle tissue structure which can perform a contractile function.

2. The device of claim 1, wherein the monolayer of muscle cells and the isolated muscle cells are independently selected from the group consisting of cardiac muscle cells, ventricular cardiac muscle cells, atrial cardiac muscle cells, striated muscle cells, smooth muscle cells, and vascular smooth muscle cells.

3. A method for identifying a compound that modulates a contractile function, the method comprising
    providing the device of claim 1; and
    determining the effect of the test compound on a contractile function of said monolayer of muscle cells and/or said plurality of muscle tissue strips in the presence and absence of the test compound, wherein a modulation of the contractile function of said monolayer of muscle cells and/or said plurality of muscle tissue strips in the presence of said test compound as compared to the contractile function in the absence of said test compound indicates that said test compound modulates a contractile function, thereby identifying a compound that modulates a contractile function.

4. A device for measuring a contractile function, the device comprising:
    a solid support structure, wherein the solid support structure is a fluidic device comprising a first chamber and a second chamber operably connected, wherein said first chamber comprises a plurality of muscle tissue strips and a device to measure contractility,
    wherein the plurality of muscle tissue strips comprise a flexible polymer layer and/or a hydrogel layer and a population of isolated diseased cells seeded on the flexible polymer layer and/or the hydrogel layer in a predetermined pattern, wherein said diseased muscle cells form a muscle tissue structure which can perform a contractile function; and
    wherein said second chamber comprises a plurality of muscle tissue strips and a device to measure contractility, wherein the plurality of muscle tissue strips comprise a flexible polymer layer and/or a hydrogel layer and a population of isolated healthy muscle cells seeded on the flexible polymer layer and/or the hydrogel layer in a predetermined pattern, wherein said healthy muscle cells form a muscle tissue structure which can perform a contractile function.

5. A device for measuring a contractile function, the device comprising:
    a solid support structure, wherein the solid support structure is a fluidic device;
    a plurality of muscle tissue strips, wherein the plurality of muscle tissue strips comprise a flexible polymer layer and/or a hydrogel layer and a population of isolated airway smooth muscle cells seeded on the flexible polymer layer and/or the hydrogel layer in a predetermined pattern, wherein said airway smooth muscle cells form a muscle tissue structure which can perform a contractile function.

6. The device of claim 5, further comprising a porous membrane having epithelial cells adhered thereto and exposed to air flow situated above the muscle tissue strips.

7. The device of claim 6, wherein the solid support structure is a fluidic device comprising a first chamber and a second chamber operably connected,
    wherein said first chamber comprises a plurality of muscle tissue strips comprising a population of isolated healthy airway smooth muscle cells; and,
    said second chamber comprises a plurality of muscle tissue strips comprising a population of isolated diseased airway smooth muscle cells.

8. A method of preparing a fluidics device suitable for measuring a contractile function, the method comprising
    providing a solid support structure;
    coating a sacrificial polymer layer on the solid support structure; coating a flexible polymer layer that is more flexible than the support structure on the sacrificial polymer layer, wherein the flexible polymer layer does not cover the edges of said solid support structure; seeding cells on the flexible polymer layer; culturing the cells to form a tissue; and removing a portion of said formed tissue thereby generating strips of said formed tissue; attaching fluidics components to the solid support structure comprising the tissue, thereby preparing a device suitable for measuring a contractile function.

* * * * *